(12) United States Patent
Cassayre et al.

(10) Patent No.: US 8,309,567 B2
(45) Date of Patent: *Nov. 13, 2012

(54) SPIROINDOLINE DERIVATIVES HAVING INSECTICIDAL PROPERTIES

(75) Inventors: Jérôme Cassayre, Basel (CH);
Louis-Pierre Molleyres, Basel (CH);
Peter Maienfisch, Basel (CH); Fredrik Cederbaum, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 1186 days.

This patent is subject to a terminal disclaimer.

(21) Appl. No.: 10/581,175

(22) PCT Filed: Dec. 9, 2004

(86) PCT No.: PCT/IB2004/004114
§ 371 (c)(1),
(2), (4) Date: Oct. 7, 2008

(87) PCT Pub. No.: WO2005/058897
PCT Pub. Date: Jun. 30, 2005

(65) Prior Publication Data
US 2009/0042921 A1 Feb. 12, 2009

(30) Foreign Application Priority Data
Dec. 12, 2003 (GB) .................. 0328908.9

(51) Int. Cl.
*A61K 31/438* (2006.01)
*C07D 401/04* (2006.01)
(52) U.S. Cl. .................. 514/278; 546/18
(58) Field of Classification Search ........... 546/18; 514/270, 278
See application file for complete search history.

(56) References Cited

U.S. PATENT DOCUMENTS
4,307,235 A * 12/1981 Ong et al. ............. 546/17
5,536,716 A * 7/1996 Chen et al. ............ 514/215

FOREIGN PATENT DOCUMENTS
| | | | |
|---|---|---|---|
| EP | 0286346 A | | 10/1988 |
| GB | 1575800 | * | 10/1998 |
| JP | 2006501170 T | | 1/2006 |
| JP | 2007502253 T | | 2/2007 |
| WO | 9429309 A | | 12/1994 |
| WO | 9825605 A | | 6/1998 |
| WO | 9828297 A | | 7/1998 |
| WO | 9964002 A | | 12/1999 |
| WO | 03106457 A | | 12/2003 |
| WO | WO 03106457 A1 | | 12/2003 |
| WO | WO 2005016884 A1 | | 2/2005 |

OTHER PUBLICATIONS

Meng-Hsin Chen 1996, 37(30) Free Radical method for the synthesis of spiro-piperidinyl heterocycles.*
Ono Keilichi 1978, English Abstract DN 89:129425, ( GB 1575800)1978.*
Caplus abstract DN 46:57358, Kretz E et al. 1952.*
English translation of Japanese Office Action (Appln. No. 2006-543660) mailing date: Jan. 25, 2011.
Kawasaki T et al: "Enantioselective total synthesis of (−)-pseudophrynaminol through tandem olefination, isomerization & asymmetric claisen rearrangement". Tetrahedron Letters, Elsevier Science Publishers, 2003, vol. 44, No. 8, pp. 1591-1593, p. 1592, Compound 12.

* cited by examiner

*Primary Examiner* — Rita Desai
(74) *Attorney, Agent, or Firm* — William A. Teoli, Jr.

(57) ABSTRACT

An insecticidal compound of formula (I), wherein Y is a single bond, C=O, C=S or S(O)$_m$ where m is 0, 1 or 2; $R^1$, $R^2$, $R^3$, $R^4$, $R^8$ $A_1$, $A_2$, A3, $A_4$, $B_1$, $B_2$, $B_3$ and $B_4$ are specified organic groups or salts or N-oxides thereof; compositions containing them and their using in controlling insects, acarines, nematodes or molluscs.

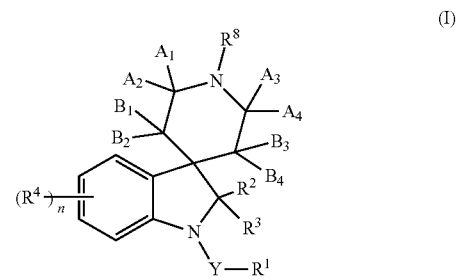

(I)

15 Claims, No Drawings

SPIROINDOLINE DERIVATIVES HAVING INSECTICIDAL PROPERTIES

This application is a 371 of International Application No. PCT/IB2004/004114 filed Dec. 9, 2004, which claims priority to GB 0328908.9 filed Dec. 12, 2003, the contents of which are incorporated herein by reference.

The present invention relates to spiroindoline derivatives, to processes for preparing them, to insecticidal, acaricidal, molluscicidal and nematicidal compositions comprising them and to methods of using them to combat and control insect, acarine, mollusc and nematode pests.

Spiroindoline derivatives with pharmaceutical properties are disclosed in for example WO9825605, WO9429309, WO9828297 and WO9964002. Synthetic routes to selected compounds with pharmaceutical properties are described in Proc. Natl. Acad. Sci. USA (1995), 92, 7001, Tetrahedron (1997), 53, 10983 and Tetrahedron Letters (1997), 38, 1497. It has now surprisingly been found that certain spiroindolines have insecticidal properties.

The present invention therefore provides a compound of formula (I):

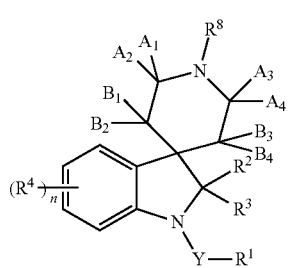

wherein Y is a single bond, C=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group $—N=C(R^{16})—NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4;

$R^8$ is optionally substituted alkyl optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; $A_1$, $A_2$, $A_3$, $A_4$, $B_1$, $B_2$, $B_3$ and $B_4$ are independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl ($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or $A_1$ and $A_2$ together are =O,
or $A_3$ and $A_4$ together are =O,
or $B_1$ and $B_2$ together are =O,
or $B_3$ and $B_4$ together are =O,
or $A_1$ together with $B_1$ is a bond,
or $A_3$ together with $B_3$ is a bond,
or $A_1$ together with $A_2$ form with the carbon to which they are bound a three- to seven-membered ring, and may be saturated or unsaturated, and that may contain one or two hetero atoms selected from the group consisting of N, O and S, and which may be optionally substituted by one or two $C_{1-6}$ alkyl groups;
or $A_1$ together with $B_1$ form with the carbon to which they are bound a three- to seven-membered ring, and may be saturated or unsaturated, and that may contain one or two hetero atoms selected from the group consisting of N, O and S, and which may be optionally substituted by one or two $C_{1-6}$ alkyl groups;
or $B_1$ together with $B_2$ form with the carbon to which they are bound a three- to seven-membered ring, and may be saturated or unsaturated, and that may contain one or two hetero atoms selected from the group consisting of N, O and S, and which may be optionally substituted by one or two $C_{1-6}$ alkyl groups;

or $A_1$ together with $A_3$ form a group —$CH_2$—, —CH=CH— or —$CH_2CH_2$—;

or $B_1$ together with $B_3$ form a group —$CH_2$—, —CH=CH— or —$CH_2CH_2$—;

or salts or N-oxides thereof provided that when $B_1$, $B_2$, $B_3$ and $B_4$ are all H, either both $A_1$ and $A_2$ are different from H or both $A_3$ and $A_4$ are different from H.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{10}$ alkoxycarbonyl, aminocarbonyl, $C_{1-6}$ alkylaminocarbonyl, di($C_{1-6}$ alkyl) aminocarbonyl, N—($C_{1-3}$ alkyl)-N—($C_{1-3}$ alkoxy) aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the beterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$) alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy $(C_{1-10})$alkoxy, tri$(C_{1-4})$alkyl-silyl$(C_{1-6})$alkoxy, $C_{1-6}$ alkoxycarbonyl$(C_{1-10})$alkoxy, $C_{1-10}$ haloalkoxy, aryl$(C_{1-4})$alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl$(C_{1-4})$alkylthio $C_{3-7}$ cycloalkylthio (where the cycloalkyl group is optionally substituted with $C_{1-6}$ alkyl or halogen), tri$(C_{1-4})$-alkylsilyl$(C_{1-6})$alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri$(C_{1-4})$alkylsilyl, aryldi$(C_{1-4})$-alkylsilyl, $(C_{1-4})$alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di$(C_{1-6}$ alkyl)-aminocarbonyl, N—$(C_{1-3}$ alkyl)-N—$(C_{1-3}$ alkoxy)aminocarbonyl, $C_{1-6}$ alkylcarbonyloxy, arylcarbonyloxy, di$(C_{1-6})$alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di$(C_{1-6})$alkylamino, $C_{1-6}$ alkylcarbonylamino, N—$(C_{1-6})$alkylcarbonyl-N—$(C_{1-6})$ alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), $(C_{1-6})$alkyloxycarbonylamino $(C_{1-6})$alkyloxycarbonyl-N—$(C_{1-6})$alkylamino, aryloxycarbonylamino (where the aryl group is substituted by $C_{1-6}$ alkyl or halogen), aryloxycarbonyl-N—$(C_{1-6})$alkylamino, (where the aryl group is substituted by $C_{1-6}$ alkyl or halogen), arylsulphonylamino (where the aryl group is substituted by $C_{1-6}$ alkyl or halogen), arylsulphonyl-N—$(C_{1-6})$alkylamino (where the aryl group is substituted by $C_{1-6}$ alkyl or halogen), aryl-N—$(C_{1-6})$alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di$(C_{1-6})$alkylaminocarbonyl amino, arylaminocarbonyl amino where the aryl group is substituted by $C_{1-6}$ alkyl or halogen), aryl-N—$(C_{1-6})$alkylaminocarbonylamino where the aryl group is substituted by $C_{1-6}$ alkyl or halogen), $C_{1-6}$ alkylaminocarbonyl-N—$(C_{1-6})$alkyl amino, di$(C_{1-6})$alkylaminocarbonyl-N—$(C_{1-6})$alkyl amino, arylaminocarbonyl-N—$(C_{1-6})$alkyl amino where the aryl group is substituted by $C_{1-6}$ alkyl or halogen) and aryl-N—$(C_{1-6})$alkylaminocarbonyl-N—$(C_{1-6})$alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected $(C_{1-6})$alkyl groups. When heterocyclic rings are formed by joining two groups on an N atom, the resulting rings are suitably pyrrolidine, piperidine, thiomorpholine and morpholine each of which may be substituted by one or two independently selected $(C_{1-6})$alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl $(C_{1-4})$alkoxy, $C_{1-10}$ alkylthio, $C_{1-10}$ alkylcarbonyl, $C_{1-10}$ alkoxycarbonyl, $C_{1-6}$ alkylaminocarbonyl, di$(C_{1-6}$ alkyl)aminocarbonyl, $(C_{1-6})$alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with $(C_{1-6})$alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri$(C_{1-4})$alkylsilyl, tri$(C_{1-4})$alkylsilyl$(C_{1-6})$alkoxy, aryldi$(C_{1-4})$alkylsilyl, $(C_{1-4})$alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferably Y is a single bond, C=O or $S(O)_m$ where m is 0, 1 or 2.

More preferably Y is a single bond, C=O or $SO_2$.

Yet more preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl$(C_{1-4})$alkyl, $C_{1-6}$ alkoxy$(C_{1-6})$alkyl, heteroaryl$(C_{1-6})$alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl$(C_{1-6})$alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino$(C_{1-6})$alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$-haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-16}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^2$ and $R^3$ are independently hydrogen, $C_{1-6}$ alkyl, $C_{1-6}$ haloalkyl, $C_{1-6}$ alkoxy or cyano.

More preferably $R^2$ and $R^3$ are independently hydrogen, halogen, $C_{1-2}$ alkyl, $C_{1-2}$ haloalkyl, $C_{1-2}$ alkoxy, cyano.

Even more preferably $R^2$ and $R^3$ are independently hydrogen or $C_{1-4}$ alkyl.

Yet more preferably $R^2$ and $R^3$ are independently hydrogen or methyl.

Most preferably $R^2$ and $R^3$ are both hydrogen.

Preferably each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$)alkyl, $C_{3-7}$ cycloalkyl($C_{1-6}$)alkyl, $C_{5-6}$ cycloalkenyl($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$) alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$) alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl($C_{3-7}$)cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocylic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2.

Most preferably each $R^4$ is independently fluoro, chloro, bromo, $C_{1-4}$ alkyl or $C_{1-4}$ haloalkyl; n is 1 or 2.

Preferably $R^8$ is $C_{1-10}$ alkyl, $C_{1-10}$ haloalkyl, aryl($C_{1-6}$) alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), or $-C(R^{51})(R^{52})-[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), phenyl ($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, or $-C(R^{51})(R^{52})-[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is —$C(R^{51})(R^{52})$—$[CR^{53}$=$CR^{54}]z$-$R^{55}$ where z is 1 or 2, preferably 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably $A_1$, $A_2$, $A_3$, $A_4$, $B_1$, $B_2$, $B_3$ and $B_4$ are independently each hydrogen, halo, cyano, $C_{1-3}$ alkyl, hydroxy or two groups attached to the same carbon atom together with the carbon atom form a carbonyl group.

More preferably $A_1$, $A_2$, $A_3$, $A_4$, $B_1$, $B_2$, $B_3$ and $B_4$ are independently hydrogen, fluoro, methyl, hydroxy or two groups or two groups attached to the same carbon atom together with the carbon atom form a carbonyl group.

One group of preferred compounds of formula (I) are those where Y is C(O) and $R^1$ is $NR^{13}R^{14}$ where $R^{13}$ and $R^{14}$ are as defined above.

The compounds in Tables I to MCLXVII below illustrate the compounds of the invention.

Table I provides 782 compounds of formula Ia

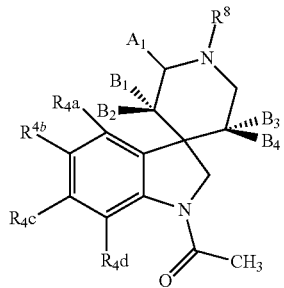

(Ia)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1

TABLE 1

| Compound No | $R^8$ | $R^{4a}$ | $R^{4b}$ | $R^{4c}$ | $R^{4d}$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |

TABLE 1-continued

| Compound No | R⁸ | R⁴ᵃ | R⁴ᵇ | R⁴ᶜ | R⁴ᵈ |
|---|---|---|---|---|---|
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnamyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | Br | H | H |
| I-71 | Cinnamyl | H | Br | H | H |
| I-72 | 4-chlorocinnamyl | H | Br | H | H |
| I-73 | 4-fluorocinnamyl | H | Br | H | H |
| I-74 | 4-bromocinnamyl | H | Br | H | H |
| I-75 | 4-trifluoromethylcinnamyl | H | Br | H | H |
| I-76 | 4-trifluoromethoxycinnamyl | H | Br | H | H |
| I-77 | 4-pentafluoroethoxycinnamyl | H | Br | H | H |
| I-78 | 4-methoxycinnamyl | H | Br | H | H |
| I-79 | 4-ethoxycinnamyl | H | Br | H | H |
| I-80 | 4-cyanocinnamyl | H | Br | H | H |
| I-81 | 3-(6-chloro-pyridin-3-yl)-allyl | H | Br | H | H |
| I-82 | 3-(4-chlorophenyl)-but-2-enyl | H | Br | H | H |
| I-83 | 3-(4-chlorophenyl)-3-fluoro-allyl | H | Br | H | H |
| I-84 | 3-chloro-4-fluoro-cinnamyl | H | Br | H | H |
| I-85 | 3,5-dichloro-cinnamyl | H | Br | H | H |
| I-86 | 5-phenyl-penta-2,4-dienyl | H | Br | H | H |
| I-87 | 4-isopropyloxycarbonylamino-cinnamyl | H | Br | H | H |
| I-88 | 3-naphthalen-2-yl-allyl | H | Br | H | H |
| I-89 | 3-(5-trifluoromethyl-pyridin-2-yl)-allyl | H | Br | H | H |
| I-90 | 3-(5-chloro-pyridin-2-yl)-allyl | H | Br | H | H |
| I-91 | 3-pyridin-4-yl-allyl | H | Br | H | H |
| I-92 | 3-(2-Chloro-pyridin-4-yl)-allyl | H | Br | H | H |
| I-93 | 4-chlorobenzyl | H | CN | H | H |
| I-94 | Cinnamyl | H | CN | H | H |
| I-95 | 4-chlorocinnamyl | H | CN | H | H |
| I-96 | 4-fluorocinnamyl | H | CN | H | H |
| I-97 | 4-bromocinnamyl | H | CN | H | H |
| I-98 | 4-trifluoromethylcinnamyl | H | CN | H | H |
| I-99 | 4-trifluoromethoxycinnamyl | H | CN | H | H |
| I-100 | 4-pentafluoroethoxycinnamyl | H | CN | H | H |
| I-101 | 4-methoxycinnamyl | H | CN | H | H |
| I-102 | 4-ethoxycinnamyl | H | CN | H | H |
| I-103 | 4-cyanocinnamyl | H | CN | H | H |
| I-104 | 3-(6-chloro-pyridin-3-yl)-allyl | H | CN | H | H |
| I-105 | 3-(4-chlorophenyl)-but-2-enyl | H | CN | H | H |
| I-106 | 3-(4-chlorophenyl)-3-fluoro-allyl | H | CN | H | H |
| I-107 | 3-chloro-4-fluoro-cinnamyl | H | CN | H | H |
| I-108 | 3,5-dichloro-cinnamyl | H | CN | H | H |
| I-109 | 5-phenyl-penta-2,4-dienyl | H | CN | H | H |
| I-110 | 4-isopropyloxycarbonylamino-cinnamyl | H | CN | H | H |
| I-111 | 3-naphthalen-2-yl-allyl | H | CN | H | H |
| I-112 | 3-(5-trifluoromethyl-pyridin-2-yl)-allyl | H | CN | H | H |
| I-113 | 3-(5-chloro-pyridin-2-yl)-allyl | H | CN | H | H |
| I-114 | 3-pyridin-4-yl-allyl | H | CN | H | H |
| I-115 | 3-(2-Chloro-pyridin-4-yl)-allyl | H | CN | H | H |
| I-116 | 4-chlorobenzyl | H | OMe | H | H |
| I-117 | Cinnamyl | H | OMe | H | H |
| I-118 | 4-chlorocinnamyl | H | OMe | H | H |
| I-119 | 4-fluorocinnamyl | H | OMe | H | H |
| I-120 | 4-bromocinnamyl | H | OMe | H | H |
| I-121 | 4-trifluoromethylcinnamyl | H | OMe | H | H |
| I-122 | 4-trifluoromethoxycinnamyl | H | OMe | H | H |
| I-123 | 4-pentafluoroethoxycinnamyl | H | OMe | H | H |

TABLE 1-continued

| Compound No | $R^8$ | $R^{4a}$ | $R^{4b}$ | $R^{4c}$ | $R^{4d}$ |
|---|---|---|---|---|---|
| I-124 | 4-methoxycinnamyl | H | OMe | H | H |
| I-125 | 4-ethoxycinnamyl | H | OMe | H | H |
| I-126 | 4-cyanocinnamyl | H | OMe | H | H |
| I-127 | 3-(6-chloro-pyridin-3-yl)-allyl | H | OMe | H | H |
| I-128 | 3-(4-chlorophenyl)-but-2-enyl | H | OMe | H | H |
| I-129 | 3-(4-chlorophenyl)-3-fluoro-allyl | H | OMe | H | H |
| I-130 | 3-chloro-4-fluoro-cinnamyl | H | OMe | H | H |
| I-131 | 3,5-dichloro-cinnamyl | H | OMe | H | H |
| I-132 | 5-phenyl-penta-2,4-dienyl | H | OMe | H | H |
| I-133 | 4-isopropyloxycarbonylamino-cinnamyl | H | OMe | H | H |
| I-134 | 3-naphthalen-2-yl-allyl | H | OMe | H | H |
| I-135 | 3-(5-trifluoromethyl-pyridin-2-yl)-allyl | H | OMe | H | H |
| I-136 | 3-(5-chloro-pyridin-2-yl)-allyl | H | OMe | H | H |
| I-137 | 3-pyridin-4-yl-allyl | H | OMe | H | H |
| I-138 | 3-(2-Chloro-pyridin-4-yl)-allyl | H | OMe | H | H |
| I-139 | 4-chlorobenzyl | H | $OCF_3$ | H | H |
| I-140 | Cinnamyl | H | $OCF_3$ | H | H |
| I-141 | 4-chlorocinnamyl | H | $OCF_3$ | H | H |
| I-142 | 4-fluorocinnamyl | H | $OCF_3$ | H | H |
| I-143 | 4-bromocinnamyl | H | $OCF_3$ | H | H |
| I-144 | 4-trifluoromethylcinnamyl | H | $OCF_3$ | H | H |
| I-145 | 4-trifluoromethoxycinnamyl | H | $OCF_3$ | H | H |
| I-146 | 4-pentafluoroethoxycinnamyl | H | $OCF_3$ | H | H |
| I-147 | 4-methoxycinnamyl | H | $OCF_3$ | H | H |
| I-148 | 4-ethoxycinnamyl | H | $OCF_3$ | H | H |
| I-149 | 4-cyanocinnamyl | H | $OCF_3$ | H | H |
| I-150 | 3-(6-chloro-pyridin-3-yl)-allyl | H | $OCF_3$ | H | H |
| I-151 | 3-(4-chlorophenyl)-but-2-enyl | H | $OCF_3$ | H | H |
| I-152 | 3-(4-chlorophenyl)-3-fluoro-allyl | H | $OCF_3$ | H | H |
| I-153 | 3-chloro-4-fluoro-cinnamyl | H | $OCF_3$ | H | H |
| I-154 | 3,5-dichloro-cinnamyl | H | $OCF_3$ | H | H |
| I-155 | 5-phenyl-penta-2,4-dienyl | H | $OCF_3$ | H | H |
| I-156 | 4-isopropyloxycarbonylamino-cinnamyl | H | $OCF_3$ | H | H |
| I-157 | 3-naphthalen-2-yl-allyl | H | $OCF_3$ | H | H |
| I-158 | 3-(5-trifluoromethyl-pyridin-2-yl)-allyl | H | $OCF_3$ | H | H |
| I-159 | 3-(5-chloro-pyridin-2-yl)-allyl | H | $OCF_3$ | H | H |
| I-160 | 3-pyridin-4-yl-allyl | H | $OCF_3$ | H | H |
| I-161 | 3-(2-Chloro-pyridin-4-yl)-allyl | H | $OCF_3$ | H | H |
| I-162 | 4-chlorobenzyl | H | $CH_3$ | H | H |
| I-163 | Cinnamyl | H | $CH_3$ | H | H |
| I-164 | 4-chlorocinnamyl | H | $CH_3$ | H | H |
| I-165 | 4-fluorocinnamyl | H | $CH_3$ | H | H |
| I-166 | 4-bromocinnamyl | H | $CH_3$ | H | H |
| I-167 | 4-trifluoromethylcinnamyl | H | $CH_3$ | H | H |
| I-168 | 4-trifluoromethoxycinnamyl | H | $CH_3$ | H | H |
| I-169 | 4-pentafluoroethoxycinnamyl | H | $CH_3$ | H | H |
| I-170 | 4-methoxycinnamyl | H | $CH_3$ | H | H |
| I-171 | 4-ethoxycinnamyl | H | $CH_3$ | H | H |
| I-172 | 4-cyanocinnamyl | H | $CH_3$ | H | H |
| I-173 | 3-(6-chloro-pyridin-3-yl)-allyl | H | $CH_3$ | H | H |
| I-174 | 3-(4-chlorophenyl)-but-2-enyl | H | $CH_3$ | H | H |
| I-175 | 3-(4-chlorophenyl)-3-fluoro-allyl | H | $CH_3$ | H | H |
| I-176 | 3-chloro-4-fluoro-cinnamyl | H | $CH_3$ | H | H |
| I-177 | 3,5-dichloro-cinnamyl | H | $CH_3$ | H | H |
| I-178 | 5-phenyl-penta-2,4-dienyl | H | $CH_3$ | H | H |
| I-179 | 4-isopropyloxycarbonylamino-cinnamyl | H | $CH_3$ | H | H |
| I-180 | 3-naphthalen-2-yl-allyl | H | $CH_3$ | H | H |
| I-181 | 3-(5-trifluoromethyl-pyridin-2-yl)-allyl | H | $CH_3$ | H | H |
| I-182 | 3-(5-chloro-pyridin-2-yl)-allyl | H | $CH_3$ | H | H |
| I-183 | 3-pyridin-4-yl-allyl | H | $CH_3$ | H | H |
| I-184 | 3-(2-Chloro-pyridin-4-yl)-allyl | H | $CH_3$ | H | H |
| I-185 | 4-chlorobenzyl | H | $CF_3$ | H | H |
| I-186 | Cinnamyl | H | $CF_3$ | H | H |
| I-187 | 4-chlorocinnamyl | H | $CF_3$ | H | H |
| I-188 | 4-fluorocinnamyl | H | $CF_3$ | H | H |
| I-189 | 4-bromocinnamyl | H | $CF_3$ | H | H |
| I-190 | 4-trifluoromethylcinnamyl | H | $CF_3$ | H | H |
| I-191 | 4-trifluoromethoxycinnamyl | H | $CF_3$ | H | H |
| I-192 | 4-pentafluoroethoxycinnamyl | H | $CF_3$ | H | H |
| I-193 | 4-methoxycinnamyl | H | $CF_3$ | H | H |
| I-194 | 4-ethoxycinnamyl | H | $CF_3$ | H | H |
| I-195 | 4-cyanocinnamyl | H | $CF_3$ | H | H |
| I-196 | 3-(6-chloro-pyridin-3-yl)-allyl | H | $CF_3$ | H | H |
| I-197 | 3-(4-chlorophenyl)-but-2-enyl | H | $CF_3$ | H | H |
| I-198 | 3-(4-chlorophenyl)-3-fluoro-allyl | H | $CF_3$ | H | H |
| I-199 | 3-chloro-4-fluoro-cinnamyl | H | $CF_3$ | H | H |
| I-200 | 3,5-dichloro-cinnamyl | H | $CF_3$ | H | H |

TABLE 1-continued

| Compound No | $R^8$ | $R^{4a}$ | $R^{4b}$ | $R^{4c}$ | $R^{4d}$ |
|---|---|---|---|---|---|
| I-201 | 5-phenyl-penta-2,4-dienyl | H | $CF_3$ | H | H |
| I-202 | 4-isopropyloxycarbonylamino-cinnamyl | H | $CF_3$ | H | H |
| I-203 | 3-naphthalen-2-yl-allyl | H | $CF_3$ | H | H |
| I-204 | 3-(5-trifluoromethyl-pyridin-2-yl)-allyl | H | $CF_3$ | H | H |
| I-205 | 3-(5-chloro-pyridin-2-yl)-allyl | H | $CF_3$ | H | H |
| I-206 | 3-pyridin-4-yl-allyl | H | $CF_3$ | H | H |
| I-207 | 3-(2-Chloro-pyridin-4-yl)-allyl | H | $CF_3$ | H | H |
| I-208 | 4-chlorobenzyl | H | H | Cl | H |
| I-209 | Cinnamyl | H | H | Cl | H |
| I-210 | 4-chlorocinnamyl | H | H | Cl | H |
| I-211 | 4-fluorocinnamyl | H | H | Cl | H |
| I-212 | 4-bromocinnamyl | H | H | Cl | H |
| I-213 | 4-trifluoromethylcinnamyl | H | H | Cl | H |
| I-214 | 4-trifluoromethoxycinnamyl | H | H | Cl | H |
| I-215 | 4-pentafluoroethoxycinnamyl | H | H | Cl | H |
| I-216 | 4-methoxycinnamyl | H | H | Cl | H |
| I-217 | 4-ethoxycinnamyl | H | H | Cl | H |
| I-218 | 4-cyanocinnamyl | H | H | Cl | H |
| I-219 | 3-(6-chloro-pyridin-3-yl)-allyl | H | H | Cl | H |
| I-220 | 3-(4-chlorophenyl)-but-2-enyl | H | H | Cl | H |
| I-221 | 3-(4-chlorophenyl)-3-fluoro-allyl | H | H | Cl | H |
| I-222 | 3-chloro-4-fluoro-cinnamyl | H | H | Cl | H |
| I-223 | 3,5-dichloro-cinnamyl | H | H | Cl | H |
| I-224 | 5-phenyl-penta-2,4-dienyl | H | H | Cl | H |
| I-225 | 4-isopropyloxycarbonylamino-cinnamyl | H | H | Cl | H |
| I-226 | 3-naphthalen-2-yl-allyl | H | H | Cl | H |
| I-227 | 3-(5-trifluoromethyl-pyridin-2-yl)-allyl | H | H | Cl | H |
| I-228 | 3-(5-chloro-pyridin-2-yl)-allyl | H | H | Cl | H |
| I-229 | 3-pyridin-4-yl-allyl | H | H | Cl | H |
| I-230 | 3-(2-Chloro-pyridin-4-yl)-allyl | H | H | Cl | H |
| I-231 | 4-chlorobenzyl | H | H | F | H |
| I-232 | Cinnamyl | H | H | F | H |
| I-233 | 4-chlorocinnamyl | H | H | F | H |
| I-234 | 4-fluorocinnamyl | H | H | F | H |
| I-235 | 4-bromocinnamyl | H | H | F | H |
| I-236 | 4-trifluoromethylcinnamyl | H | H | F | H |
| I-237 | 4-trifluoromethoxycinnamyl | H | H | F | H |
| I-238 | 4-pentafluoroethoxycinnamyl | H | H | F | H |
| I-239 | 4-methoxycinnamyl | H | H | F | H |
| I-240 | 4-ethoxycinnamyl | H | H | F | H |
| I-241 | 4-cyanocinnamyl | H | H | F | H |
| I-242 | 3-(6-chloro-pyridin-3-yl)-allyl | H | H | F | H |
| I-243 | 3-(4-chlorophenyl)-but-2-enyl | H | H | F | H |
| I-244 | 3-(4-chlorophenyl)-3-fluoro-allyl | H | H | F | H |
| I-245 | 3-chloro-4-fluoro-cinnamyl | H | H | F | H |
| I-246 | 3,5-dichloro-cinnamyl | H | H | F | H |
| I-247 | 5-phenyl-penta-2,4-dienyl | H | H | F | H |
| I-248 | 4-isopropyloxycarbonylamino-cinnamyl | H | H | F | H |
| I-249 | 3-naphthalen-2-yl-allyl | H | H | F | H |
| I250 | 3-(5-trifluoromethyl-pyridin-2-yl)-allyl | H | H | F | H |
| I-251 | 3-(5-chloro-pyridin-2-yl)-allyl | H | H | F | H |
| I-252 | 3-pyridin-4-yl-allyl | H | H | F | H |
| I-253 | 3-(2-Chloro-pyridin-4-yl)-allyl | H | H | F | H |
| I-254 | 4-chlorobenzyl | H | H | Br | H |
| I-255 | Cinnamyl | H | H | Br | H |
| I-256 | 4-chlorocinnamyl | H | H | Br | H |
| I-257 | 4-fluorocinnamyl | H | H | Br | H |
| I-258 | 4-bromocinnamyl | H | H | Br | H |
| I-259 | 4-trifluoromethylcinnamyl | H | H | Br | H |
| I-260 | 4-trifluoromethoxycinnamyl | H | H | Br | H |
| I-261 | 4-pentafluoroethoxycinnamyl | H | H | Br | H |
| I-262 | 4-methoxycinnamyl | H | H | Br | H |
| I-263 | 4-ethoxycinnamyl | H | H | Br | H |
| I-264 | 4-cyanocinnamyl | H | H | Br | H |
| I-265 | 3-(6-chloro-pyridin-3-yl)-allyl | H | H | Br | H |
| I-266 | 3-(4-chlorophenyl)-but-2-enyl | H | H | Br | H |
| I-267 | 3-(4-chlorophenyl)-3-fluoro-allyl | H | H | Br | H |
| I-268 | 3-chloro-4-fluoro-cinnamyl | H | H | Br | H |
| I-269 | 3,5-dichloro-cinnamyl | H | H | Br | H |
| I-270 | 5-phenyl-penta-2,4-dienyl | H | H | Br | H |
| I-271 | 4-isopropyloxycarbonylamino-cinnamyl | H | H | Br | H |
| I-272 | 3-naphthalen-2-yl-allyl | H | H | Br | H |
| I-273 | 3-(5-trifluoromethyl-pyridin-2-yl)-allyl | H | H | Br | H |
| I-274 | 3-(5-chloro-pyridin-2-yl)-allyl | H | H | Br | H |
| I-275 | 3-pyridin-4-yl-allyl | H | H | Br | H |
| I-276 | 3-(2-Chloro-pyridin-4-yl)-allyl | H | H | Br | H |
| I-277 | 4-chlorobenzyl | H | H | $OCF_3$ | H |

TABLE 1-continued

| Compound No | R⁸ | R⁴ᵃ | R⁴ᵇ | R⁴ᶜ | R⁴ᵈ |
|---|---|---|---|---|---|
| I-278 | Cinnamyl | H | H | OCF₃ | H |
| I-279 | 4-chlorocinnamyl | H | H | OCF₃ | H |
| I-280 | 4-fluorocinnamyl | H | H | OCF₃ | H |
| I-281 | 4-bromocinnamyl | H | H | OCF₃ | H |
| I-282 | 4-trifluoromethylcinnamyl | H | H | OCF₃ | H |
| I-283 | 4-trifluoromethoxycinnamyl | H | H | OCF₃ | H |
| I-284 | 4-pentafluoroethoxycinnamyl | H | H | OCF₃ | H |
| I-285 | 4-methoxycinnamyl | H | H | OCF₃ | H |
| I-286 | 4-ethoxycinnamyl | H | H | OCF₃ | H |
| I-287 | 4-cyanocinnamyl | H | H | OCF₃ | H |
| I-288 | 3-(6-chloro-pyridin-3-yl)-allyl | H | H | OCF₃ | H |
| I-289 | 3-(4-chlorophenyl)-but-2-enyl | H | H | OCF₃ | H |
| I-290 | 3-(4-chlorophenyl)-3-fluoro-allyl | H | H | OCF₃ | H |
| I-291 | 3-chloro-4-fluoro-cinnamyl | H | H | OCF₃ | H |
| I-292 | 3,5-dichloro-cinnamyl | H | H | OCF₃ | H |
| I-293 | 5-phenyl-penta-2,4-dienyl | H | H | OCF₃ | H |
| I-294 | 4-isopropyloxycarbonylamino-cinnamyl | H | H | OCF₃ | H |
| I-295 | 3-naphthalen-2-yl-allyl | H | H | OCF₃ | H |
| I-296 | 3-(5-trifluoromethyl-pyridin-2-yl)-allyl | H | H | OCF₃ | H |
| I-297 | 3-(5-chloro-pyridin-2-yl)-allyl | H | H | OCF₃ | H |
| I-298 | 3-pyridin-4-yl-allyl | H | H | OCF₃ | H |
| I-299 | 3-(2-Chloro-pyridin-4-yl)-allyl | H | H | OCF₃ | H |
| I-300 | 4-chlorobenzyl | H | H | CH₃ | H |
| I-301 | Cinnamyl | H | H | CH₃ | H |
| I-302 | 4-chlorocinnamyl | H | H | CH₃ | H |
| I-303 | 4-fluorocinnamyl | H | H | CH₃ | H |
| I-304 | 4-bromocinnamyl | H | H | CH₃ | H |
| I-305 | 4-trifluoromethylcinnamyl | H | H | CH₃ | H |
| I-306 | 4-trifluoromethoxycinnamyl | H | H | CH₃ | H |
| I-307 | 4-pentafluoroethoxycinnamyl | H | H | CH₃ | H |
| I-308 | 4-methoxycinnamyl | H | H | CH₃ | H |
| I-309 | 4-ethoxycinnamyl | H | H | CH₃ | H |
| I-310 | 4-cyanocinnamyl | H | H | CH₃ | H |
| I-311 | 3-(6-chloro-pyridin-3-yl)-allyl | H | H | CH₃ | H |
| I-312 | 3-(4-chlorophenyl)-but-2-enyl | H | H | CH₃ | H |
| I-313 | 3-(4-chlorophenyl)-3-fluoro-allyl | H | H | CH₃ | H |
| I-314 | 3-chloro-4-fluoro-cinnamyl | H | H | CH₃ | H |
| I-315 | 3,5-dichloro-cinnamyl | H | H | CH₃ | H |
| I-316 | 5-phenyl-penta-2,4-dienyl | H | H | CH₃ | H |
| I-317 | 4-isopropyloxycarbonylamino-cinnamyl | H | H | CH₃ | H |
| I-318 | 3-naphthalen-2-yl-allyl | H | H | CH₃ | H |
| I-319 | 3-(5-trifluoromethyl-pyridin-2-yl)-allyl | H | H | CH₃ | H |
| I-320 | 3-(5-chloro-pyridin-2-yl)-allyl | H | H | CH₃ | H |
| I-321 | 3-pyridin-4-yl-allyl | H | H | CH₃ | H |
| I-322 | 3-(2-Chloro-pyridin-4-yl)-allyl | H | H | CH₃ | H |
| I-323 | 4-chlorobenzyl | H | H | CF₃ | H |
| I-324 | Cinnamyl | H | H | CF₃ | H |
| I-325 | 4-chlorocinnamyl | H | H | CF₃ | H |
| I-326 | 4-fluorocinnamyl | H | H | CF₃ | H |
| I-327 | 4-bromocinnamyl | H | H | CF₃ | H |
| I-328 | 4-trifluoromethylcinnamyl | H | H | CF₃ | H |
| I-329 | 4-trifluoromethoxycinnamyl | H | H | CF₃ | H |
| I-330 | 4-pentafluoroethoxycinnamyl | H | H | CF₃ | H |
| I-331 | 4-methoxycinnamyl | H | H | CF₃ | H |
| I-332 | 4-ethoxycinnamyl | H | H | CF₃ | H |
| I-333 | 4-cyanocinnamyl | H | H | CF₃ | H |
| I-334 | 3-(6-chloro-pyridin-3-yl)-allyl | H | H | CF₃ | H |
| I-335 | 3-(4-chlorophenyl)-but-2-enyl | H | H | CF₃ | H |
| I-336 | 3-(4-chlorophenyl)-3-fluoro-allyl | H | H | CF₃ | H |
| I-337 | 3-chloro-4-fluoro-cinnamyl | H | H | CF₃ | H |
| I-338 | 3,5-dichloro-cinnamyl | H | H | CF₃ | H |
| I-339 | 5-phenyl-penta-2,4-dienyl | H | H | CF₃ | H |
| I-340 | 4-isopropyloxycarbonylamino-cinnamyl | H | H | CF₃ | H |
| I-341 | 3-naphthalen-2-yl-allyl | H | H | CF₃ | H |
| I-342 | 3-(5-trifluoromethyl-pyridin-2-yl)-allyl | H | H | CF₃ | H |
| I-343 | 3-(5-chloro-pyridin-2-yl)-allyl | H | H | CF₃ | H |
| I-344 | 3-pyridin-4-yl-allyl | H | H | CF₃ | H |
| I-345 | 3-(2-Chloro-pyridin-4-yl)-allyl | H | H | CF₃ | H |
| I-346 | 4-chlorobenzyl | F | H | H | H |
| I-347 | Cinnamyl | F | H | H | H |
| I-348 | 4-chlorocinnamyl | F | H | H | H |
| I-349 | 4-fluorocinnamyl | F | H | H | H |
| I-350 | 4-bromocinnamyl | F | H | H | H |
| I-351 | 4-trifluoromethylcinnamyl | F | H | H | H |
| I-352 | 4-trifluoromethoxycinnamyl | F | H | H | H |
| I-353 | 4-pentafluoroethoxycinnamyl | F | H | H | H |
| I-354 | 4-methoxycinnamyl | F | H | H | H |

TABLE 1-continued

| Compound No | R$^8$ | R$^{4a}$ | R$^{4b}$ | R$^{4c}$ | R$^{4d}$ |
|---|---|---|---|---|---|
| I-355 | 4-ethoxycinnamyl | F | H | H | H |
| I-356 | 4-cyanocinnamyl | F | H | H | H |
| I-357 | 3-(6-chloro-pyridin-3-yl)-allyl | F | H | H | H |
| I-358 | 3-(4-chlorophenyl)-but-2-enyl | F | H | H | H |
| I-359 | 3-(4-chlorophenyl)-3-fluoro-allyl | F | H | H | H |
| I-360 | 3-chloro-4-fluoro-cinnamyl | F | H | H | H |
| I-361 | 3,5-dichloro-cinnamyl | F | H | H | H |
| I-362 | 5-phenyl-penta-2,4-dienyl | F | H | H | H |
| I-363 | 4-isopropyloxycarbonylamino-cinnamyl | F | H | H | H |
| I-364 | 3-naphthalen-2-yl-allyl | F | H | H | H |
| I-365 | 3-(5-trifluoromethyl-pyridin-2-yl)-allyl | F | H | H | H |
| I-366 | 3-(5-chloro-pyridin-2-yl)-allyl | F | H | H | H |
| I-367 | 3-pyridin-4-yl-allyl | F | H | H | H |
| I-368 | 3-(2-Chloro-pyridin-4-yl)-allyl | F | H | H | H |
| I-369 | 4-chlorobenzyl | Cl | H | H | H |
| I-370 | Cinnamyl | Cl | H | H | H |
| I-371 | 4-chlorocinnamyl | Cl | H | H | H |
| I-372 | 4-fluorocinnamyl | Cl | H | H | H |
| I-373 | 4-bromocinnamyl | Cl | H | H | H |
| I-374 | 4-trifluoromethylcinnamyl | Cl | H | H | H |
| I-375 | 4-trifluoromethoxycinnamyl | Cl | H | H | H |
| I-376 | 4-pentafluoroethoxycinnamyl | Cl | H | H | H |
| I-377 | 4-methoxycinnamyl | Cl | H | H | H |
| I-378 | 4-ethoxycinnamyl | Cl | H | H | H |
| I-379 | 4-cyanocinnamyl | Cl | H | H | H |
| I-380 | 3-(6-chloro-pyridin-3-yl)-allyl | Cl | H | H | H |
| I-381 | 3-(4-chlorophenyl)-but-2-enyl | Cl | H | H | H |
| I-382 | 3-(4-chlorophenyl)-3-fluoro-allyl | Cl | H | H | H |
| I-383 | 3-chloro-4-fluoro-cinnamyl | Cl | H | H | H |
| I-384 | 3,5-dichloro-cinnamyl | Cl | H | H | H |
| I-385 | 5-phenyl-penta-2,4-dienyl | Cl | H | H | H |
| I-386 | 4-isopropyloxycarbonylamino-cinnamyl | Cl | H | H | H |
| I-387 | 3-naphthalen-2-yl-allyl | Cl | H | H | H |
| I-388 | 3-(5-trifluoromethyl-pyridin-2-yl)-allyl | Cl | H | H | H |
| I-389 | 3-(5-chloro-pyridin-2-yl)-allyl | Cl | H | H | H |
| I-390 | 3-pyridin-4-yl-allyl | Cl | H | H | H |
| I-391 | 3-(2-Chloro-pyridin-4-yl)-allyl | Cl | H | H | H |
| I-392 | 4-chlorobenzyl | Br | H | H | H |
| I-393 | Cinnamyl | Br | H | H | H |
| I-394 | 4-chlorocinnamyl | Br | H | H | H |
| I-395 | 4-fluorocinnamyl | Br | H | H | H |
| I-396 | 4-bromocinnamyl | Br | H | H | H |
| I-397 | 4-trifluoromethylcinnamyl | Br | H | H | H |
| I-398 | 4-trifluoromethoxycinnamyl | Br | H | H | H |
| I-399 | 4-pentafluoroethoxycinnamyl | Br | H | H | H |
| I-400 | 4-methoxycinnamyl | Br | H | H | H |
| I-401 | 4-ethoxycinnamyl | Br | H | H | H |
| I-402 | 4-cyanocinnamyl | Br | H | H | H |
| I-403 | 3-(6-chloro-pyridin-3-yl)-allyl | Br | H | H | H |
| I-404 | 3-(4-chlorophenyl)-but-2-enyl | Br | H | H | H |
| I-405 | 3-(4-chlorophenyl)-3-fluoro-allyl | Br | H | H | H |
| I-406 | 3-chloro-4-fluoro-cinnamyl | Br | H | H | H |
| I-407 | 3,5-dichloro-cinnamyl | Br | H | H | H |
| I-408 | 5-phenyl-penta-2,4-dienyl | Br | H | H | H |
| I-409 | 4-isopropyloxycarbonylamino-cinnamyl | Br | H | H | H |
| I-410 | 3-naphthalen-2-yl-allyl | Br | H | H | H |
| I-411 | 3-(5-trifluoromethyl-pyridin-2-yl)-allyl | Br | H | H | H |
| I-412 | 3-(5-chloro-pyridin-2-yl)-allyl | Br | H | H | H |
| I-413 | 3-pyridin-4-yl-allyl | Br | H | H | H |
| I-414 | 3-(2-Chloro-pyridin-4-yl)-allyl | Br | H | H | H |
| I-415 | 4-chlorobenzyl | CF$_3$ | H | H | H |
| I-416 | Cinnamyl | CF$_3$ | H | H | H |
| I-417 | 4-chlorocinnamyl | CF$_3$ | H | H | H |
| I-418 | 4-fluorocinnamyl | CF$_3$ | H | H | H |
| I-419 | 4-bromocinnamyl | CF$_3$ | H | H | H |
| I-420 | 4-trifluoromethylcinnamyl | CF$_3$ | H | H | H |
| I-421 | 4-trifluoromethoxycinnamyl | CF$_3$ | H | H | H |
| I-422 | 4-pentafluoroethoxycinnamyl | CF$_3$ | H | H | H |
| I-423 | 4-methoxycinnamyl | CF$_3$ | H | H | H |
| I-424 | 4-ethoxycinnamyl | CF$_3$ | H | H | H |
| I-425 | 4-cyanocinnamyl | CF$_3$ | H | H | H |
| I-426 | 3-(6-chloro-pyridin-3-yl)-allyl | CF$_3$ | H | H | H |
| I-427 | 3-(4-chlorophenyl)-but-2-enyl | CF$_3$ | H | H | H |
| I-428 | 3-(4-chlorophenyl)-3-fluoro-allyl | CF$_3$ | H | H | H |
| I-429 | 3-chloro-4-fluoro-cinnamyl | CF$_3$ | H | H | H |
| I-430 | 3,5-dichloro-cinnamyl | CF$_3$ | H | H | H |
| I-431 | 5-phenyl-penta-2,4-dienyl | CF$_3$ | H | H | H |

TABLE 1-continued

| Compound No | R[8] | R[4a] | R[4b] | R[4c] | R[4d] |
|---|---|---|---|---|---|
| I-432 | 4-isopropyloxycarbonylamino-cinnamyl | CF$_3$ | H | H | H |
| I-433 | 3-naphthalen-2-yl-allyl | CF$_3$ | H | H | H |
| I-434 | 3-(5-trifluoromethyl-pyridin-2-yl)-allyl | CF$_3$ | H | H | H |
| I-435 | 3-(5-chloro-pyridin-2-yl)-allyl | CF$_3$ | H | H | H |
| I-436 | 3-pyridin-4-yl-allyl | CF$_3$ | H | H | H |
| I-437 | 3-(2-Chloro-pyridin-4-yl)-allyl | CF$_3$ | H | H | H |
| I-438 | 4-chlorobenzyl | H | H | H | F |
| I-439 | Cinnamyl | H | H | H | F |
| I-440 | 4-chlorocinnamyl | H | H | H | F |
| I-441 | 4-fluorocinnamyl | H | H | H | F |
| I-442 | 4-bromocinnamyl | H | H | H | F |
| I-443 | 4-trifluoromethylcinnamyl | H | H | H | F |
| I-444 | 4-trifluoromethoxycinnamyl | H | H | H | F |
| I-445 | 4-pentafluoroethoxycinnamyl | H | H | H | F |
| I-446 | 4-methoxycinnamyl | H | H | H | F |
| I-447 | 4-ethoxycinnamyl | H | H | H | F |
| I-448 | 4-cyanocinnamyl | H | H | H | F |
| I-449 | 3-(6-chloro-pyridin-3-yl)-allyl | H | H | H | F |
| I-450 | 3-(4-chlorophenyl)-but-2-enyl | H | H | H | F |
| I-451 | 3-(4-chlorophenyl)-3-fluoro-allyl | H | H | H | F |
| I-452 | 3-chloro-4-fluoro-cinnamyl | H | H | H | F |
| I-453 | 3,5-dichloro-cinnamyl | H | H | H | F |
| I-454 | 5-phenyl-penta-2,4-dienyl | H | H | H | F |
| I-455 | 4-isopropyloxycarbonylamino-cinnamyl | H | H | H | F |
| I-456 | 3-naphthalen-2-yl-allyl | H | H | H | F |
| I-457 | 3-(5-trifluoromethyl-pyridin-2-yl)-allyl | H | H | H | F |
| I-458 | 3-(5-chloro-pyridin-2-yl)-allyl | H | H | H | F |
| I-459 | 3-pyridin-4-yl-allyl | H | H | H | F |
| I-460 | 3-(2-Chloro-pyridin-4-yl)-allyl | H | H | H | F |
| I-461 | 4-chlorobenzyl | H | H | H | Cl |
| I-462 | Cinnamyl | H | H | H | Cl |
| I-463 | 4-chlorocinnamyl | H | H | H | Cl |
| I-464 | 4-fluorocinnamyl | H | H | H | Cl |
| I-465 | 4-bromocinnamyl | H | H | H | Cl |
| I-466 | 4-trifluoromethylcinnamyl | H | H | H | Cl |
| I-467 | 4-trifluoromethoxycinnamyl | H | H | H | Cl |
| I-468 | 4-pentafluoroethoxycinnamyl | H | H | H | Cl |
| I-469 | 4-methoxycinnamyl | H | H | H | Cl |
| I-470 | 4-ethoxycinnamyl | H | H | H | Cl |
| I-471 | 4-cyanocinnamyl | H | H | H | Cl |
| I-472 | 3-(6-chloro-pyridin-3-yl)-allyl | H | H | H | Cl |
| I-473 | 3-(4-chlorophenyl)-but-2-enyl | H | H | H | Cl |
| I-474 | 3-(4-chlorophenyl)-3-fluoro-allyl | H | H | H | Cl |
| I-475 | 3-chloro-4-fluoro-cinnamyl | H | H | H | Cl |
| I-476 | 3,5-dichloro-cinnamyl | H | H | H | Cl |
| I-477 | 5-phenyl-penta-2,4-dienyl | H | H | H | Cl |
| I-478 | 4-isopropyloxycarbonylamino-cinnamyl | H | H | H | Cl |
| I-479 | 3-naphthalen-2-yl-allyl | H | H | H | Cl |
| I-480 | 3-(5-trifluoromethyl-pyridin-2-yl)-allyl | H | H | H | Cl |
| I-481 | 3-(5-chloro-pyridin-2-yl)-allyl | H | H | H | Cl |
| I-482 | 3-pyridin-4-yl-allyl | H | H | H | Cl |
| I-483 | 3-(2-Chloro-pyridin-4-yl)-allyl | H | H | H | Cl |
| I-484 | 4-chlorobenzyl | H | F | F | H |
| I-485 | Cinnamyl | H | F | F | H |
| I-486 | 4-chlorocinnamyl | H | F | F | H |
| I-487 | 4-fluorocinnamyl | H | F | F | H |
| I-488 | 4-bromocinnamyl | H | F | F | H |
| I-489 | 4-trifluoromethylcinnamyl | H | F | F | H |
| I-490 | 4-trifluoromethoxycinnamyl | H | F | F | H |
| I-491 | 4-pentafluoroethoxycinnamyl | H | F | F | H |
| I-492 | 4-methoxycinnamyl | H | F | F | H |
| I-493 | 4-ethoxycinnamyl | H | F | F | H |
| I-494 | 4-cyanocinnamyl | H | F | F | H |
| I-495 | 3-(6-chloro-pyridin-3-yl)-allyl | H | F | F | H |
| I-496 | 3-(4-chlorophenyl)-but-2-enyl | H | F | F | H |
| I-497 | 3-(4-chlorophenyl)-3-fluoro-allyl | H | F | F | H |
| I-498 | 3-chloro-4-fluoro-cinnamyl | H | F | F | H |
| I-499 | 3,5-dichloro-cinnamyl | H | F | F | H |
| I-500 | 5-phenyl-penta-2,4-dienyl | H | F | F | H |
| I-501 | 4-isopropyloxycarbonylamino-cinnamyl | H | F | F | H |
| I-502 | 3-naphthalen-2-yl-allyl | H | F | F | H |
| I-503 | 3-(5-trifluoromethyl-pyridin-2-yl)-allyl | H | F | F | H |
| I-504 | 3-(5-chloro-pyridin-2-yl)-allyl | H | F | F | H |
| I-505 | 3-pyridin-4-yl-allyl | H | F | F | H |
| I-506 | 3-(2-Chloro-pyridin-4-yl)-allyl | H | F | F | H |
| I-507 | 4-chlorobenzyl | H | F | Cl | H |
| I-508 | Cinnamyl | H | F | Cl | H |

TABLE 1-continued

| Compound No | R⁸ | R⁴ᵃ | R⁴ᵇ | R⁴ᶜ | R⁴ᵈ |
|---|---|---|---|---|---|
| I-509 | 4-chlorocinnamyl | H | F | Cl | H |
| I-510 | 4-fluorocinnamyl | H | F | Cl | H |
| I-511 | 4-bromocinnamyl | H | F | Cl | H |
| I-512 | 4-trifluoromethylcinnamyl | H | F | Cl | H |
| I-513 | 4-trifluoromethoxycinnamyl | H | F | Cl | H |
| I-514 | 4-pentafluoroethoxycinnamyl | H | F | Cl | H |
| I-515 | 4-methoxycinnamyl | H | F | Cl | H |
| I-516 | 4-ethoxycinnamyl | H | F | Cl | H |
| I-517 | 4-cyanocinnamyl | H | F | Cl | H |
| I-518 | 3-(6-chloro-pyridin-3-yl)-allyl | H | F | Cl | H |
| I-519 | 3-(4-chlorophenyl)-but-2-enyl | H | F | Cl | H |
| I-520 | 3-(4-chlorophenyl)-3-fluoro-allyl | H | F | Cl | H |
| I-521 | 3-chloro-4-fluoro-cinnamyl | H | F | Cl | H |
| I-522 | 3,5-dichloro-cinnamyl | H | F | Cl | H |
| I-523 | 5-phenyl-penta-2,4-dienyl | H | F | Cl | H |
| I-524 | 4-isopropyloxycarbonylamino-cinnamyl | H | F | Cl | H |
| I-525 | 3-naphthalen-2-yl-allyl | H | F | Cl | H |
| I-526 | 3-(5-trifluoromethyl-pyridin-2-yl)-allyl | H | F | Cl | H |
| I-527 | 3-(5-chloro-pyridin-2-yl)-allyl | H | F | Cl | H |
| I-528 | 3-pyridin-4-yl-allyl | H | F | Cl | H |
| I-529 | 3-(2-Chloro-pyridin-4-yl)-allyl | H | F | Cl | H |
| I-530 | 4-chlorobenzyl | H | Cl | F | H |
| I-531 | Cinnamyl | H | Cl | F | H |
| I-532 | 4-chlorocinnamyl | H | Cl | F | H |
| I-533 | 4-fluorocinnamyl | H | Cl | F | H |
| I-534 | 4-bromocinnamyl | H | Cl | F | H |
| I-535 | 4-trifluoromethylcinnamyl | H | Cl | F | H |
| I-536 | 4-trifluoromethoxycinnamyl | H | Cl | F | H |
| I-537 | 4-pentafluoroethoxycinnamyl | H | Cl | F | H |
| I-538 | 4-methoxycinnamyl | H | Cl | F | H |
| I-539 | 4-ethoxycinnamyl | H | Cl | F | H |
| I-540 | 4-cyanocinnamyl | H | Cl | F | H |
| I-541 | 3-(6-chloro-pyridin-3-yl)-allyl | H | Cl | F | H |
| I-542 | 3-(4-chlorophenyl)-but-2-enyl | H | Cl | F | H |
| I-543 | 3-(4-chlorophenyl)-3-fluoro-allyl | H | Cl | F | H |
| I-544 | 3-chloro-4-fluoro-cinnamyl | H | Cl | F | H |
| I-545 | 3,5-dichloro-cinnamyl | H | Cl | F | H |
| I-546 | 5-phenyl-penta-2,4-dienyl | H | Cl | F | H |
| I-547 | 4-isopropyloxycarbonylamino-cinnamyl | H | Cl | F | H |
| I-548 | 3-naphthalen-2-yl-allyl | H | Cl | F | H |
| I-549 | 3-(5-trifluoromethyl-pyridin-2-yl)-allyl | H | Cl | F | H |
| I-550 | 3-(5-chloro-pyridin-2-yl)-allyl | H | Cl | F | H |
| I-551 | 3-pyridin-4-yl-allyl | H | Cl | F | H |
| I-552 | 3-(2-Chloro-pyridin-4-yl)-allyl | H | Cl | F | H |
| I-553 | 4-chlorobenzyl | H | Cl | Cl | H |
| I-554 | Cinnamyl | H | Cl | Cl | H |
| I-555 | 4-chlorocinnamyl | H | Cl | Cl | H |
| I-556 | 4-fluorocinnamyl | H | Cl | Cl | H |
| I-557 | 4-bromocinnamyl | H | Cl | Cl | H |
| I-558 | 4-trifluoromethylcinnamyl | H | Cl | Cl | H |
| I-559 | 4-trifluoromethoxycinnamyl | H | Cl | Cl | H |
| I-560 | 4-pentafluoroethoxycinnamyl | H | Cl | Cl | H |
| I-561 | 4-methoxycinnamyl | H | Cl | Cl | H |
| I-562 | 4-ethoxycinnamyl | H | Cl | Cl | H |
| I-563 | 4-cyanocinnamyl | H | Cl | Cl | H |
| I-564 | 3-(6-chloro-pyridin-3-yl)-allyl | H | Cl | Cl | H |
| I-565 | 3-(4-chlorophenyl)-but-2-enyl | H | Cl | Cl | H |
| I-566 | 3-(4-chlorophenyl)-3-fluoro-allyl | H | Cl | Cl | H |
| I-567 | 3-chloro-4-fluoro-cinnamyl | H | Cl | Cl | H |
| I-568 | 3,5-dichloro-cinnamyl | H | Cl | Cl | H |
| I-569 | 5-phenyl-penta-2,4-dienyl | H | Cl | Cl | H |
| I-570 | 4-isopropyloxycarbonylamino-cinnamyl | H | Cl | Cl | H |
| I-571 | 3-naphthalen-2-yl-allyl | H | Cl | Cl | H |
| I-572 | 3-(5-trifluoromethyl-pyridin-2-yl)-allyl | H | Cl | Cl | H |
| I-573 | 3-(5-chloro-pyridin-2-yl)-allyl | H | Cl | Cl | H |
| I-574 | 3-pyridin-4-yl-allyl | H | Cl | Cl | H |
| I-575 | 3-(2-Chloro-pyridin-4-yl)-allyl | H | Cl | Cl | H |
| I-576 | 4-chlorobenzyl | H | —OCF₂O— | | H |
| I-577 | Cinnamyl | H | —OCF₂O— | | H |
| I-578 | 4-chlorocinnamyl | H | —OCF₂O— | | H |
| I-579 | 4-fluorocinnamyl | H | —OCF₂O— | | H |
| I-580 | 4-bromocinnamyl | H | —OCF₂O— | | H |
| I-581 | 4-trifluoromethylcinnamyl | H | —OCF₂O— | | H |
| I-582 | 4-trifluoromethoxycinnamyl | H | —OCF₂O— | | H |
| I-583 | 4-pentafluoroethoxycinnamyl | H | —OCF₂O— | | H |
| I-584 | 4-methoxycinnamyl | H | —OCF₂O— | | H |
| I-585 | 4-ethoxycinnamyl | H | —OCF₂O— | | H |

TABLE 1-continued

| Compound No | R8 | R4a | R4b | R4c | R4d |
|---|---|---|---|---|---|
| I-586 | 4-cyanocinnamyl | H | —OCF$_2$O— | | H |
| I-587 | 3-(6-chloro-pyridin-3-yl)-allyl | H | —OCF$_2$O— | | H |
| I-588 | 3-(4-chlorophenyl)-but-2-enyl | H | —OCF$_2$O— | | H |
| I-589 | 3-(4-chlorophenyl)-3-fluoro-allyl | H | —OCF$_2$O— | | H |
| I-590 | 3-chloro-4-fluoro-cinnamyl | H | —OCF$_2$O— | | H |
| I-591 | 3,5-dichloro-cinnamyl | H | —OCF$_2$O— | | H |
| I-592 | 5-phenyl-penta-2,4-dienyl | H | —OCF$_2$O— | | H |
| I-593 | 4-isopropyloxycarbonylamino-cinnamyl | H | —OCF$_2$O— | | H |
| I-594 | 3-naphthalen-2-yl-allyl | H | —OCF$_2$O— | | H |
| I-595 | 3-(5-trifluoromethyl-pyridin-2-yl)-allyl | H | —OCF$_2$O— | | H |
| I-596 | 3-(5-chloro-pyridin-2-yl)-allyl | H | —OCF$_2$O— | | H |
| I-597 | 3-pyridin-4-yl-allyl | H | —OCF$_2$O— | | H |
| I-598 | 3-(2-Chloro-pyridin-4-yl)-allyl | H | —OCF$_2$O— | | H |
| I-599 | 4-chlorobenzyl | H | —C$_4$H$_4$— | | H |
| I-600 | Cinnamyl | H | —C$_4$H$_4$— | | H |
| I-601 | 4-chlorocinnamyl | H | —C$_4$H$_4$— | | H |
| I-602 | 4-fluorocinnamyl | H | —C$_4$H$_4$— | | H |
| I-603 | 4-bromocinnamyl | H | —C$_4$H$_4$— | | H |
| I-604 | 4-trifluoromethylcinnamyl | H | —C$_4$H$_4$— | | H |
| I-605 | 4-trifluoromethoxycinnamyl | H | —C$_4$H$_4$— | | H |
| I-606 | 4-pentafluoroethoxycinnamyl | H | —C$_4$H$_4$— | | H |
| I-607 | 4-methoxycinnamyl | H | —C$_4$H$_4$— | | H |
| I-608 | 4-ethoxycinnamyl | H | —C$_4$H$_4$— | | H |
| I-609 | 4-cyanocinnamyl | H | —C$_4$H$_4$— | | H |
| I-610 | 3-(6-chloro-pyridin-3-yl)-allyl | H | —C$_4$H$_4$— | | H |
| I-611 | 3-(4-chlorophenyl)-but-2-enyl | H | —C$_4$H$_4$— | | H |
| I-612 | 3-(4-chlorophenyl)-3-fluoro-allyl | H | —C$_4$H$_4$— | | H |
| I-613 | 3-chloro-4-fluoro-cinnamyl | H | —C$_4$H$_4$— | | H |
| I-614 | 3,5-dichloro-cinnamyl | H | —C$_4$H$_4$— | | H |
| I-615 | 5-phenyl-penta-2,4-dienyl | H | —C$_4$H$_4$— | | H |
| I-616 | 4-isopropyloxycarbonylamino-cinnamyl | H | —C$_4$H$_4$— | | H |
| I-617 | 3-naphthalen-2-yl-allyl | H | —C$_4$H$_4$— | | H |
| I-618 | 3-(5-trifluoromethyl-pyridin-2-yl)-allyl | H | —C$_4$H$_4$— | | H |
| I-619 | 3-(5-chloro-pyridin-2-yl)-allyl | H | —C$_4$H$_4$— | | H |
| I-620 | 3-pyridin-4-yl-allyl | H | —C$_4$H$_4$— | | H |
| I-621 | 3-(2-Chloro-pyridin-4-yl)-allyl | H | —C$_4$H$_4$— | | H |
| I-622 | 4-chlorobenzyl | Cl | H | Cl | H |
| I-623 | Cinnamyl | Cl | H | Cl | H |
| I-624 | 4-chlorocinnamyl | Cl | H | Cl | H |
| I-625 | 4-fluorocinnamyl | Cl | H | Cl | H |
| I-626 | 4-bromocinnamyl | Cl | H | Cl | H |
| I-627 | 4-trifluoromethylcinnamyl | Cl | H | Cl | H |
| I-628 | 4-trifluoromethoxycinnamyl | Cl | H | Cl | H |
| I-629 | 4-pentafluoroethoxycinnamyl | Cl | H | Cl | H |
| I-630 | 4-methoxycinnamyl | Cl | H | Cl | H |
| I-631 | 4-ethoxycinnamyl | Cl | H | Cl | H |
| I-632 | 4-cyanocinnamyl | Cl | H | Cl | H |
| I-633 | 3-(6-chloro-pyridin-3-yl)-allyl | Cl | H | Cl | H |
| I-634 | 3-(4-chlorophenyl)-but-2-enyl | Cl | H | Cl | H |
| I-635 | 3-(4-chlorophenyl)-3-fluoro-allyl | Cl | H | Cl | H |
| I-636 | 3-chloro-4-fluoro-cinnamyl | Cl | H | Cl | H |
| I-637 | 3,5-dichloro-cinnamyl | Cl | H | Cl | H |
| I-638 | 5-phenyl-penta-2,4-dienyl | Cl | H | Cl | H |
| I-639 | 4-isopropyloxycarbonylamino-cinnamyl | Cl | H | Cl | H |
| I-640 | 3-naphthalen-2-yl-allyl | Cl | H | Cl | H |
| I-641 | 3-(5-trifluoromethyl-pyridin-2-yl)-allyl | Cl | H | Cl | H |
| I-642 | 3-(5-chloro-pyridin-2-yl)-allyl | Cl | H | Cl | H |
| I-643 | 3-pyridin-4-yl-allyl | Cl | H | Cl | H |
| I-644 | 3-(2-Chloro-pyridin-4-yl)-allyl | Cl | H | Cl | H |
| I-645 | 4-chlorobenzyl | Cl | Cl | H | H |
| I-646 | Cinnamyl | Cl | Cl | H | H |
| I-647 | 4-chlorocinnamyl | Cl | Cl | H | H |
| I-648 | 4-fluorocinnamyl | Cl | Cl | H | H |
| I-649 | 4-bromocinnamyl | Cl | Cl | H | H |
| I-650 | 4-trifluoromethylcinnamyl | Cl | Cl | H | H |
| I-651 | 4-trifluoromethoxycinnamyl | Cl | Cl | H | H |
| I-652 | 4-pentafluoroethoxycinnamyl | Cl | Cl | H | H |
| I-653 | 4-methoxycinnamyl | Cl | Cl | H | H |
| I-654 | 4-ethoxycinnamyl | Cl | Cl | H | H |
| I-655 | 4-cyanocinnamyl | Cl | Cl | H | H |
| I-656 | 3-(6-chloro-pyridin-3-yl)-allyl | Cl | Cl | H | H |
| I-657 | 3-(4-chlorophenyl)-but-2-enyl | Cl | Cl | H | H |
| I-658 | 3-(4-chlorophenyl)-3-fluoro-allyl | Cl | Cl | H | H |
| I-659 | 3-chloro-4-fluoro-cinnamyl | Cl | Cl | H | H |
| I-660 | 3,5-dichloro-cinnamyl | Cl | Cl | H | H |
| I-661 | 5-phenyl-penta-2,4-dienyl | Cl | Cl | H | H |
| I-662 | 4-isopropyloxycarbonylamino-cinnamyl | Cl | Cl | H | H |

TABLE 1-continued

| Compound No | R⁸ | R⁴ᵃ | R⁴ᵇ | R⁴ᶜ | R⁴ᵈ |
|---|---|---|---|---|---|
| I-663 | 3-naphthalen-2-yl-allyl | Cl | Cl | H | H |
| I-664 | 3-(5-trifluoromethyl-pyridin-2-yl)-allyl | Cl | Cl | H | H |
| I-665 | 3-(5-chloro-pyridin-2-yl)-allyl | Cl | Cl | H | H |
| I-666 | 3-pyridin-4-yl-allyl | Cl | Cl | H | H |
| I-667 | 3-(2-Chloro-pyridin-4-yl)-allyl | Cl | Cl | H | H |
| I-668 | 4-chlorobenzyl | H | Cl | H | Cl |
| I-669 | Cinnamyl | H | Cl | H | Cl |
| I-670 | 4-chlorocinnamyl | H | Cl | H | Cl |
| I-671 | 4-fluorocinnamyl | H | Cl | H | Cl |
| I-672 | 4-bromocinnamyl | H | Cl | H | Cl |
| I-673 | 4-trifluoromethylcinnamyl | H | Cl | H | Cl |
| I-674 | 4-trifluoromethoxycinnamyl | H | Cl | H | Cl |
| I-675 | 4-pentafluoroethoxycinnamyl | H | Cl | H | Cl |
| I-676 | 4-methoxycinnamyl | H | Cl | H | Cl |
| I-677 | 4-ethoxycinnamyl | H | Cl | H | Cl |
| I-678 | 4-cyanocinnamyl | H | Cl | H | Cl |
| I-679 | 3-(6-chloro-pyridin-3-yl)-allyl | H | Cl | H | Cl |
| I-680 | 3-(4-chlorophenyl)-but-2-enyl | H | Cl | H | Cl |
| I-681 | 3-(4-chlorophenyl)-3-fluoro-allyl | H | Cl | H | Cl |
| I-682 | 3-chloro-4-fluoro-cinnamyl | H | Cl | H | Cl |
| I-683 | 3,5-dichloro-cinnamyl | H | Cl | H | Cl |
| I-684 | 5-phenyl-penta-2,4-dienyl | H | Cl | H | Cl |
| I-685 | 4-isopropyloxycarbonylamino-cinnamyl | H | Cl | H | Cl |
| I-686 | 3-naphthalen-2-yl-allyl | H | Cl | H | Cl |
| I-687 | 3-(5-trifluoromethyl-pyridin-2-yl)-allyl | H | Cl | H | Cl |
| I-688 | 3-(5-chloro-pyridin-2-yl)-allyl | H | Cl | H | Cl |
| I-689 | 3-pyridin-4-yl-allyl | H | Cl | H | Cl |
| I-690 | 3-(2-Chloro-pyridin-4-yl)-allyl | H | Cl | H | Cl |
| I-691 | 4-chlorobenzyl | H | F | H | F |
| I-692 | Cinnamyl | H | F | H | F |
| I-693 | 4-chlorocinnamyl | H | F | H | F |
| I-694 | 4-fluorocinnamyl | H | F | H | F |
| I-695 | 4-bromocinnamyl | H | F | H | F |
| I-696 | 4-trifluoromethylcinnamyl | H | F | H | F |
| I-697 | 4-trifluoromethoxycinnamyl | H | F | H | F |
| I-698 | 4-pentafluoroethoxycinnamyl | H | F | H | F |
| I-699 | 4-methoxycinnamyl | H | F | H | F |
| I-700 | 4-ethoxycinnamyl | H | F | H | F |
| I-701 | 4-cyanocinnamyl | H | F | H | F |
| I-702 | 3-(6-chloro-pyridin-3-yl)-allyl | H | F | H | F |
| I-703 | 3-(4-chlorophenyl)-but-2-enyl | H | F | H | F |
| I-704 | 3-(4-chlorophenyl)-3-fluoro-allyl | H | F | H | F |
| I-705 | 3-chloro-4-fluoro-cinnamyl | H | F | H | F |
| I-706 | 3,5-dichloro-cinnamyl | H | F | H | F |
| I-707 | 5-phenyl-penta-2,4-dienyl | H | F | H | F |
| I-708 | 4-isopropyloxycarbonylamino-cinnamyl | H | F | H | F |
| I-709 | 3-naphthalen-2-yl-allyl | H | F | H | F |
| I-710 | 3-(5-trifluoromethyl-pyridin-2-yl)-allyl | H | F | H | F |
| I-711 | 3-(5-chloro-pyridin-2-yl)-allyl | H | F | H | F |
| I-712 | 3-pyridin-4-yl-allyl | H | F | H | F |
| I-713 | 3-(2-Chloro-pyridin-4-yl)-allyl | H | F | H | F |
| I-714 | 4-chlorobenzyl | F | H | F | H |
| I-715 | Cinnamyl | F | H | F | H |
| I-716 | 4-chlorocinnamyl | F | H | F | H |
| I-717 | 4-fluorocinnamyl | F | H | F | H |
| I-718 | 4-bromocinnamyl | F | H | F | H |
| I-719 | 4-trifluoromethylcinnamyl | F | H | F | H |
| I-720 | 4-trifluoromethoxycinnamyl | F | H | F | H |
| I-721 | 4-pentafluoroethoxycinnamyl | F | H | F | H |
| I-722 | 4-methoxycinnamyl | F | H | F | H |
| I-723 | 4-ethoxycinnamyl | F | H | F | H |
| I-724 | 4-cyanocinnamyl | F | H | F | H |
| I-725 | 3-(6-chloro-pyridin-3-yl)-allyl | F | H | F | H |
| I-726 | 3-(4-chlorophenyl)-but-2-enyl | F | H | F | H |
| I-727 | 3-(4-chlorophenyl)-3-fluoro-allyl | F | H | F | H |
| I-728 | 3-chloro-4-fluoro-cinnamyl | F | H | F | H |
| I-729 | 3,5-dichloro-cinnamyl | F | H | F | H |
| I-730 | 5-phenyl-penta-2,4-dienyl | F | H | F | H |
| I-731 | 4-isopropyloxycarbonylamino-cinnamyl | F | H | F | H |
| I-732 | 3-naphthalen-2-yl-allyl | F | H | F | H |
| I-733 | 3-(5-trifluoromethyl-pyridin-2-yl)-allyl | F | H | F | H |
| I-734 | 3-(5-chloro-pyridin-2-yl)-allyl | F | H | F | H |
| I-735 | 3-pyridin-4-yl-allyl | F | H | F | H |
| I-736 | 3-(2-Chloro-pyridin-4-yl)-allyl | F | H | F | H |
| I-737 | 4-chlorobenzyl | F | F | H | H |
| I-738 | Cinnamyl | F | F | H | H |
| I-739 | 4-chlorocinnamyl | F | F | H | H |

TABLE 1-continued

| Compound No | R⁸ | $R^{4a}$ | $R^{4b}$ | $R^{4c}$ | $R^{4d}$ |
|---|---|---|---|---|---|
| I-740 | 4-fluorocinnamyl | F | F | H | H |
| I-741 | 4-bromocinnamyl | F | F | H | H |
| I-742 | 4-trifluoromethylcinnamyl | F | F | H | H |
| I-743 | 4-trifluoromethoxycinnamyl | F | F | H | H |
| I-744 | 4-pentafluoroethoxycinnamyl | F | F | H | H |
| I-745 | 4-methoxycinnamyl | F | F | H | H |
| I-746 | 4-ethoxycinnamyl | F | F | H | H |
| I-747 | 4-cyanocinnamyl | F | F | H | H |
| I-748 | 3-(6-chloro-pyridin-3-yl)-allyl | F | F | H | H |
| I-749 | 3-(4-chlorophenyl)-but-2-enyl | F | F | H | H |
| I-750 | 3-(4-chlorophenyl)-3-fluoro-allyl | F | F | H | H |
| I-751 | 3-chloro-4-fluoro-cinnamyl | F | F | H | H |
| I-752 | 3,5-dichloro-cinnamyl | F | F | H | H |
| I-753 | 5-phenyl-penta-2,4-dienyl | F | F | H | H |
| I-754 | 4-isopropyloxycarbonylamino-cinnamyl | F | F | H | H |
| I-755 | 3-naphthalen-2-yl-allyl | F | F | H | H |
| I-756 | 3-(5-trifluoromethyl-pyridin-2-yl)-allyl | F | F | H | H |
| I-757 | 3-(5-chloro-pyridin-2-yl)-allyl | F | F | H | H |
| I-758 | 3-pyridin-4-yl-allyl | F | F | H | H |
| I-759 | 3-(2-Chloro-pyridin-4-yl)-allyl | F | F | H | H |
| I-760 | 4-chlorobenzyl | Cl | F | H | H |
| I-761 | Cinnamyl | Cl | F | H | H |
| I-762 | 4-chlorocinnamyl | Cl | F | H | H |
| I-763 | 4-fluorocinnamyl | Cl | F | H | H |
| I-764 | 4-bromocinnamyl | Cl | F | H | H |
| I-765 | 4-trifluoromethylcinnamyl | Cl | F | H | H |
| I-766 | 4-trifluoromethoxycinnamyl | Cl | F | H | H |
| I-767 | 4-pentafluoroethoxycinnamyl | Cl | F | H | H |
| I-768 | 4-methoxycinnamyl | Cl | F | H | H |
| I-769 | 4-ethoxycinnamyl | Cl | F | H | H |
| I-770 | 4-cyanocinnamyl | Cl | F | H | H |
| I-771 | 3-(6-chloro-pyridin-3-yl)-allyl | Cl | F | H | H |
| I-772 | 3-(4-chlorophenyl)-but-2-enyl | Cl | F | H | H |
| I-773 | 3-(4-chlorophenyl)-3-fluoro-allyl | Cl | F | H | H |
| I-774 | 3-chloro-4-fluoro-cinnamyl | Cl | F | H | H |
| I-775 | 3,5-dichloro-cinnamyl | Cl | F | H | H |
| I-776 | 5-phenyl-penta-2,4-dienyl | Cl | F | H | H |
| I-777 | 4-isopropyloxycarbonylamino-cinnamyl | Cl | F | H | H |
| I-778 | 3-naphthalen-2-yl-allyl | Cl | F | H | H |
| I-779 | 3-(5-trifluoromethyl-pyridin-2-yl)-allyl | Cl | F | H | H |
| I-780 | 3-(5-chloro-pyridin-2-yl)-allyl | Cl | F | H | H |
| I-781 | 3-pyridin-4-yl-allyl | Cl | F | H | H |
| I-782 | 3-(2-Chloro-pyridin-4-yl)-allyl | Cl | F | H | H |

Table II provides 782 compounds of formula Ib

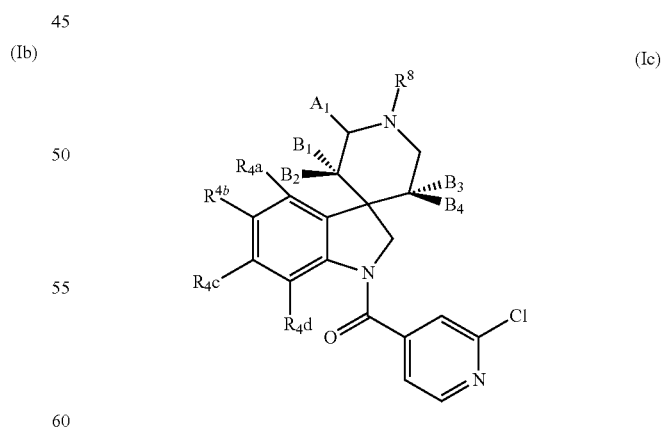

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table III provides 782 compounds of formula Ic wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table IV provides 782 compounds of formula Id

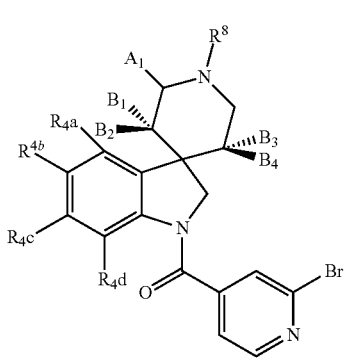
(Id)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table V provides 782 compounds of formula Ie

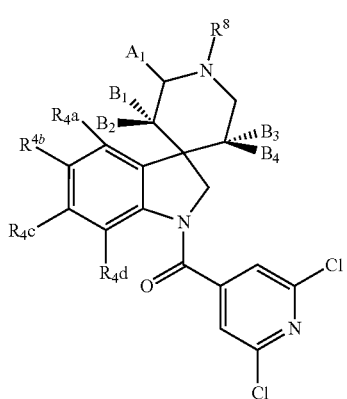
(Ie)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table VI provides 782 compounds of formula If

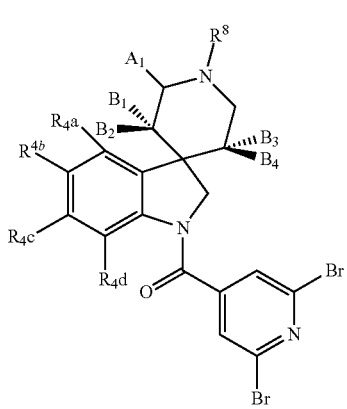
(If)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table VII provides 782 compounds of formula Ig

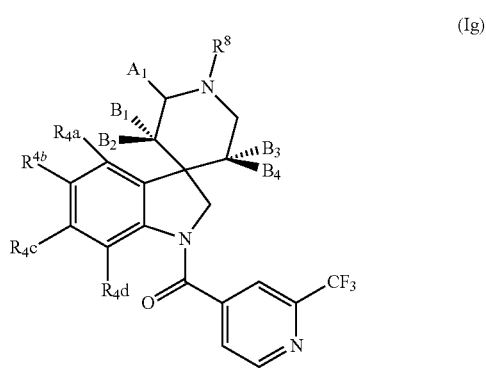
(Ig)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table VIII provides 782 compounds of formula Ih

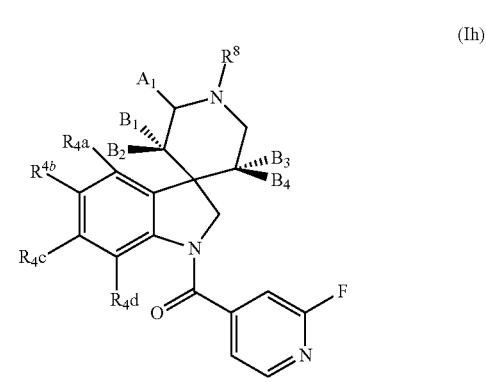
(Ih)

wherein $A_1$ is hydrogen, $B_1$ is $CH_3$, $B_2$, $B_3$ and $B_4$ are all hydrogen and the values of $R^4$, $R^{4b}$, $R^{4c}$, $R^{4d}$ and $R^8$ are given in Table 1.

Table IX provides 782 compounds of formula Ii

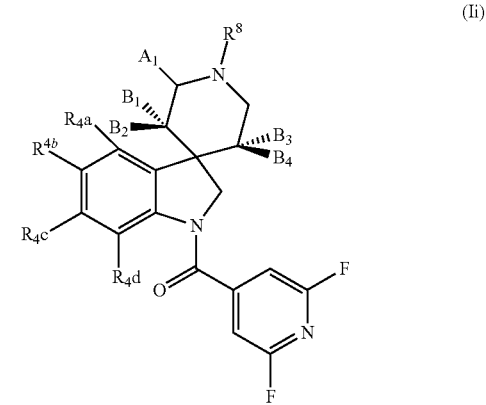
(Ii)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table X provides 782 compounds of formula Ij

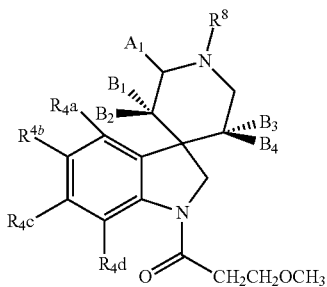
(Ij)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XI provides 782 compounds of formula Ik

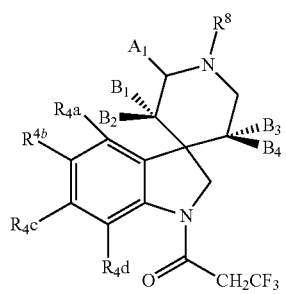
(Ik)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XII provides 782 compounds of formula Il

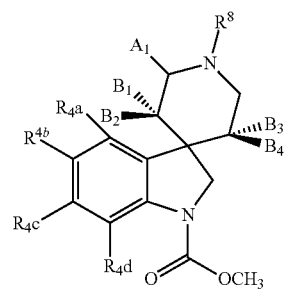
(Il)

wherein $A_1$ is hydrogen, $B_1$ is $CH_3$, $B_2$, $B_3$ and $B_4$ are all hydrogen and the values of $R^{4c}$, $R^{4b}$, $R^{4c}$, $R^{4d}$ and $R^8$ are given in Table 1.

Table XIII provides 782 compounds of formula Im

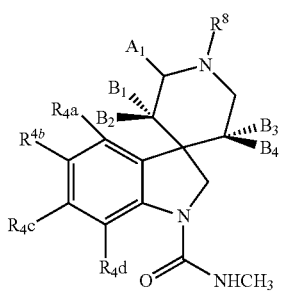
(Im)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XIV provides 782 compounds of formula In

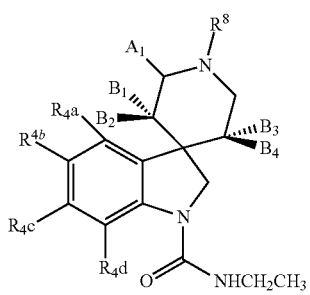
(In)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XV provides 782 compounds of formula Io

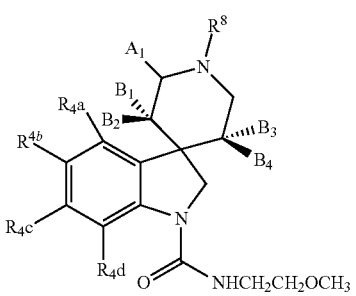
(Io)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XVI provides 782 compounds of formula Ip

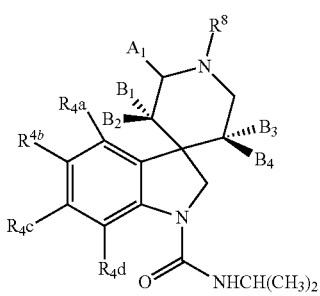
(Ip)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XVII provides 782 compounds of formula Iq

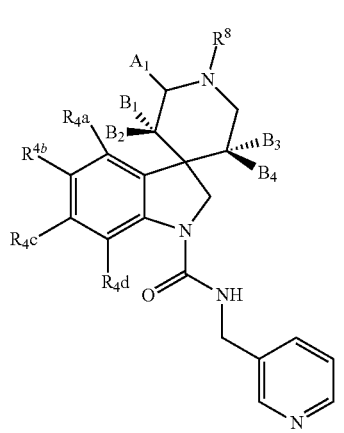

(Iq)

wherein $A_1$ is hydrogen, $B_1$ is $CH_3$, $B_2$, $B_3$ and $B_4$ are all hydrogen and the values of $R^{4c}$, $R^{4b}$, $R^{4c}$, $R^{4d}$ and $R^8$ are given in Table 1.

Table XVIII provides 782 compounds of formula Ir

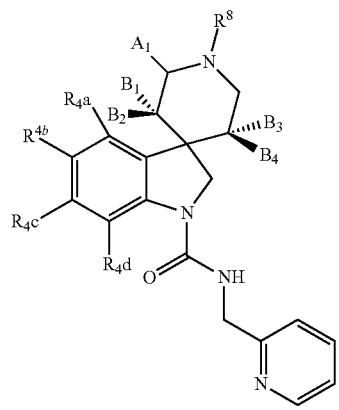

(Ir)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XIX provides 782 compounds of formula Is

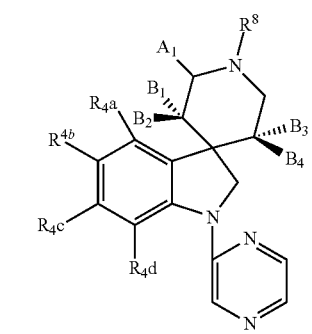

(Is)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XX provides 782 compounds of formula It

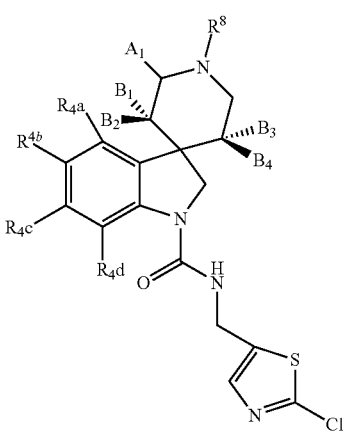

(It)

wherein $A_1$ is hydrogen, $B_1$ is $CH_3$, $B_2$, $B_3$ and $B_4$ are all hydrogen and the values of $R^{4c}$, $R^{4b}$, $R^{4c}$, $R^{4d}$ and $R^8$ are given in Table 1.

Table XXI provides 782 compounds of formula Iu

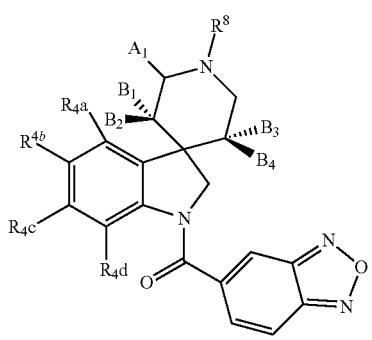

(Iu)

wherein $A_1$ is hydrogen, $B_1$ is $CH_3$, $B_2$, $B_3$ and $B_4$ are all hydrogen and the values of $R^4$, $R^{4b}$, $R^{4c}$, $R^{4d}$ and $R^8$ are given in Table 1.

Table XXII provides 782 compounds of formula Iv

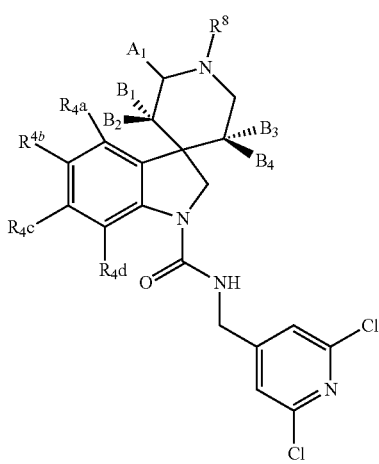

(Iv)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXIII provides 782 compounds of formula Iw

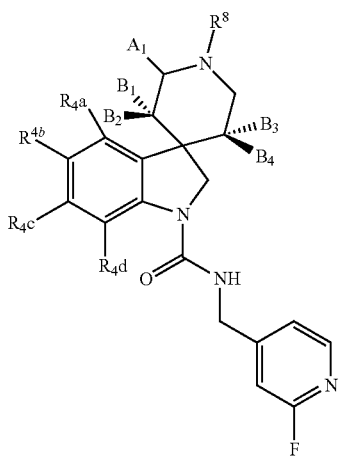
(Iw)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXIV provides 782 compounds of formula Ix

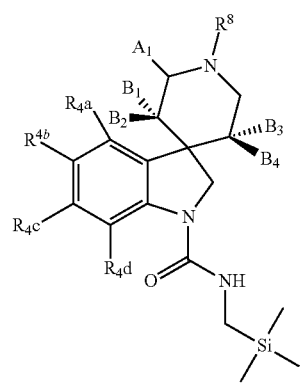
(Ix)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXV provides 782 compounds of formula Iy

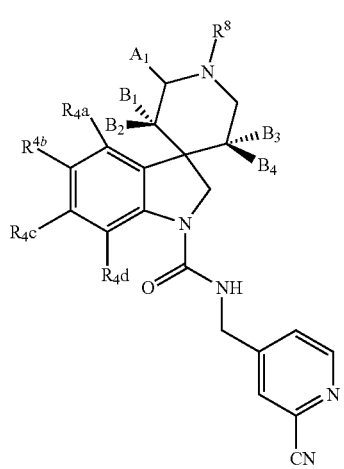
(Iy)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXVI provides 782 compounds of formula Iz

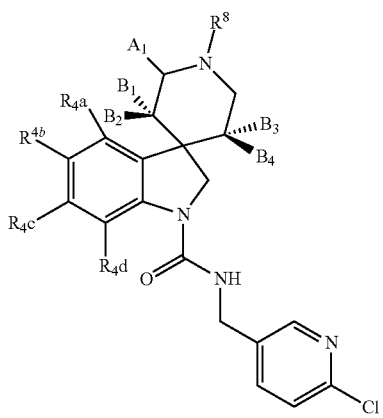
(Iz)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXVII provides 782 compounds of formula Iaa

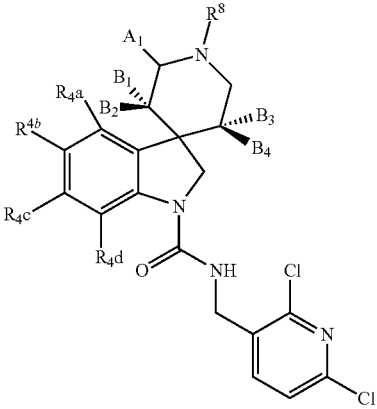
(Iaa)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXVIII provides 782 compounds of formula Iab

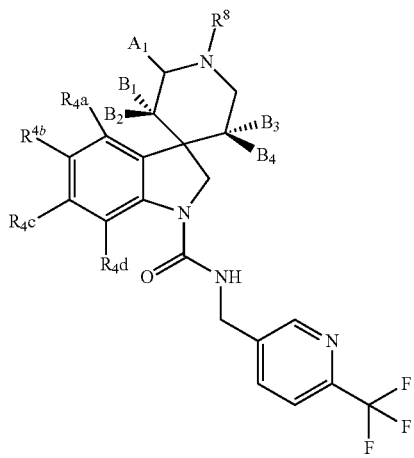
(Iab)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXIX provides 782 compounds of formula Iac

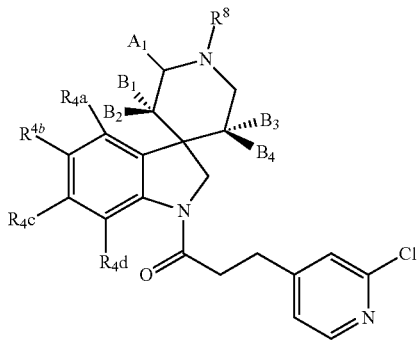

(Iac)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXX provides 782 compounds of formula Iad

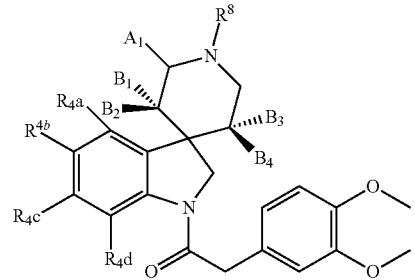

(Iad)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXXI provides 782 compounds of formula Iae

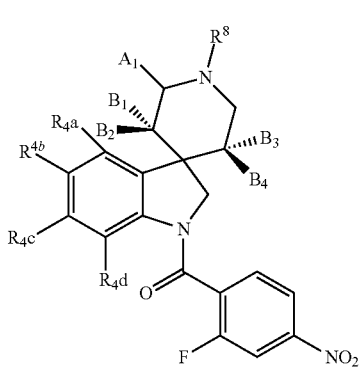

(Iae)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXXII provides 782 compounds of formula Iaf

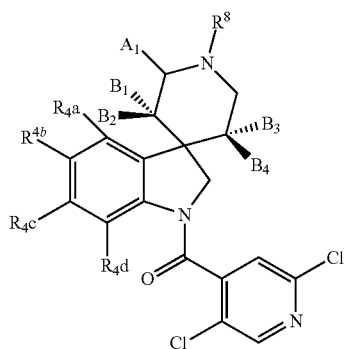

(Iaf)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXXIII provides 782 compounds of formula Iag

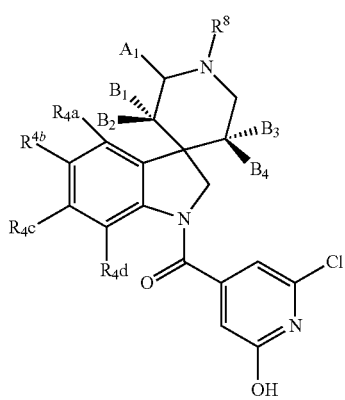

(Iag)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXXIV provides 782 compounds of formula Iah

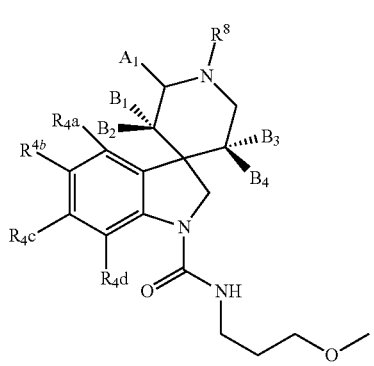

(Iah)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XXXV provides 782 compounds of formula Iai

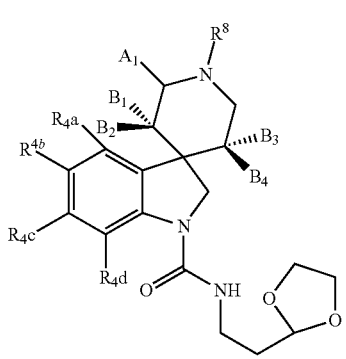
(Iai)

wherein A₁ is hydrogen, B₁ is CH₃, B₂, B₃ and B₄ are all hydrogen and the values of $R^{4c}$, $R^{4b}$, $R^{4c}$, $R^{4d}$ and $R^8$ are given in Table 1.

Table XXXVI provides 782 compounds of formula Iaj

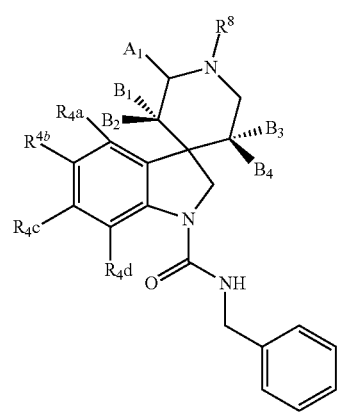
(Iaj)

wherein A₁ is hydrogen, B₁ is CH₃, B₂, B₃ and B₄ are all hydrogen and the values of $R^{4a}$, $R^{4b}$, $R^{4c}$, $R^{4d}$ and $R^8$ are given in Table 1.

Table XXXVII provides 782 compounds of formula Iak

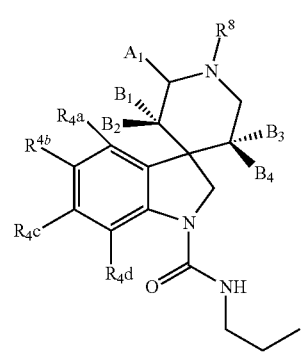
(Iak)

wherein A₁ is hydrogen, B₁ is CH₃, B₂, B₃ and B₄ are all hydrogen and the values of $R^{4a}$, $R^{4b}$, $R^{4c}$, $R^{4d}$ and $R^8$ are given in Table 1.

Table XXXVIII provides 782 compounds of formula Ial

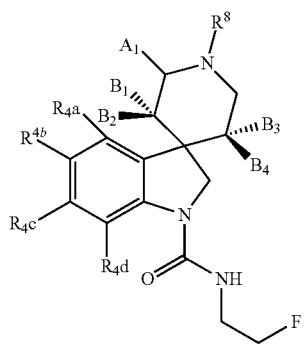
(Ial)

wherein A₁ is hydrogen, B₁ is CH₃, B₂, B₃ and B₄ are all hydrogen and the values of $R^{4a}$, $R^{4b}$, $R^{4c}$, $R^{4d}$ and $R^8$ are given in Table 1.

Table XXXIX provides 782 compounds of formula Iam

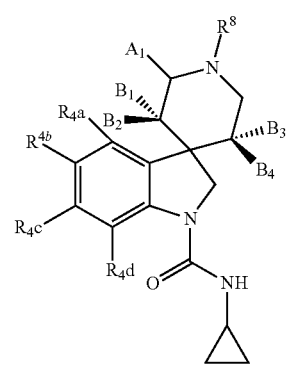
(Iam)

wherein A₁ is hydrogen, B₁ is CH₃, B₂, B₃ and B₄ are all hydrogen and the values of $R^4$, $R^{4b}$, $R^{4c}$, $R^{4d}$ and $R^8$ are given in Table 1.

Table XL provides 782 compounds of formula Ian

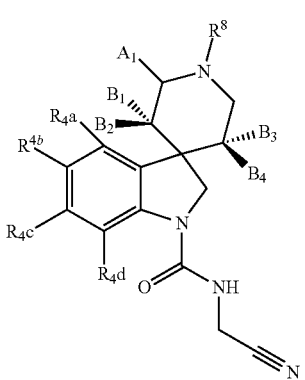
(Ian)

wherein A₁ is hydrogen, B₁ is CH₃, B₂, B₃ and B₄ are all hydrogen and the values of $R^{4a}$, $R^{4b}$, $R^{4c}$, $R^{4d}$ and $R^8$ are given in Table 1.

Table XLI provides 782 compounds of formula Iao

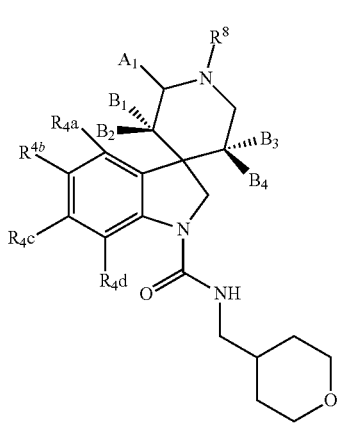
(Iao)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XLII provides 782 compounds of formula Iap

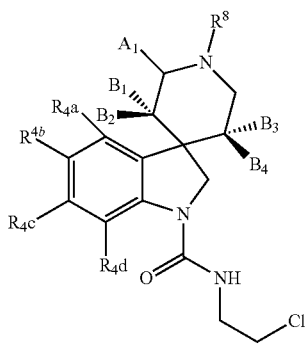
(Iap)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XLIII provides 782 compounds of formula Iaq

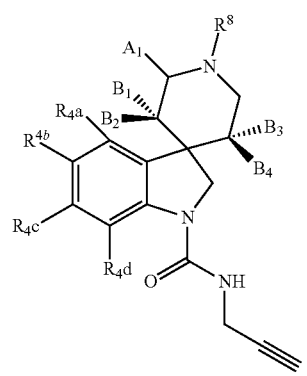
(Iaq)

wherein $A_1$ is hydrogen, $B_1$ is $CH_3$, $B_2$, $B_3$ and $B_4$ are all hydrogen and the values of $R^{4c}$, $R^{4b}$, $R^{4c}$, $R^{4d}$ and $R^8$ are given in Table 1.

Table XLIV provides 782 compounds of formula Iar

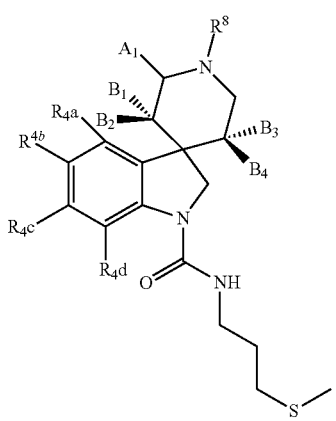
(Iar)

wherein $A_1$ is hydrogen, $B_1$ is $CH_3$, $B_2$, $B_3$ and $B_4$ are all hydrogen and the values of $R^4$, $R^{4b}$, $R^{4c}$, $R^{4d}$ and $R^8$ are given in Table 1.

Table XLV provides 782 compounds of formula Ias

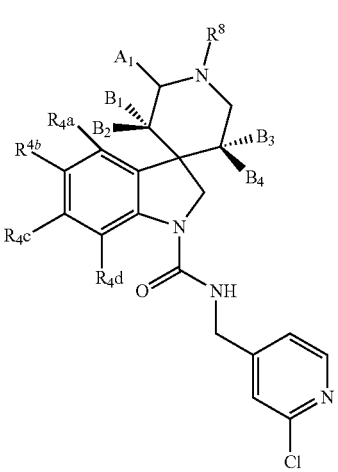
(Ias)

wherein $A_1$ is hydrogen, $B_1$ is $CH_3$, $B_2$, $B_3$ and $B_4$ are all hydrogen and the values of $R^4$, $R^{4b}$, $R^{4c}$, $R^{4d}$ and $R^8$ are given in Table 1.

Table XLVI provides 782 compounds of formula Iat

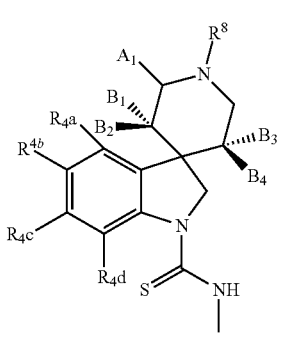
(Iat)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XLVII provides 782 compounds of formula Iau

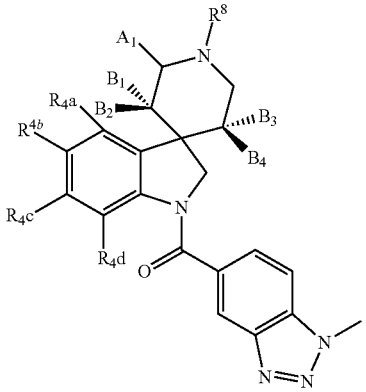

(Iau)

wherein $A_1$ is hydrogen, $B_1$ is $CH_3$, $B_2$, $B_3$ and $B_4$ are all hydrogen and the values of $R^{4c}$, $R^{4b}$, $R^{4c}$, $R^{4d}$ and $R^8$ are given in Table 1.

Table XLVIII provides 782 compounds of formula Iav

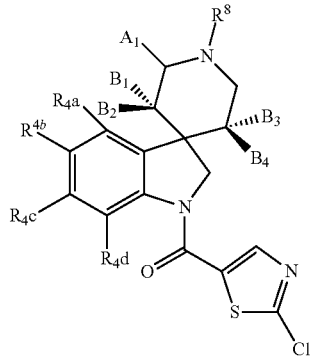

(Iav)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table XLIX provides 782 compounds of formula Iaw

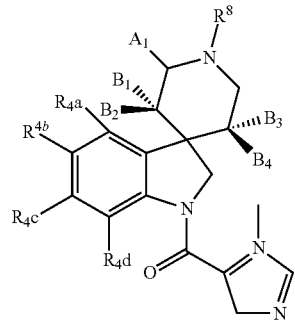

(Iaw)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table L provides 782 compounds of formula Iax

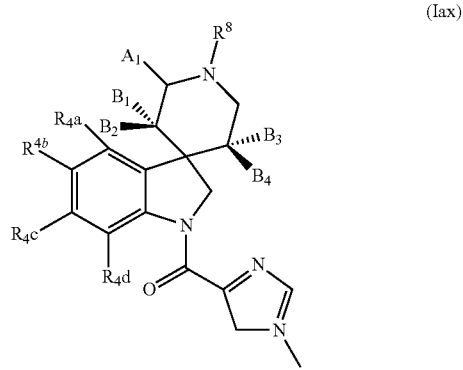

(Iax)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LI provides 782 compounds of formula Iay

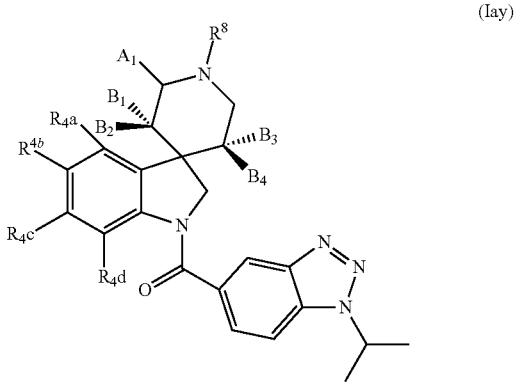

(Iay)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LII provides 782 compounds of formula Iaz

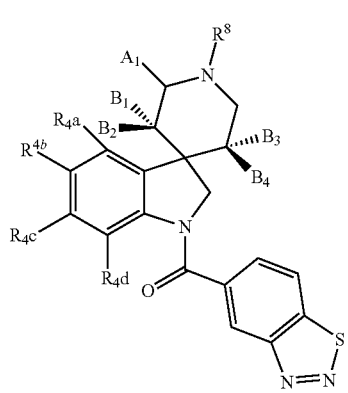

(Iaz)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LIII provides 782 compounds of formula Iba

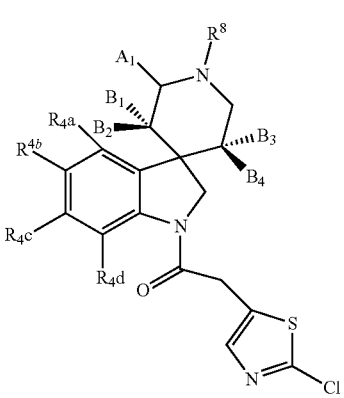
(Iba)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LIV provides 782 compounds of formula Ibb

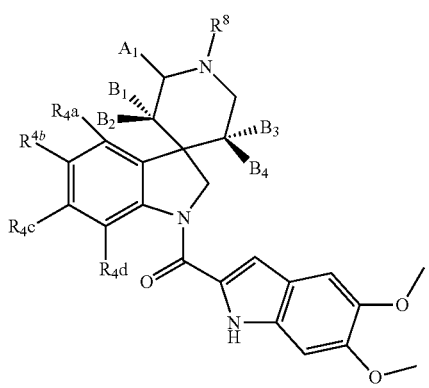
(Ibb)

wherein $A_1$ is hydrogen, $B_1$ is $CH_3$, $B_2$, $B_3$ and $B_4$ are all hydrogen and the values of $R^4$, $R^{4b}$, $R^{4c}$, $R^{4d}$ and $R^8$ are given in Table 1.

Table LV provides 782 compounds of formula Ibc

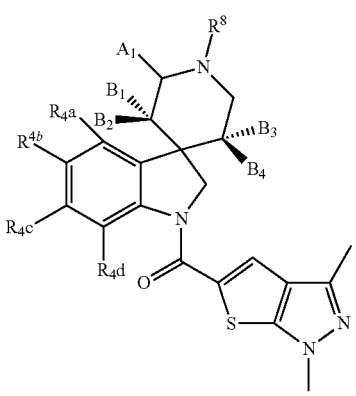
(Ibc)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LVI provides 782 compounds of formula Ibd

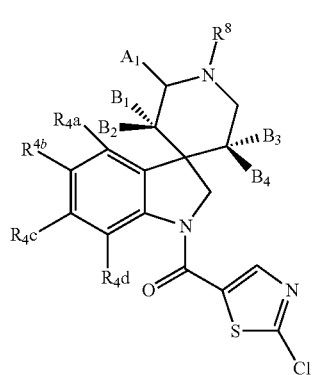
(Ibd)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LVII provides 782 compounds of formula Ibe

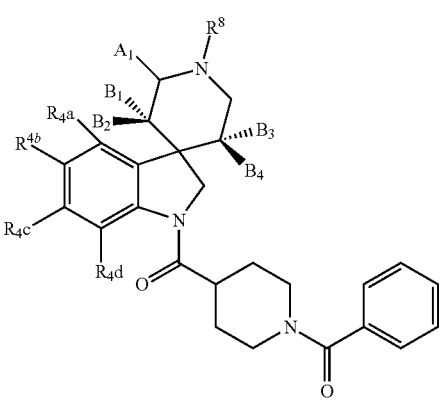
(Ibe)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LVIII provides 782 compounds of formula Ibf

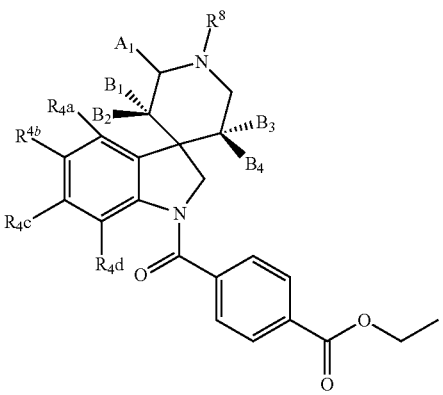
(Ibf)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LIX provides 782 compounds of formula Ibg

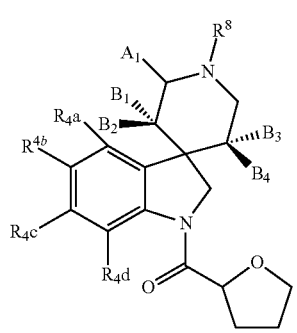
(Ibg)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LX provides 782 compounds of formula Ibh

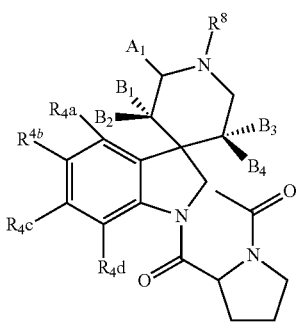
(Ibh)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXI provides 782 compounds of formula Ibi

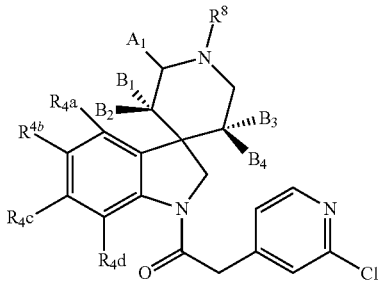
(Ibi)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXII provides 782 compounds of formula Ibj

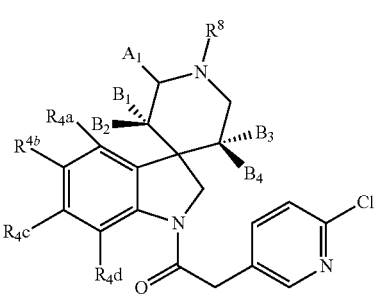
(Ibj)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXIII provides 782 compounds of formula Ibk

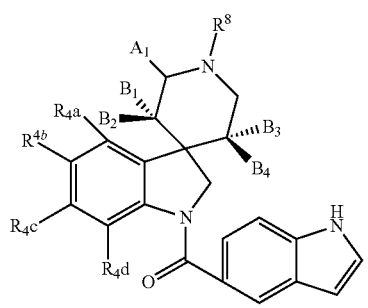
(Ibk)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXIV provides 782 compounds of formula Ibl

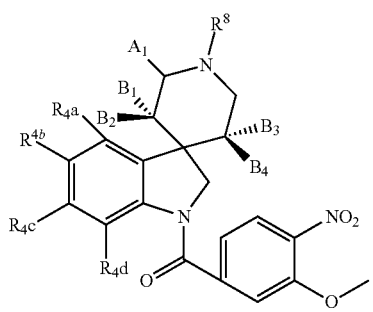
(Ibl)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXV provides 782 compounds of formula Ibm (Ibm)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXVI provides 782 compounds of formula Ibn (Ibn)

wherein $A_1$ is hydrogen, $B_1$ is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table LXVII provides 782 compounds of formula Ibo (Ibo)

wherein $A_1$ is hydrogen, B is $CH_3$, $B_2$, $B_3$ and $B_4$ are all hydrogen and the values of $R^{4a}$, $R^{4b}$, $R^{4c}$, $R^{4d}$ and $R^8$ are given in Table 1.

Table CI provides 782 compounds of formula Ia wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CII provides 782 compounds of formula Ib wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CIII provides 782 compounds of formula Ic wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CIV provides 782 compounds of formula Id wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CV provides 782 compounds of formula Ie wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CVI provides 782 compounds of formula If wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CVII provides 782 compounds of formula Ig wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CVIII provides 782 compounds of formula Ih wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CIX provides 782 compounds of formula Ii wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CX provides 782 compounds of formula Ij wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXI provides 782 compounds of formula Ik wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXII provides 782 compounds of formula Il wherein $A_1$ is hydrogen, $B_1$ is OH, $B_2$, $B_3$ and $B_4$ are all hydrogen and the values of $R^4$, $R^{4b}$, $R^{4c}$ Id and $R^8$ are given in Table 1.

Table CXIII provides 782 compounds of formula Im wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXIV provides 782 compounds of formula In wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXV provides 782 compounds of formula Io wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXVI provides 782 compounds of formula Ip wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXVII provides 782 compounds of formula Iq wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXVIII provides 782 compounds of formula Ir wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXIX provides 782 compounds of formula Is wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXX provides 782 compounds of formula It wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXI provides 782 compounds of formula Iu wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXII provides 782 compounds of formula Iv wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXIII provides 782 compounds of formula Iw wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXIV provides 782 compounds of formula Ix wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXV provides 782 compounds of formula Iy wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXVI provides 782 compounds of formula Iz wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1

Table CXXVII provides 782 compounds of formula Iaa wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXVIII provides 782 compounds of formula Iab wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXIX provides 782 compounds of formula Iac wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXX provides 782 compounds of formula Iad wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXI provides 782 compounds of formula Iae wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXII provides 782 compounds of formula Iaf wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXIII provides 782 compounds of formula Iag wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXIV provides 782 compounds of formula Iah wherein $A_1$ is hydrogen, B is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXV provides 782 compounds of formula Iai wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXVI provides 782 compounds of formula Iaj wherein $A_1$ is hydrogen, $B_1$ is OH, $B_2$, $B_3$ and $B_4$ are all hydrogen and the values of $R^{4c}$, $R^{4b}$, $R^{4c}$, $R^{4d}$ and $R^8$ are given in Table 1.

Table CXXXVII provides 782 compounds of formula Iak wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXVIII provides 782 compounds of formula Ial wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXXXIX provides 782 compounds of formula Iam wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXL provides 782 compounds of formula Ian wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLI provides 782 compounds of formula Iao wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLII provides 782 compounds of formula Iap wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLIII provides 782 compounds of formula Iaq wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLIV provides 782 compounds of formula Iar wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLV provides 782 compounds of formula Ias wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLVI provides 782 compounds of formula Iat wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLVII provides 782 compounds of formula Iau wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLVIII provides 782 compounds of formula Iav wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CXLIX provides 782 compounds of formula Iaw wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CCL provides 782 compounds of formula Iax wherein $A_1$ is hydrogen, $B_1$ is OH, $B_2$, $B_3$ and $B_4$ are all hydrogen and the values of $R^{4a}$, $R^{4a}$, $R^{4c}$, $R^{4d}$ and $R^8$ are given in Table 1.

Table CLI provides 782 compounds of formula Iay wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLII provides 782 compounds of formula m/z wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLIII provides 782 compounds of formula Iba wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLIV provides 782 compounds of formula Ibb wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLV provides 782 compounds of formula Ibc wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLVI provides 782 compounds of formula Ibd wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLVII provides 782 compounds of formula Ibd wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLVIII provides 782 compounds of formula Ibf wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLIX provides 782 compounds of formula Ibg wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLX provides 782 compounds of formula Ibh wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXI provides 782 compounds of formula Ibi wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXII provides 782 compounds of formula Ibj wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXIII provides 782 compounds of formula Ibk wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXIV provides 782 compounds of formula Ibl wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXV provides 782 compounds of formula Ibm wherein $A_1$ is hydrogen, $B_1$ is OH, $B_2$, $B_3$ and $B_4$ are all hydrogen and the values of $R^{4c}$, $R^{4b}$, $R^{4c}$, $R^{4d}$ and $R^8$ are given in Table 1.

Table CLXVI provides 782 compounds of formula Ibn wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CLXVII provides 782 compounds of formula Ibo wherein $A_1$ is hydrogen, $B_1$ is OH, $B_2$, $B_3$ and $B_4$ are all hydrogen and the values of $R^{4a}$, $R^{4b}$, $R^{4c}$, $R^{4d}$ and $R^8$ are given in Table 1.

Table CCI provides 782 compounds of formula Ia wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCII provides 782 compounds of formula Ib wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCIII provides 782 compounds of formula Ic wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCIV provides 782 compounds of formula Id wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCV provides 782 compounds of formula Ie wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCVI provides 782 compounds of formula If wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCVI provides 782 compounds of formula Ig wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCVIII provides 782 compounds of formula Ih wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1

Table CCIX provides 782 compounds of formula Ii wherein $A_1$ is hydrogen, B is F, $B_2$, $B_3$ and $B_4$ are all hydrogen and the values of $R^{4a}$, $R^{4b}$, $R^{4c}$, $R^{4d}$ and $R^8$ are given in Table 1.

Table CCX provides 782 compounds of formula Ij wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXI provides 782 compounds of formula Ik wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXII provides 782 compounds of formula Il wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXIII provides 782 compounds of formula Im wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXIV provides 782 compounds of formula In wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXV provides 782 compounds of formula Io wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXVI provides 782 compounds of formula Ip wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXVII provides 782 compounds of formula Iq wherein $A_1$ is hydrogen, B is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXVIII provides 782 compounds of formula Ir wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXIX provides 782 compounds of formula Is wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXX provides 782 compounds of formula It wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXI provides 782 compounds of formula Iu wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXII provides 782 compounds of formula Iv wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXIII provides 782 compounds of formula Iw wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXIV provides 782 compounds of formula Ix wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXV provides 782 compounds of formula Iy wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXVI provides 782 compounds of formula Iz wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXVII provides 782 compounds of formula Iaa wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXVIII provides 782 compounds of formula Iab wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXLX provides 782 compounds of formula Iac wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXX provides 782 compounds of formula Iad wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXI provides 782 compounds of formula Iae wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXII provides 782 compounds of formula Iaf wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXIII provides 782 compounds of formula Iag wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXIV provides 782 compounds of formula Iah wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXV provides 782 compounds of formula Iai wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXVI provides 782 compounds of formula Iaj wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXVII provides 782 compounds of formula Iak wherein $A_1$ is hydrogen, B is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXVIII provides 782 compounds of formula Ial wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXXXIX provides 782 compounds of formula Iam wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXL provides 782 compounds of formula Ian wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLI provides 782 compounds of formula Iao wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLII provides 782 compounds of formula Iap wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLIII provides 782 compounds of formula Iaq wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLIV provides 782 compounds of formula Iar wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLV provides 782 compounds of formula Ias wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLVI provides 782 compounds of formula Iat wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLVII provides 782 compounds of formula Iau wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLVII provides 782 compounds of formula Iav wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCXLIX provides 782 compounds of formula Iaw wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCL provides 782 compounds of formula Iax wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLI provides 782 compounds of formula wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1

Table CCLII provides 782 compounds of formula Iaz wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLIII provides 782 compounds of formula Iba wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLIV provides 782 compounds of formula Ibb wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLV provides 782 compounds of formula Ibc wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^5$ are given in Table 1.

Table CCLVI provides 782 compounds of formula Ibd wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLVII provides 782 compounds of formula Ibe wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLVIII provides 782 compounds of formula Ibf wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLIX provides 782 compounds of formula Ibg wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLX provides 782 compounds of formula Ibh wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXI provides 782 compounds of formula Ibi wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXII provides 782 compounds of formula Ibj wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXIII provides 782 compounds of formula Ibk wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXIV provides 782 compounds of formula Ibl wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXV provides 782 compounds of formula Ibm wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXVI provides 782 compounds of formula Ibn wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCLXVII provides 782 compounds of formula Ibo wherein $A_1$ is hydrogen, $B_1$ is F, $B_2$, $B_3$ and $B_4$ are all hydrogen and the values of $R^{4a}$, $R^{4b}$, $R^{4c}$, $R^{4d}$ and $R^8$ are given in Table 1.

Table CCCI provides 782 compounds of formula Ia wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCII provides 782 compounds of formula Ib wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCIII provides 782 compounds of formula Ic wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCIV provides 782 compounds of formula Id wherein $A_1$ is hydrogen, $B_1$ is F, $B_2$ is F, 13 and $B_4$ are both hydrogen and the values of $R^{4a}$, $R^{4b}$, $R^{4c}$, $R^{4d}$ and $R^8$ are given in Table 1.

Table CCCV provides 782 compounds of formula Ie wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCVI provides 782 compounds of formula If wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCVII provides 782 compounds of formula Ig wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCVIII provides 782 compounds of formula Ih wherein $A_1$ is hydrogen, $B_1$ is F, $B_2$ is F, 13 and $B_4$ are both hydrogen and the values of $R^{4a}$, $R^{4b}$, $R^{4c}$, $R^{4d}$ and $R^8$ are given in Table 1.

Table CCCIX provides 782 compounds of formula Ii wherein $A_1$ is hydrogen, $B_1$ is F, $B_2$ is F, 13 and $B_4$ are both hydrogen and the values of $R^{4a}$, $R^{4b}$, $R^{4c}$, $R^{4d}$ and $R^8$ are given in Table 1.

Table CCCX provides 782 compounds of formula Ij wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXI provides 782 compounds of formula Ik wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXII provides 782 compounds of formula Il wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXIII provides 782 compounds of formula Im wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXIV provides 782 compounds of formula In wherein $A_1$ is hydrogen, B is F, $B_2$ is F, $B_3$ and $B_4$ are both hydrogen and the values of $R^{4a}$, $R^{4b}$, $R^{4c}$. $R^{4d}$ and $R^8$ are given in Table 1.

Table CCCXV provides 782 compounds of formula Io wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXVI provides 782 compounds of formula Ip wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXVII provides 782 compounds of formula Iq wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXVIII provides 782 compounds of formula Ir wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXIX provides 782 compounds of formula Is wherein $A_1$ is hydrogen, $B_1$ is F, $B_2$ is F, 13 and $B_4$ are both hydrogen and the values of $R^{4c}$, $R^{4b}$, $R^{4c}$, $R^{4d}$ and $R^8$ are given in Table 1.

Table CCCXX provides 782 compounds of formula It wherein $A_1$ is hydrogen, $B_1$ is F, $B_2$ is F, 13 and $B_4$ are both hydrogen and the values of $R^{4a}$, $R^{4b}$, $R^{4c}$, $R^{4d}$ and $R^8$ are given in Table 1.

Table CCCXXI provides 782 compounds of formula Iu wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXII provides 782 compounds of formula Iv wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXIII provides 782 compounds of formula Iw wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXIV provides 782 compounds of formula Ix wherein $A_1$ is hydrogen, $B_1$ is F, $B_2$ is F, $B_3$ and $B_4$ are both hydrogen and the values of $R^4$, $R^{4b}$, $R^{4c}$, $R^{4d}$ and $R^8$ are given in Table 1.

Table CCCXXV provides 782 compounds of formula Iy wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXVI provides 782 compounds of formula Iz wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXVII provides 782 compounds of formula Iaa wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXVIII provides 782 compounds of formula Iab wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXIX provides 782 compounds of formula Iac wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXX provides 782 compounds of formula Iad wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXI provides 782 compounds of formula Iae wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXII provides 782 compounds of formula Iaf wherein $A_1$ is hydrogen, B is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXIII provides 782 compounds of formula Iag wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXIV provides 782 compounds of formula Iah wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXV provides 782 compounds of formula Iai wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXVI provides 782 compounds of formula Iaj wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXVII provides 782 compounds of formula Iak wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXVIII provides 782 compounds of formula Ial wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXXXIX provides 782 compounds of formula Iam wherein $A_1$ is hydrogen, $B_1$ is F, $B_2$ is F, $B_3$ and $B_4$ are both hydrogen and the values of $R^4$, $R^{4b}$, $R^{4c}$, $R^{4d}$ and $R^8$ are given in Table 1.

Table CCCXL provides 782 compounds of formula Ian wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLI provides 782 compounds of formula Iao wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLII provides 782 compounds of formula Iap wherein $A_1$ is hydrogen, B is F, $B_2$ is F, $B_3$ and $B_4$ are both hydrogen and the values of $R^4$, $R^{4b}$, $R^{4c}$, $R^{4d}$ and $R^8$ are given in Table 1.

Table CCCXLIII provides 782 compounds of formula Iaq wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLIV provides 782 compounds of formula Iar wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLV provides 782 compounds of formula Ias wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLVI provides 782 compounds of formula Iat wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLVII provides 782 compounds of formula Iau wherein $A_1$ is hydrogen, B is F, $B_2$ is F, $B_3$ and $B_4$ are both hydrogen and the values of $R^{4a}$, $R^{4b}$, $R^{4c}$. $R^{4d}$ and $R^8$ are given in Table 1.

Table CCCXLVIII provides 782 compounds of formula Iav wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCXLIX provides 782 compounds of formula Iaw wherein $A_1$ is hydrogen, $B_1$ is F, $B_2$ is F, $B_3$ and $B_4$ are both hydrogen and the values of $R^{4a}$, $R^{4b}$, $R^{4c}$, $R^{4d}$ and $R^8$ are given in Table 1.

Table CCCL provides 782 compounds of formula Iax wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLI provides 782 compounds of formula Iay wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLII provides 782 compounds of formula Iaz wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLIII provides 782 compounds of formula Iba wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLIV provides 782 compounds of formula Ibb wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLV provides 782 compounds of formula Ibc wherein $A_1$ is hydrogen, $B_1$ is F, $B_2$ is F, $B_3$ and $B_4$ are both hydrogen and the values of $R^4, R^{4b}, R^{4c}, R^{4d}$ and $R^8$ are given in Table 1.

Table CCCLVI provides 782 compounds of formula Ibd wherein $A_1$ is hydrogen, $B_1$ is F, $B_2$ is F, $B_3$ and $B_4$ are both hydrogen and the values of $R^4, R^{4b}, R^{4c}, R^{4d}$ and $R^8$ are given in Table 1.

Table CCCLVII provides 782 compounds of formula Ibe wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLVIII provides 782 compounds of formula Ibf wherein $A_1$ is hydrogen, $B_1$ is F, $B_2$ is F, $B_3$ and $B_4$ are both hydrogen and the values of $R^4, R^{4b}, R^{4c}, R^{4d}$ and $R^8$ are given in Table 1.

Table CCCLIX provides 782 compounds of formula Ibg wherein $A_1$ is hydrogen, $B_1$ is F, $B_2$ is F, $B_3$ and $B_4$ are both hydrogen and the values of $R^{4c}, R^{4b}, R^{4c}, R^{4d}$ and $R^8$ are given in Table 1.

Table CCCLX provides 782 compounds of formula Ibh wherein $A_1$ is hydrogen, B is F, $B_2$ is F, $B_3$ and $B_4$ are both hydrogen and the values of $R^{4c}, R^{4b}, R^{4c}, R^{4d}$ and $R^8$ are given in Table 1.

Table CCCLXI provides 782 compounds of formula Ibi wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLXII provides 782 compounds of formula Ibj wherein $A_1$ is hydrogen, $B_1$ is F, $B_2$ is F, $B_3$ and $B_4$ are both hydrogen and the values of $R^{4c}, R^{4b}, R^{4c}, R^{4d}$ and $R^8$ are given in Table 1.

Table CCCLXIII provides 782 compounds of formula Ibk wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLXIV provides 782 compounds of formula Ibi wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLXV provides 782 compounds of formula Ibm wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLXVI provides 782 compounds of formula Ibn wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CCCLXVII provides 782 compounds of formula Ibo wherein $A_1$ is hydrogen, $B_1$ is F, $B_2$ is F, $B_3$ and $B_4$ are both hydrogen and the values of $R^{4a}, R^{4b}, R^{4c}, R^{4d}$ and $R^8$ are given in Table 1.

Table CDI provides 782 compounds of formula Ia wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDII provides 782 compounds of formula Ib wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDIII provides 782 compounds of formula Ic wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDIV provides 782 compounds of formula Id wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDV provides 782 compounds of formula Ie wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDVI provides 782 compounds of formula If wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDVII provides 782 compounds of formula Ig wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDVIII provides 782 compounds of formula Ih wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDIX provides 782 compounds of formula Ii wherein $A_1$ is hydrogen, $B_1$ is $CH_3$, $B_2$ is $CH_3$, $B_3$ and $B_4$ are both hydrogen and the values of $R^{4c}, R^{4b}, R^{4c}, R^{4d}$ and $R^8$ are given in Table 1.

Table CDX provides 782 compounds of formula Ij wherein $A_1$ is hydrogen, $B_1$ is $CH_3$, $B_2$ is $CH_3$, $B_3$ and $B_4$ are both hydrogen and the values of $R^4, R^{4b}, R^{4c}, R^{4d}$ and $R^8$ are given in Table 1.

Table CDXI provides 782 compounds of formula Ik wherein $A_1$ is hydrogen, $B_1$ is $CH_3$, $B_2$ is $CH_3$, $B_3$ and $B_4$ are both hydrogen and the values of $R^4, R^{4b}, R^{4c}, R^{4d}$ and $R^8$ are given in Table 1.

Table CDXII provides 782 compounds of formula Il wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDXIII provides 782 compounds of formula Im wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDXIV provides 782 compounds of formula In wherein $A_1$ is hydrogen, $B_1$ is $CH_3$, $B_2$ is $CH_3$, $B_3$ and $B_4$ are both hydrogen and the values of $R^{4a}, R^{4b}, R^{4c}, R^{4d}$ and $R^8$ are given in Table 1.

Table CDXV provides 782 compounds of formula Io wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXVI provides 782 compounds of formula Ip wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXVII provides 782 compounds of formula Iq wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXVIII provides 782 compounds of formula Ir wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXIX provides 782 compounds of formula Is wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXX provides 782 compounds of formula It wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXI provides 782 compounds of formula Iu wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXII provides 782 compounds of formula Iv wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXIII provides 782 compounds of formula Iw wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXIV provides 782 compounds of formula Ix wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXV provides 782 compounds of formula Iy wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXVI provides 782 compounds of formula Iz wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXVII provides 782 compounds of formula Iaa wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXVIII provides 782 compounds of formula Iab wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXIX provides 782 compounds of formula Iac wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXX provides 782 compounds of formula Iad wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXI provides 782 compounds of formula Iae wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXII provides 782 compounds of formula Iaf wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXIII provides 782 compounds of formula Iag wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXIV provides 782 compounds of formula Iah wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXV provides 782 compounds of formula Iai wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXVI provides 782 compounds of formula Iaj wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXVII provides 782 compounds of formula Iak wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXVIII provides 782 compounds of formula Ial wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXXXIX provides 782 compounds of formula Iam wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXL provides 782 compounds of formula Ian wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLI provides 782 compounds of formula Iao wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLII provides 782 compounds of formula Iap wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLIII provides 782 compounds of formula Iaq wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLIV provides 782 compounds of formula Iar wherein $A_1$ is hydrogen, $B_1$ is $CH_3$, $B_2$ is $CH_3$, $B_3$ and $B_4$ are both hydrogen and the values of $R^{4c}$, $R^{4b}$, $R^{4c}$, $R^{4d}$ and $R^8$ are given in Table 1.

Table CDXLV provides 782 compounds of formula Ias wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLVI provides 782 compounds of formula Iat wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLVII provides 782 compounds of formula Iau wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDXLVIII provides 782 compounds of formula Iav wherein $A_1$ is hydrogen, $B_1$ is $CH_3$, $B_2$ is $CH_3$, $B_3$ and $B_4$ are both hydrogen and the values of $R^{4c}$, $R^{4b}$, $R^{4c}$, $R^{4d}$ and $R^8$ are given in Table 1.

Table CDXLIX provides 782 compounds of formula Iaw wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDL provides 782 compounds of formula Iax wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLI provides 782 compounds of formula Iay wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLII provides 782 compounds of formula Iaz wherein $A_1$ is hydrogen, $B_1$ is $CH_3$, $B_2$ is $CH_3$, $B_3$ and $B_4$ are both hydrogen and the values of $R^{4c}$, $R^{4b}$, $R^{4c}$, $R^{4d}$ and $R^8$ are given in Table 1.

Table CDLIII provides 782 compounds of formula Iba wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLIV provides 782 compounds of formula Ibb wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLV provides 782 compounds of formula Ibc wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLVI provides 782 compounds of formula Ibd wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLVII provides 782 compounds of formula Ibe wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLVIII provides 782 compounds of formula Ibf wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLIX provides 782 compounds of formula Ibg wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLX provides 782 compounds of formula Ibh wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXI provides 782 compounds of formula Ibi wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXII provides 782 compounds of formula Ibj wherein $A_1$ is hydrogen, B is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXIII provides 782 compounds of formula Ibk wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXIV provides 782 compounds of formula Ibl wherein $A_1$ is hydrogen, $B_1$ is $CH_3$, $B_2$ is $CH_3$, $B_3$ and $B_4$ are both hydrogen and the values of $R^{4c}$, $R^{4b}$, $R^{4c}$, $R^{4d}$ and $R^8$ are given in Table 1.

Table CDLXV provides 782 compounds of formula Ibm wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXVI provides 782 compounds of formula Ibn wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table CDLXVII provides 782 compounds of formula Ibo wherein $A_1$ is hydrogen, $B_1$ is $CH_3$, $B_2$ is $CH_3$, $B_3$ and $B_4$ are both hydrogen and the values of $R^{4a}$, $R^{4b}$, $R^{4c}$, $R^{4d}$ and $R^8$ are given in Table 1.

Table DI provides 782 compounds of formula Ia wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DII provides 782 compounds of formula Ib wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DIII provides 782 compounds of formula Ic wherein $A_1$ is hydrogen, $B_1$ and $B_3$ are both $CH_3$, and $B_2$ and $B_4$ are both hydrogen and the values of $R^4$, $R^{4b}$, $R^{4c}$, $R^{4d}$ and $R^8$ are given in Table 1.

Table DIV provides 782 compounds of formula Id wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DV provides 782 compounds of formula Ie wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DVI provides 782 compounds of formula If wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DVII provides 782 compounds of formula Ig wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DVIII provides 782 compounds of formula Ih wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DIX provides 782 compounds of formula Ii wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DX provides 782 compounds of formula Ij wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DXI provides 782 compounds of formula Ik wherein $A_1$ is hydrogen, $B_1$ and $B_3$ are both $CH_3$, and $B_2$ and $B_4$ are both hydrogen and the values of $R^{4a}$, $R^{4b}$, $R^{4c}$, $R^{4d}$ and $R^8$ are given in Table 1.

Table DXII provides 782 compounds of formula Il wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXIII provides 782 compounds of formula Im wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXIV provides 782 compounds of formula In wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXV provides 782 compounds of formula Io wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXVI provides 782 compounds of formula Ip wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXVII provides 782 compounds of formula Iq wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXVIII provides 782 compounds of formula Ir wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXIX provides 782 compounds of formula Is wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXX provides 782 compounds of formula It wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXI provides 782 compounds of formula Iu wherein $A_1$ is hydrogen, $B_1$ and $B_3$ are both $CH_3$, and $B_2$ and $B_4$ are both hydrogen and the values of $R^{4c}, R^{4b}, R^{4c}, R^{4d}$ and $R^8$ are given in Table 1.

Table DXXII provides 782 compounds of formula Iv wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXIII provides 782 compounds of formula Iw wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXIV provides 782 compounds of formula Ix wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXV provides 782 compounds of formula Iy wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXVI provides 782 compounds of formula Iz wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXVII provides 782 compounds of formula Iaa wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXVIII provides 782 compounds of formula Iab wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXIX provides 782 compounds of formula Iac wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXX provides 782 compounds of formula Iad wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXI provides 782 compounds of formula Iae wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXII provides 782 compounds of formula Iaf wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXIII provides 782 compounds of formula Iag wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXIV provides 782 compounds of formula Iah wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXV provides 782 compounds of formula Iai wherein $A_1$ is hydrogen, $B_1$ and $B_3$ are both $CH_3$, and $B_2$ and $B_4$ are both hydrogen and the values of $R^{4a}, R^{1b}, R^{4c}, R^{4d}$ and $R^8$ are given in Table 1.

Table DXXXVI provides 782 compounds of formula Iaj wherein $A_1$ is hydrogen, $B_1$ and $B_3$ are both $CH_3$, and $B_2$ and $B_4$ are both hydrogen and the values of $R^{4c}, R^{4b}, R^{4c}, R^{4d}$ and $R^8$ are given in Table 1.

Table DXXXVII provides 782 compounds of formula Iak wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXVIII provides 782 compounds of formula Ial wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXXXIX provides 782 compounds of formula Iam wherein $A_1$ is hydrogen, $B_1$ and $B_3$ are both $CH_3$, and $B_2$ and $B_4$ are both hydrogen and the values of $R^{4c}, R^{4b}, R^{4c}, R^{4d}$ and $R^8$ are given in Table 1.

Table DXL provides 782 compounds of formula Ian wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLI provides 782 compounds of formula Iao wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLII provides 782 compounds of formula Iap wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLIII provides 782 compounds of formula Iaq wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLIV provides 782 compounds of formula Iar wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLV provides 782 compounds of formula Ias wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLVI provides 782 compounds of formula Iat wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLVII provides 782 compounds of formula Iau wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLVIII provides 782 compounds of formula Iav wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DXLIX provides 782 compounds of formula Iaw wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DL provides 782 compounds of formula Iax wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLI provides 782 compounds of formula Iay wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLII provides 782 compounds of formula Iaz wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLIII provides 782 compounds of formula Iba wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLIV provides 782 compounds of formula Ibb wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLV provides 782 compounds of formula Ibc wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLVI provides 782 compounds of formula Ibd wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLVII provides 782 compounds of formula Ibe wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLVIII provides 782 compounds of formula Ibf wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLIX provides 782 compounds of formula Ibg wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLX provides 782 compounds of formula Ibh wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXI provides 782 compounds of formula Ibi wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXII provides 782 compounds of formula Ibj wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXIII provides 782 compounds of formula Ibk wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXIV provides 782 compounds of formula Ibl wherein $A_1$ is hydrogen, $B_1$ and $B_3$ are both $CH_3$, and $B_2$ and $B_4$ are both hydrogen and the values of $R^{4c}, R^{4b}, R^{4c}, R^{4d}$ and $R^8$ are given in Table 1.

Table DLXV provides 782 compounds of formula Ibm wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXVI provides 782 compounds of formula Ibn wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DLXVII provides 782 compounds of formula Ibo wherein $A_1$ is hydrogen, $B_1$ and $B_3$ are both $CH_3$, and $B_2$ and $B_4$ are both hydrogen and the values of $R^{4a}, R^{4b}, R^{4c}, R^{4d}$ and $R^8$ are given in Table 1.

Table DCI provides 782 compounds of formula Ia wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCII provides 782 compounds of formula Ib wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCIII provides 782 compounds of formula Ic wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCIV provides 782 compounds of formula Id wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCV provides 782 compounds of formula Ie wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCVI provides 782 compounds of formula If wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCVII provides 782 compounds of formula Ig wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCVIII provides 782 compounds of formula Ih wherein $A_1$ is hydrogen, $B_1$ and $B_4$ are both $CH_3$ and $B_2$ and $B_3$ are both hydrogen and the values of $R^{4a}, R^{4b}, R^{4c}, R^{4d}$ and $R^8$ are given in Table 1.

Table DCIX provides 782 compounds of formula Ii wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCX provides 782 compounds of formula Ij wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXI provides 782 compounds of formula Ik wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXII provides 782 compounds of formula Il wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXIII provides 782 compounds of formula Im wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXIV provides 782 compounds of formula In wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXV provides 782 compounds of formula Io wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXVI provides 782 compounds of formula Ip wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXVII provides 782 compounds of formula Iq wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXVIII provides 782 compounds of formula Ir wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXIX provides 782 compounds of formula Is wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXX provides 782 compounds of formula It wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXI provides 782 compounds of formula Iu wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXII provides 782 compounds of formula Iv wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXIII provides 782 compounds of formula Iw wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXIV provides 782 compounds of formula Ix wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXV provides 782 compounds of formula Iy wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXVI provides 782 compounds of formula Iz wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXVII provides 782 compounds of formula Iaa wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXVIII provides 782 compounds of formula Iab wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXIX provides 782 compounds of formula Iac wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXX provides 782 compounds of formula Iad wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXI provides 782 compounds of formula Iae wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXII provides 782 compounds of formula Iaf wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXIII provides 782 compounds of formula Iag wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXIV provides 782 compounds of formula Iah wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXV provides 782 compounds of formula Iai wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXVI provides 782 compounds of formula Iaj wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXVII provides 782 compounds of formula Iak wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXXXVIII provides 782 compounds of formula Ial wherein $A_1$ is hydrogen, $B_1$ and $B_4$ are both $CH_3$, and $B_2$ and $B_3$ are both hydrogen and the values of $R^{4c}, R^{4b}, R^{4c}, R^{4d}$ and $R^8$ are given in Table 1.

Table DCXXXIX provides 782 compounds of formula Iam wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXL provides 782 compounds of formula Ian wherein $A_1$ is hydrogen, $B_1$ and $B_4$ are both $CH_3$, and $B_2$ and $B_3$ are both hydrogen and the values of $R^{4a}, R^{4b}, R^{4c}, R^{4d}$ and $R^8$ are given in Table 1.

Table DCXLI provides 782 compounds of formula Iao wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLII provides 782 compounds of formula Iap wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLIII provides 782 compounds of formula Iaq wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLIV provides 782 compounds of formula Iar wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLV provides 782 compounds of formula Ias wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLVI provides 782 compounds of formula Iat wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLVII provides 782 compounds of formula Iau wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLVIII provides 782 compounds of formula Iav wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCXLIX provides 782 compounds of formula Iaw wherein $A_1$ is hydrogen, $B_1$ and $B_4$ are both $CH_3$, and $B_2$ and $B_3$ are both hydrogen and the values of $R^4$, $R^{4b}$, $R^{4c}$, $R^{4d}$ and $R^8$ are given in Table 1.

Table DCL provides 782 compounds of formula Iax wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLI provides 782 compounds of formula Iay wherein $A_1$ is hydrogen, $B_1$ and $B_4$ are both $CH_3$, and $B_2$ and $B_3$ are both hydrogen and the values of $R^{43a}$, $R^{4b}$, $R^{4c}$, $R^{4d}$ and $R^8$ are given in Table 1.

Table DCLII provides 782 compounds of formula Iaz wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLIII provides 782 compounds of formula Iba wherein $A_1$ is hydrogen, $B_1$ and $B_4$ are both $CH_3$, and $B_2$ and $B_3$ are both hydrogen and the values of $R^4$, $R^{4b}$, $R^{4c}$, $R^{4d}$ and $R^8$ are given in Table 1.

Table DCLIV provides 782 compounds of formula Ibb wherein $A_1$ is hydrogen, $B_1$ and $B_4$ are both $CH_3$, and $B_2$ and $B_3$ are both hydrogen and the values of $R^{43a}$, $R^{4b}$, $R^{4c}$, $R^{4d}$ and $R^8$ are given in Table 1.

Table DCLV provides 782 compounds of formula Ibc wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLVI provides 782 compounds of formula Ibd wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLVII provides 782 compounds of formula Ibe wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLVIII provides 782 compounds of formula Ibf wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLIX provides 782 compounds of formula Ibg wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLX provides 782 compounds of formula Ibh wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXI provides 782 compounds of formula Ibi wherein $A_1$ is hydrogen, $B_1$ and $B_4$ are both $CH_3$, and $B_2$ and $B_3$ are both hydrogen and the values of $R^4$, $R^{4b}$, $R^{4c}$, $R^{4d}$ and $R^8$ are given in Table 1.

Table DCLXII provides 782 compounds of formula Ibj wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXIII provides 782 compounds of formula Ibk wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXIV provides 782 compounds of formula Ibl wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXV provides 782 compounds of formula Ibm wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXVI provides 782 compounds of formula Ibn wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCLXVII provides 782 compounds of formula Ibo wherein $A_1$ is hydrogen, $B_1$ and $B_4$ are both $CH_3$, and $B_2$ and $B_3$ are both hydrogen and the values of $R^{4a}$, $R^{4b}$, $R^{4c}$, $R^{4d}$ and $R^8$ are given in Table 1.

Table DCCI provides 782 compounds of formula Ia wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCII provides 782 compounds of formula Ib wherein $A_1$ is hydrogen, $B_1$, $B_2$, $B_3$ and $B_4$ are all $CH_3$ and the values of $R^4$, $R^{4b}$, $R^{4c}$, $R^{4d}$ and $R^8$ are given in Table 1.

Table DCCII provides 782 compounds of formula Ic wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^5$ are given in Table 1.

Table DCCIV provides 782 compounds of formula Id wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCV provides 782 compounds of formula Ie wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCVI provides 782 compounds of formula If wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCVII provides 782 compounds of formula Ig wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^9$ are given in Table 1.

Table DCCVIII provides 782 compounds of formula Ih wherein $A_1$ is hydrogen $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCIX provides 782 compounds of formula Ii wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCX provides 782 compounds of formula Ij wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXI provides 782 compounds of formula Ik wherein $A_1$ is hydrogen $B_1$, $B_2$, $B_3$ and $B_4$ are all $CH_3$ and the values of $R^4$, $R^{4b}$, $R^{4c}$, $R^{4d}$ and $R^8$ are given in Table 1.

Table DCCXII provides 782 compounds of formula Il wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXIII provides 782 compounds of formula Im wherein $A_1$ is hydrogen, $B_1$, $B_2$, $B_3$ and $B_4$ are all $CH_3$ and the values of $R^{4a}$, $R^{4c}$, $R^{4d}$ and $R^8$ are given in Table 1

Table DCCXIV provides 782 compounds of formula In wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXV provides 782 compounds of formula Io wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXVI provides 782 compounds of formula Ip wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXVII provides 782 compounds of formula Iq wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXVIII provides 782 compounds of formula kr wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLX provides 782 compounds of formula Is wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXX provides 782 compounds of formula It wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXI provides 782 compounds of formula Iu wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXII provides 782 compounds of formula Iv wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXIII provides 782 compounds of formula Iw wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXIV provides 782 compounds of formula Ix wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXV provides 782 compounds of formula Iy wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXVI provides 782 compounds of formula Iz wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXVII provides 782 compounds of formula Iaa wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXVIII provides 782 compounds of formula Iab wherein $A_1$ is hydrogen, $B_1$, $B_2$, $B_3$ and $B_4$ are all $CH_3$ and the values of $R^4$, $R^{4b}$, $R^{4c}$, $R^{4d}$ and $R^8$ are given in Table 1.

Table DCCXXIX provides 782 compounds of formula Iac wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXX provides 782 compounds of formula Iad wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^5$ are given in Table 1.

Table DCCXXXI provides 782 compounds of formula Iae wherein $A_1$ is hydrogen, $B_1$, $B_2$, $B_3$ and $B_4$ are all $CH_3$ and the values of $R^{4c}$, $R^{4b}$, $R^{4c}$, $R^{4d}$ and $R^8$ are given in Table 1.

Table DCCXXXII provides 782 compounds of formula Iaf wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXM provides 782 compounds of formula Iag wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXIV provides 782 compounds of formula Iah wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXV provides 782 compounds of formula Iai wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXVI provides 782 compounds of formula Iaj wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXVII provides 782 compounds of formula Iak wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXVIII provides 782 compounds of formula Ial wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXXXIX provides 782 compounds of formula Iam wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^9$ are given in Table 1.

Table DCCXL provides 782 compounds of formula Ian wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLI provides 782 compounds of formula Iao wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLII provides 782 compounds of formula Iap wherein $A_1$ is hydrogen, $B_1$, $B_2$, $B_3$ and $B_4$ are all $CH_3$ and the values of $R^{4c}$, $R^{4b}$, $R^{4c}$, $R^{4d}$ and $R^8$ are given in Table 1.

Table DCCXLIII provides 782 compounds of formula Iaq wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLIV provides 782 compounds of formula Iar wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLV provides 782 compounds of formula Ias wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLVI provides 782 compounds of formula Iat wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLVII provides 782 compounds of formula Iau wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLVIE provides 782 compounds of formula Iav wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCXLIX provides 782 compounds of formula Iaw wherein $A_1$ is hydrogen, $B_1$, $B_2$, $B_3$ and $B_4$ are all $CH_3$ and the values of $R^4$, $R^{4b}$, $R^{4c}$, $R^{4d}$ and $R^8$ are given in Table 1.

Table DCCL provides 782 compounds of formula Iax wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCLI provides 782 compounds of formula Iay wherein $A_1$ is hydrogen, $B_1$, $B_2$, $B_3$ and $B_4$ are all $CH_3$ and the values of $R^{4a}$, $R^{4b}$, $R^{4c}$, $R^{4d}$ and $R^8$ are given in Table 1.

Table DCCLII provides 782 compounds of formula Iaz wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLIII provides 782 compounds of formula Iba wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLIV provides 782 compounds of formula Ibb wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLV provides 782 compounds of formula Ibc wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLVI provides 782 compounds of formula Ibd wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLVII provides 782 compounds of formula Ibe wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLVIII provides 782 compounds of formula Ibf wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLLX provides 782 compounds of formula Ibg wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLX provides 782 compounds of formula Ibh wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLXI provides 782 compounds of formula Ibi wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLXII provides 782 compounds of formula Ibj wherein $A_1$ is hydrogen $B_1, B_2, B_3$ and $B_4$ are all $CH_3$ and the values of $R^{4a}, R^{4b}, R^{4c}, R^{4d}$ and $R^8$ are given in Table 1.

Table DCCLXIII provides 782 compounds of formula Ibk wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLXIV provides 782 compounds of formula Ibl wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLXV provides 782 compounds of formula Ibm wherein $A_1$ is hydrogen, $B_1, B_2, B_3$ and $B_4$ are all $CH_3$ and the values of $R^4, R^{4b}, R^{4c}, R^{4d}$ and $R^8$ are given in Table 1.

Table DCCLXVI provides 782 compounds of formula Ibn wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCLXVII provides 782 compounds of formula Ibo wherein $A_1$ is hydrogen, $B_1, B_2, B_3$ and $B_4$ are all $CH_3$ and the values of $R^{4a}, R^{4b}, R^{4c}, R^{4d}$ and $R^8$ are given in Table 1.

Table DCCCI provides 782 compounds of formula Ia wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCII provides 782 compounds of formula Ib wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCIII provides 782 compounds of formula Ic wherein $A_1$ is hydrogen, $B_1$ and $B_2$ are together =O and $B_3$ and $B_4$ are both hydrogen and the values of $R^{4c}, R^{4b}, R^{4c}, R^{4d}$ and $R^8$ are given in Table 1.

Table DCCCIV provides 782 compounds of formula Id wherein $A_1$ is hydrogen, $B_1$ and $B_2$ are together =O and $B_3$ and $B_4$ are both hydrogen and the values of $R^4, R^{4b}, R^{4c}, R^{4d}$ and $R^8$ are given in Table 1.

Table DCCCV provides 782 compounds of formula Ie wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCVI provides 782 compounds of formula If wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCVII provides 782 compounds of formula Ig wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCVII provides 782 compounds of formula Ih wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCIX provides 782 compounds of formula Ii wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCX provides 782 compounds of formula Ij wherein $A_1$ is hydrogen, $B_1$ and $B_2$ are together =O and $B_3$ and $B_4$ are both hydrogen and the values of $R^{4a}— R^{4b}, R^{4c}, R^{4d}$ and $R^8$ are given in Table 1.

Table DCCCXI provides 782 compounds of formula Ik wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXII provides 782 compounds of formula Il wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXIII provides 782 compounds of formula Im wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXIV provides 782 compounds of formula In wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXV provides 782 compounds of formula Io wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXVI provides 782 compounds of formula Ip wherein $A_1$ is hydrogen, $B_1$ and $B_2$ are together =O and $B_3$ and $B_4$ are both hydrogen and the values of $R^4, R^{4b}, R^{4c}, R^{4d}$ and $R^8$ are given in Table 1.

Table DCCCXVII provides 782 compounds of formula Iq wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXVIII provides 782 compounds of formula Ir wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXIX provides 782 compounds of formula Is wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXX provides 782 compounds of formula It wherein $A_1$ is hydrogen, $B_1$ and $B_2$ are together =O and $B_3$ and $B_4$ are both hydrogen and the values of $R^{4a}, R^{4b}, R^{4c}, R^{4d}$ and $R^8$ are given in Table 1.

Table DCCCXXI provides 782 compounds of formula Iu wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXII provides 782 compounds of formula Iv wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXIII provides 782 compounds of formula Iw wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXIV provides 782 compounds of formula Ix wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXV provides 782 compounds of formula Iy wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXVI provides 782 compounds of formula Iz wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXVII provides 782 compounds of formula Iaa wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXVIII provides 782 compounds of formula Iab wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXIX provides 782 compounds of formula Iac wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXX provides 782 compounds of formula Iad wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXI provides 782 compounds of formula Iae wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXII provides 782 compounds of formula Iaf wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXIII provides 782 compounds of formula Iag wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXIV provides 782 compounds of formula Iah wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXV provides 782 compounds of formula Iai wherein $A_1$ is hydrogen, $B_1$ and $B_2$ are together =O and $B_3$ and $B_4$ are both hydrogen and the values of $R^4$, $R^{4b}$, $R^{4c}$, $R^{4d}$ and $R^8$ are given in Table 1.

Table DCCCXXXVI provides 782 compounds of formula Iaj wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXVII provides 782 compounds of formula Iak wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXVIII provides 782 compounds of formula Ial wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXXXIX provides 782 compounds of formula Iam wherein $A_1$ is hydrogen, $B_1$ and $B_2$ are together =O and $B_3$ and $B_4$ are both hydrogen and the values of $R^{4c}$, $R^{4b}$, $R^{4c}$, $R^{4d}$ and $R^8$ are given in Table 1.

Table DCCCXL provides 782 compounds of formula Ian wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLI provides 782 compounds of formula Iao wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLII provides 782 compounds of formula Iap wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLIII provides 782 compounds of formula Iaq wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLIV provides 782 compounds of formula Iar wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLV provides 782 compounds of formula Ias wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLVI provides 782 compounds of formula Iat wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLVII provides 782 compounds of formula Iau wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLVIII provides 782 compounds of formula Iav wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCXLIX provides 782 compounds of formula Iaw wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCL provides 782 compounds of formula Iax wherein $A_1$ is hydrogen, $B_1$ and $B_2$ are together =O and $B_3$ and $B_4$ are both hydrogen and the values of $R^{4c}$, $R^{4b}$, $R^{4c}$, $R^{4d}$ and $R^8$ are given in Table 1.

Table DCCCLI provides 782 compounds of formula Iay wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLII provides 782 compounds of formula Iaz wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLIII provides 782 compounds of formula Iba wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLIV provides 782 compounds of formula Ibb wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLV provides 782 compounds of formula Ibc wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLVI provides 782 compounds of formula Ibd wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLVII provides 782 compounds of formula Ibe wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLVIII provides 782 compounds of formula Ibf wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLIX provides 782 compounds of formula Ibg wherein $A_1$ is hydrogen, $B_1$ and $B_2$ are together =O and $B_3$ and $B_4$ are both hydrogen and the values of $R^4$, $R^{4b}$, $R^{4c}$, $R^{4d}$ and $R^8$ are given in Table 1.

Table DCCCLX provides 782 compounds of formula Ibh wherein $A_1$ is hydrogen, $B_1$ and $B_2$ are together =O and $B_3$ and $B_4$ are both hydrogen and the values of $R^{4c}$, $R^{4b}$, $R^{4c}$, $R^{4d}$ and $R^8$ are given in Table 1.

Table DCCCLXI provides 782 compounds of formula Ibi wherein $A_1$ is hydrogen, $B_1$ and $B_2$ are together =O and $B_3$ and $B_4$ are both hydrogen and the values of $R^{4c}$, $R^{4b}$, $R^{4c}$, $R^{4d}$ and $R^8$ are given in Table 1.

Table DCCCLXII provides 782 compounds of formula Ibj wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLXIII provides 782 compounds of formula Ibk wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLXIV provides 782 compounds of formula Ibl wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLXV provides 782 compounds of formula Ibm wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLXVI provides 782 compounds of formula Ibn wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table DCCCLXVII provides 782 compounds of formula Ibo wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table CMI provides 782 compounds of formula Ia wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMII provides 782 compounds of formula Ib wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMIII provides 782 compounds of formula Ic wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMIV provides 782 compounds of formula Id wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMV provides 782 compounds of formula Ie wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMVI provides 782 compounds of formula If wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMVII provides 782 compounds of formula Ig wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMVIII provides 782 compounds of formula Ih wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMIX provides 782 compounds of formula Ii wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMX provides 782 compounds of formula Ij wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXI provides 782 compounds of formula Ik wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXII provides 782 compounds of formula Il wherein $A_1$ and $B_1$ together form a bond and $B_2$, $B_3$ and $B_4$ are all hydrogen and the values of $R^4$, $R^{4b}$, $R^{4c}$, $R^{4d}$ and $R^8$ are given in Table 1.

Table CMXIII provides 782 compounds of formula Im wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXIV provides 782 compounds of formula In wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXV provides 782 compounds of formula Io wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXVI provides 782 compounds of formula Ip wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXVII provides 782 compounds of formula Iq wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXVIII provides 782 compounds of formula Ir wherein $A_1$ and $B_1$ together form a bond and $B_2$, $B_3$ and $B_4$ are all hydrogen and the values of $R^{4a}$, $R^{4c}$, $R^{4d}$ and $R^8$ are given in Table 1.

Table CMXIX provides 782 compounds of formula Is wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXX provides 782 compounds of formula It wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXI provides 782 compounds of formula Iu wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXII provides 782 compounds of formula Iv wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXIII provides 782 compounds of formula Iw wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXIV provides 782 compounds of formula Ix wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXV provides 782 compounds of formula Iy wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXVI provides 782 compounds of formula Iz wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXVII provides 782 compounds of formula Iaa wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXVIII provides 782 compounds of formula Iab wherein $A_1$ and $B_1$ together form a bond and $B_2$, $B_3$ and $B_4$ are all hydrogen and the values of $R^4$, $R^{4b}$, $R^{4c}$, $R^{4d}$ and $R^8$ are given in Table 1.

Table CMXXIX provides 782 compounds of formula Iac wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXX provides 782 compounds of formula Iad wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table CMXXXI provides 782 compounds of formula Iae wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXII provides 782 compounds of formula Iaf wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXIII provides 782 compounds of formula Iag wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXIV provides 782 compounds of formula Iah wherein $A_1$ and $B_1$ together form a bond and $B_2$, $B_3$ and $B_4$ are all hydrogen and the values of $R^{4c}$, $R^{4b}$, $R^{4c}$, $R^{4d}$ and $R^8$ are given in Table 1.

Table CMXXXV provides 782 compounds of formula Iai wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXVI provides 782 compounds of formula Iaj wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXVII provides 782 compounds of formula Iak wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXVIII provides 782 compounds of formula Ial wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXXXIX provides 782 compounds of formula Iam wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXL provides 782 compounds of formula Ian wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLI provides 782 compounds of formula Iao wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLII provides 782 compounds of formula Iap wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLIII provides 782 compounds of formula Iaq wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLIV provides 782 compounds of formula Iar wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLV provides 782 compounds of formula Ias wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLVI provides 782 compounds of formula Iat wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLVII provides 782 compounds of formula Iau wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLVIII provides 782 compounds of formula Iav wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMXLIX provides 782 compounds of formula Iaw wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CML provides 782 compounds of formula Iax wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLI provides 782 compounds of formula Iay wherein $A_1$ and $B_1$ together form a bond and $B_2$, $B_3$ and $B_4$ are all hydrogen and the values of $R^4$, $R^{4b}$, $R^{4c}$, $R^{4d}$ and $R^8$ are given in Table 1.

Table CMLII provides 782 compounds of formula Iaz wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLIII provides 782 compounds of formula Iba wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLIV provides 782 compounds of formula Ibb wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLV provides 782 compounds of formula Ibc wherein $A_1$ and $B_1$ together form a bond and $B_2$, $B_3$ and $B_4$ are all hydrogen and the values of $R^4$, $R^{4b}$, $R^{4c}$, $R^{4d}$ and $R^8$ are given in Table 1.

Table CMLVI provides 782 compounds of formula Ibd wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLVII provides 782 compounds of formula Ibe wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLVIII provides 782 compounds of formula Ibf wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLIX provides 782 compounds of formula Ibg wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLX provides 782 compounds of formula Ibh wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXI provides 782 compounds of formula Ibi wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXII provides 782 compounds of formula Ibj wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXIII provides 782 compounds of formula Ibk wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXIV provides 782 compounds of formula Ibl wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXV provides 782 compounds of formula Ibm wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table CMLXVI provides 782 compounds of formula Ibn wherein $A_1$ and $B_1$ together form a bond and $B_2$, $B_3$ and $B_4$ are all hydrogen and the values of $R^4$, $R^{4b}$, $R^{4c}$, $R^{4d}$ and $R^8$ are given in Table 1.

Table CMLXVII provides 782 compounds of formula Ibo wherein $A_1$ and $B_1$ together form a bond and $B_2$, $B_3$ and $B_4$ are all hydrogen and the values of $R^{4a}$, $R^{4b}$, $R^{4c}$, $R^{4d}$ and $R^8$ are given in Table 1.

Table MI provides 782 compounds of formula Ia wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MII provides 782 compounds of formula Ib wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MIII provides 782 compounds of formula Ic wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MIV provides 782 compounds of formula Id wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MV provides 782 compounds of formula Ie wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MVI provides 782 compounds of formula If wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MVII provides 782 compounds of formula Ig wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MVIII provides 782 compounds of formula Ih wherein $A_1$ and $B_1$ together form —$CH_1$— and $B_2$, $B_3$ and $B_4$ are all hydrogen and the values of $R^{4a}$, $R^{4b}$, $R^{4c}$, $R^{4d}$ and $R^8$ are given in Table 1.

Table MIX provides 782 compounds of formula Ii wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MX provides 782 compounds of formula Ij wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXI provides 782 compounds of formula Ik wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXII provides 782 compounds of formula Il wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXIII provides 782 compounds of formula Im wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXIV provides 782 compounds of formula In wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXV provides 782 compounds of formula Io wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXVI provides 782 compounds of formula Ip wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXVII provides 782 compounds of formula Iq wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXVIII provides 782 compounds of formula Ir wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXIX provides 782 compounds of formula Is wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXX provides 782 compounds of formula It wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXI provides 782 compounds of formula Iu wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXII provides 782 compounds of formula Iv wherein $A_1$ and $B_1$ together form —$CH_2$— and $B_2$, $B_3$ and $B_4$ are all hydrogen and the values of $R^4$, $R^{4b}$, $R^{4c}$, $R^{4d}$ and $R^8$ are given in Table 1.

Table MXXIII provides 782 compounds of formula Iw wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXIV provides 782 compounds of formula Ix wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXV provides 782 compounds of formula Iy wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXVI provides 782 compounds of formula Iz wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXVII provides 782 compounds of formula Iaa wherein $A_1$ and B together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXVIII provides 782 compounds of formula Iab wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXIX provides 782 compounds of formula Iac wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXX provides 782 compounds of formula Iad wherein $A_1$ is hydrogen, $B_1$ and $B_2$ are together =O and $B_3$ and $B_4$ are both hydrogen and the values of $R^{4a}$, $R^{4b}$, $R^{4c}$, $R^{4d}$ and $R^8$ are given in Table 1.

Table MXXXI provides 782 compounds of formula Iae wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXII provides 782 compounds of formula Iaf wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXIII provides 782 compounds of formula Iag wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXIV provides 782 compounds of formula Iah wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXV provides 782 compounds of formula Iai wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXVI provides 782 compounds of formula Iaj wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXVII provides 782 compounds of formula Iak wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXVIII provides 782 compounds of formula Ial wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXXXIX provides 782 compounds of formula Iam wherein $A_1$ and $B_1$ together form —$CH_2$— and $B_2$, $B_3$ and $B_4$ are all hydrogen and the values of $R^4$, $R^{4b}$, $R^{4c}$, $R^{4d}$ and $R^8$ are given in Table 1.

Table MXL provides 782 compounds of formula Ian wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLI provides 782 compounds of formula Iao wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLII provides 782 compounds of formula Iap wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLIII provides 782 compounds of formula Iaq wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLIV provides 782 compounds of formula Iar wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLV provides 782 compounds of formula Ias wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLVI provides 782 compounds of formula Iat wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLVII provides 782 compounds of formula Iau wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLVIII provides 782 compounds of formula Iav wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MXLIX provides 782 compounds of formula Iaw wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table ML provides 782 compounds of formula Iax wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLI provides 782 compounds of formula Iay wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLII provides 782 compounds of formula Iaz wherein $A_1$ and $B_1$ together form —$CH_2$— and $B_2$, $B_3$ and $B_4$ are all hydrogen and the values of $R^4$, $R^{4b}$, $R^{4c}$, $R^{4d}$ and $R^8$ are given in Table 1.

Table MLIII provides 782 compounds of formula Iba wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLIV provides 782 compounds of formula Ibb wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLV provides 782 compounds of formula Ibc wherein $A_1$ and $B_1$ together form —$CH_2$— and $B_2$, $B_3$ and $B_4$ are all hydrogen and the values of $R^4$, $R^{4b}$, $R^{4c}$, $R^{4d}$ and $R^8$ are given in Table 1.

Table MLVI provides 782 compounds of formula Ibd wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLVII provides 782 compounds of formula Ibe wherein $A_1$ and B) together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLVIII provides 782 compounds of formula Ibf wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLIX provides 782 compounds of formula Ibg wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLX provides 782 compounds of formula Ibh wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXI provides 782 compounds of formula Ibi wherein $A_1$ and $B_1$ together form —$CH_2$— and $B_2$, $B_3$ and $B_4$ are all hydrogen and the values of $R^4$, $R^{4b}$, $R^{4c}$, $R^{4d}$ and $R^8$ are given in Table 1.

Table MLXII provides 782 compounds of formula Ibj wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXIII provides 782 compounds of formula Ibk wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXIV provides 782 compounds of formula Ibl wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXV provides 782 compounds of formula Ibm wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXVI provides 782 compounds of formula Ibn wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MLXVII provides 782 compounds of formula Ibo wherein $A_1$ and $B_1$ together form —$CH_2$— and $B_2$, $B_3$ and $B_4$ are all hydrogen and the values of $R^{4a}$, $R^{4b}$, $R^{4c}$, $R^{4d}$ and $R^8$ are given in Table 1.

Table MCI provides 782 compounds of formula Ia wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCII provides 782 compounds of formula Tb wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCIII provides 782 compounds of formula Ic wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCIV provides 782 compounds of formula Id wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCV provides 782 compounds of formula Ie wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCVI provides 782 compounds of formula If wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCVII provides 782 compounds of formula Ig wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCVIII provides 782 compounds of formula Ih wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCIX provides 782 compounds of formula Ii wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCX provides 782 compounds of formula Ij wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^5$ are given in Table 1.

Table MCXI provides 782 compounds of formula Ik wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCXII provides 782 compounds of formula Il wherein $A_1$ is hydrogen, $B_1$ and $B_3$ together form a group —$CH_2$—$CH_2$—, and $B_2$ and $B_4$ are both hydrogen and the values of $R^{4a}$, $R^{4b}$, $R^{4c}$, $R^{4d}$ and $R^8$ are given in Table 1.

Table MCXIII provides 782 compounds of formula Im wherein $A_1$ is hydrogen, $B_1$ and $B_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXIV provides 782 compounds of formula In wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXV provides 782 compounds of formula Io wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXVI provides 782 compounds of formula Ip wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXVII provides 782 compounds of formula Iq wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXVIII provides 782 compounds of formula Ir wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXIX provides 782 compounds of formula Is wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXX provides 782 compounds of formula It wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXI provides 782 compounds of formula Iu wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXII provides 782 compounds of formula Iv wherein A$_1$ is hydrogen, B$_1$ and B$_3$ together form a group —CH$_2$—CH$_2$—, and B$_2$ and B$_4$ are both hydrogen and the values of R$^{4c}$, R$^{4b}$, R$^{4c}$, R$^{4d}$ and R$^8$ are given in Table 1.

Table MCXXIII provides 782 compounds of formula Iw wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXIV provides 782 compounds of formula Ix wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXV provides 782 compounds of formula Iy wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXVI provides 782 compounds of formula Iz wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXVII provides 782 compounds of formula Iaa wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXVIII provides 782 compounds of formula Iab wherein A$_1$ is hydrogen, B$_1$ and B$_3$ together form a group —CH$_2$—CH$_2$—, and B$_2$ and B$_4$ are both hydrogen and the values of R$^{4a}$R$^{4b}$, R$^{4c}$, R$^{4d}$ and R$^8$ are given in Table 1.

Table MCXXIX provides 782 compounds of formula Iac wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXX provides 782 compounds of formula Iad wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXI provides 782 compounds of formula Iae wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXII provides 782 compounds of formula Iaf wherein A$_1$ is hydrogen, B$_1$ and B$_3$ together fonr a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXIII provides 782 compounds of formula Iag wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXIV provides 782 compounds of formula Iah wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXV provides 782 compounds of formula Iai wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXXXVI provides 782 compounds of formula Iaj wherein A$_1$ is hydrogen, B$_1$ and B$_3$ together form a group —CH$_2$—CH$_2$—, and B$_2$ and B$_4$ are both hydrogen and the values of R$^{4a}$R$^{4b}$, R$^{4c}$, R$^{4d}$ and R$^5$ are given in Table 1.

Table MCXXXVII provides 782 compounds of formula Iak wherein A$_1$ is hydrogen, B$_1$ and B$_3$ together form a group —CH$_2$—CH$_2$—, and B$_2$ and B$_4$ are both hydrogen and the values of R$^{4a}$R$^{4b}$, R$^{4c}$, R$^{4d}$ and R$^8$ are given in Table 1.

Table MCXXXVIII provides 782 compounds of formula Ial wherein A$_1$ is hydrogen, B$_1$ and B$_3$ together form a group —CH$_2$—CH$_2$—, and B$_2$ and B$_4$ are both hydrogen and the values of R$^{4a}$R$^{4b}$, R$^{4c}$, R$^{4d}$ and R$^5$ are given in Table 1.

Table MCXXXIX provides 782 compounds of formula Iam wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXL provides 782 compounds of formula Ian wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLI provides 782 compounds of formula Iao wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLII provides 782 compounds of formula Iap wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLIII provides 782 compounds of formula Iaq wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLIV provides 782 compounds of formula Iar wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLV provides 782 compounds of formula Ias wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLVI provides 782 compounds of formula Iat wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLVII provides 782 compounds of formula Iau wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLVIII provides 782 compounds of formula Iav wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCXLIX provides 782 compounds of formula Iaw wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCL provides 782 compounds of formula Iax wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLI provides 782 compounds of formula Iay wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLII provides 782 compounds of formula m/z wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLIII provides 782 compounds of formula Iba wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLIV provides 782 compounds of formula Ibb wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLV provides 782 compounds of formula Ibc wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLVI provides 782 compounds of formula Ibd wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLVII provides 782 compounds of formula Tbe wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLVIII provides 782 compounds of formula Ibf wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLIX provides 782 compounds of formula Ibg wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLX provides 782 compounds of formula Ibh wherein A$_1$ is hydrogen, B$_1$ and B$_3$ together form a group —CH$_2$—CH$_2$—, and B$_2$ and B$_4$ are both hydrogen and the values of R$^4$, R$^{4b}$, R$^{4c}$, R$^{4d}$ and R$^8$ are given in Table 1.

Table MCLXI provides 782 compounds of formula Ibi wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLXII provides 782 compounds of formula Ibj wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLXIII provides 782 compounds of formula Ibk wherein A$_1$ is hydrogen, B$_1$ and B$_3$ together form a group —CH$_2$—CH$_2$—, and B$_2$ and B$_4$ are both hydrogen and the values of R$^{4c}$, R$^{4b}$, R$^{4c}$, R$^{4d}$ and R$^8$ are given in Table 1.

Table MCLXIV provides 782 compounds of formula Ibl wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLXV provides 782 compounds of formula Ibm wherein A$_1$ is hydrogen, B$_1$ and B$_3$ together form a group —CH$_2$—CH$_2$—, and B$_2$ and B$_4$ are both hydrogen and the values of R$^{4c}$, R$^{4b}$, R$^{4c}$, R$^{4d}$ and R$^8$ are given in Table 1.

Table MCLXVI provides 782 compounds of formula Ibn wherein A$_1$ is hydrogen, B$_1$ and B$_3$ together form a group —CH$_2$—CH$_2$—, and B$_2$ and B$_4$ are both hydrogen and the values of R$^{4a}$, R$^{4b}$, R$^{4c}$, R$^{4d}$ and R$^8$ are given in Table 1.

Table MCLXVII provides 782 compounds of formula Ibo wherein A$_1$ is hydrogen, B$_1$ and B$_3$ together form a group —CH$_2$—CH$_2$—, and B$_2$ and B$_4$ are both hydrogen and the values of R$^4$, R$^{4b}$, R$^{4c}$, R$^{4d}$ and R$^8$ are given in Table 1.

Mass spectra data were obtained for selected compounds of Tables I to MCLXVII using LCMS: LC5: 254 nm—gradient 10% A to 100% B A=H2O+0.01% HCOOH B=CH3CN/CH3OH+0.01% HCOOH positive electrospray 150-1000 m/z.

The data are shown in Table 2.

TABLE 2

| Compound No | M.p. (° C.) | LCMS (Ret. Time, min) | MS data |
|---|---|---|---|
| III. 49 | 91-93 | 2.37 | 526/528 |
| CIII. 49 | 110 | 2.26 | 528/530 |
| CCIII. 49 | 96-97 | 3.22 | 530/532 |
| CCCIV. 49 | 100-101 | 4.01 | 548 |

The compounds of the invention may be synthesised by various methods. For example the compounds of formula 1 may be synthesised as described in Scheme 1.

Thus a compound of formula 1 may be synthesised from a compound of formula 2 by reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound. The intermediate thus formed reacts with an alkylating agent of the formula R$^8$-L, where L is chloride, bromide, iodide or a sulfonate (e.g. mesylate or tosylate) or similar leaving group at a temperature of between ambient temperature and 100° C., typically ambient temperature, in an organic solvent such as acetonitrile, dimethylformamide, dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

Alternatively a compound of formula 2, after removal of the t-butoxycarbonyl protecting group as described above, may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy)borohydride, sodium cyanoborohydride or such like, to produce a compound of formula 1 where R8 is CH$_2$—R.

In an alternative method compounds of formula 1 may be obtained from compounds of formula 6 by reaction with a suitable electrophilic species. Compounds of formula 1 where Y is a carbonyl group may be formed by the reaction of compounds of formula 6 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 1 where Y is a carbonyl group and R1 is an amino substituent of formula R'—NH— may be formed by the reaction of compounds of formula 6 with an isocyanate of formula R'—N=C=O under similar conditions. Compounds of formula 1 where Y is a group of formula S(O)$_q$ may be formed from compounds of formula 6 by treatment with compounds of formula of R1-S(O)$_q$—Cl under similar conditions. Compounds of formula 1 where Y is a thiocarbonyl group and R1 is an amino substituent of formula R'—NH— may be formed by the reaction of compounds of formula 6 with an isothiocyanate of formula R'—N=C=S under similar conditions. Alternatively compounds of formula I where Y is a thiocarbonyl group and R1 is a carbon substituent may be formed by treatment of compounds of formula 1 where Y is a carbonyl group and R1 is a carbon substituent with a suitable thionating agent such as Lawesson's reagent.

In the above procedures, acid derivatives of the formula R1-C(O)—Z, isocyanates of formula R'—N=C=O, isothiocyanates of formula R'—N=C=S and sulfur electrophiles of formula R1-S(O)$_q$—Cl are either known compounds or may be formed from known compounds by known methods by a person skilled in the art.

A compound of formula 2 may be obtained from a compound of formula 3 by reaction with a suitable electrophilic species, as described above.

Compounds of formula 3 may be obtained by reacting compounds of formula 4 with compounds of formula 10 at a temperature of between 0° C. and 100° C. in an organic solvent such as dichloromethane, chloroform or 1,2-dichloroethane in the presence of an acid such as hydrochloric acid or trifluoroacetic acid and optionally a co-solvent such as water, methanol or ethanol. The intermediates formed are subsequently treated with a reducing agent such as sodium borohydride, sodium (triacetoxy)borohydride, sodium cyanoborohydride, triethylsilane or similar at ambient temperature in organic solvent such as ethanol or chloroform or with a nucleophile R3-M (where M is a metallic species; R3-M is for example a Grignard reagent). The basic procedure is described in Tetrahedron (1997), 53, 10983-10992.

Similarly, compounds of formula 6 may be synthesised by reacting compounds of formula 7 with compounds of formula 10 using the conditions described above.

Compounds of formula 4 may be obtained from compounds of formula 5 by reaction with a 1-alkoxy substituted phosphonium salt of formula 9 such as methoxymethyl(triphenyl)phosphonium chloride and a base such as potassium tert-butoxide at a temperature of 0° C. to 80° C. in tetrahydrofuran.

Similarly, compounds of formula 7 may be synthesised from compounds of formula 8 using the conditions described above.

Compounds of formula 5, 8 and 10 are either known compounds or may be formed from known compounds by known methods by a person skilled in the art.

Certain compounds of formula 2, 3 and 6 are novel and as such form a further aspect of the invention.

SCHEME I

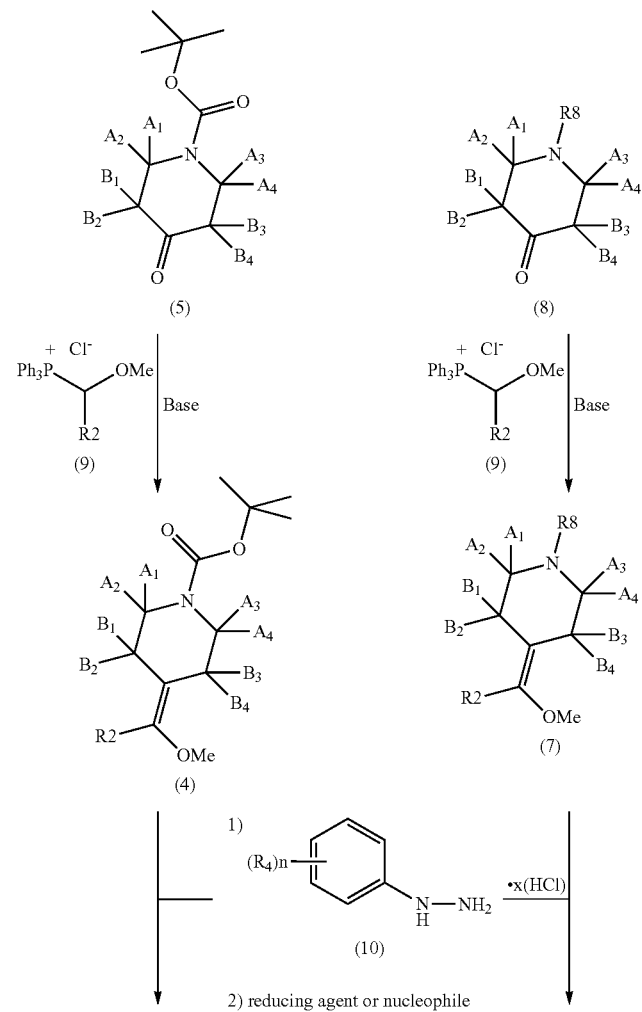

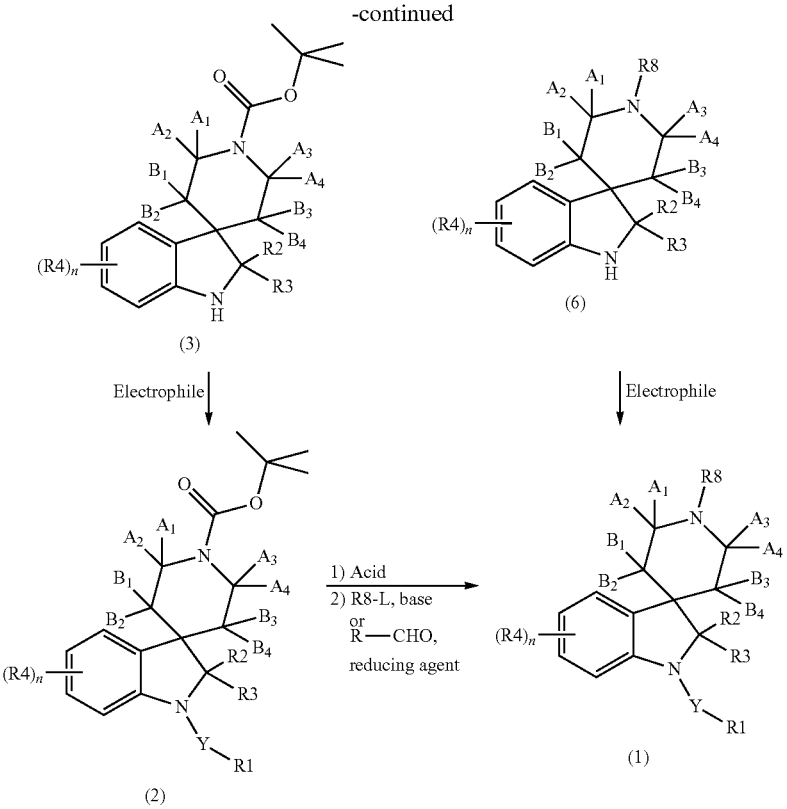

In an alternative method a compound of formula 1 wherein $A_1$, $A_2$, $A_3$, $A_4$, $B_2$, $B_3$ and $B_4$ are Et and $B_1$ is OH may be obtained from a compound of formula 12 by removal of the t-butoxycarbonyl protecting group and reaction with an alkylating agent R8-L as described previously. A Compound of formula 12 may be obtained from an intermediate of formula 11 by reaction with an hydroborating agent such as borane in an organic solvent such as dichloromethane or tetrahydrofuran at a temperature of between 0° C. to 80° C., followed by treatment with an oxidising agent such as hydrogen peroxide in the presence of water and a base such as sodium hydroxide at a temperature of between 0° C. to 100° C. (Scheme 2).

The skilled person will readily recognise that it is possible to convert one compound of formula 12 to other compounds of formula 1.

SCHEME 2

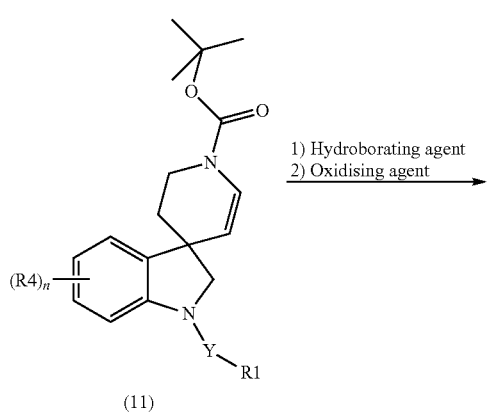

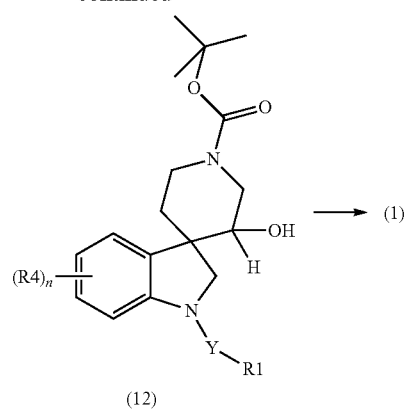

In another alternative method, a compound of formula 11 may be reacted with a suitable fluorinating species, such as Selectfluor®, followed by reaction with a reducing agent such as triethylsilane in the presence of an acid such as trifluoroacetic acid to provide a compound of formula 13 or a compound of formula 14. Compounds of formula 13 (or 14) may be converted into compounds of formula I wherein $A_1$, $A_2$, $A_3$, $A_4$, $B_2$, $B_3$ and $B_4$ are H and $B_1$ is F (i.e. $A_1$, $A_2$, $A_3$, $A_4$, $B_3$ and $B_4$ are H, $B_1$ and $B_2$ are F) by reaction with an alkylating agent of the formula R8-L as described previously (Scheme 3).

SCHEME 3

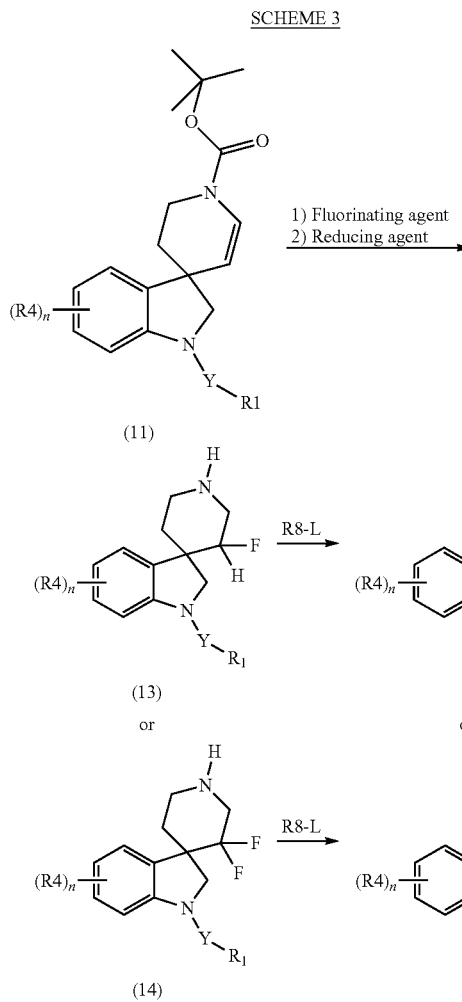

Compounds of formula 11 may be synthesised by the method outlined on Scheme 4.

Thus a compound of formula 11 may be synthesised from a compound of formula 15 by reacting with an electrophilic species as described previously.

A compound of formula 15 may be prepared from a compound of formula 16 by treatment with a suitable base such as potassium carbonate at a temperature of between 0° C. to 80° C. in an organic solvent such as methanol or ethanol in combination with water.

A compound of formula 16 may be synthesised by cyclising a compound of formula 17 under Heck conditions, typically in the presence of a catalyst such as palladium(II) acetate, optionally a ligand such as triphenylphosphine or/and an additive such as tetrabutylammonium bromide and a base such as triethylamine in an organic solvent such as tetrahydrofuran, acetonitrile, dimethylformamide, N-methyl-pyrrolidinone or dimethylacetamide at a temperature of between 20° C. to 140° C.

Compounds of formula 17 may be synthesised by coupling compounds of formula 18 with the known alcohol 19 (*J. Org. Chem.* 2001, 66, 5545-5551) under Mitsunobu conditions, typically using a phosphine such as triphenylphosphine and an azo compound such as diethylazodicarboxylate or diisopropylazodicarboxylate in an organic solvent such as tetrahydrofuran or toluene at a temperature of between 0° C. to 80° C.

Compounds of formula 18 are either known compounds or may be formed from known compounds by known methods by a person skilled in the art.

SCHEME 4

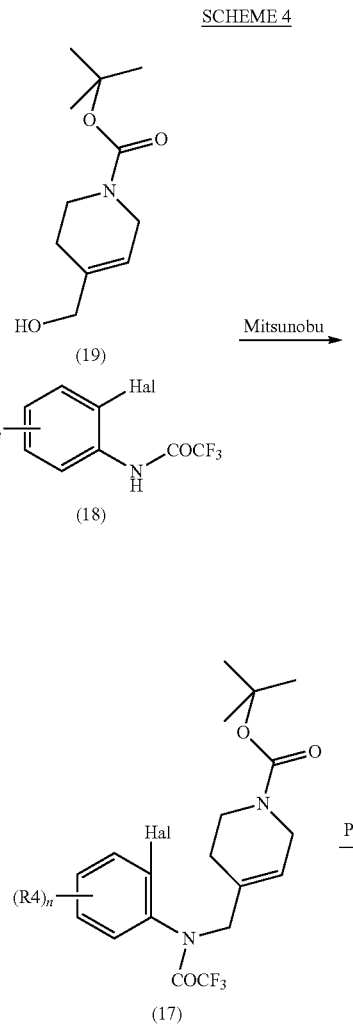

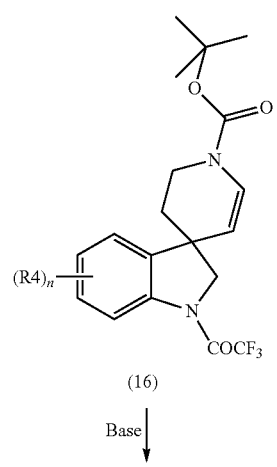

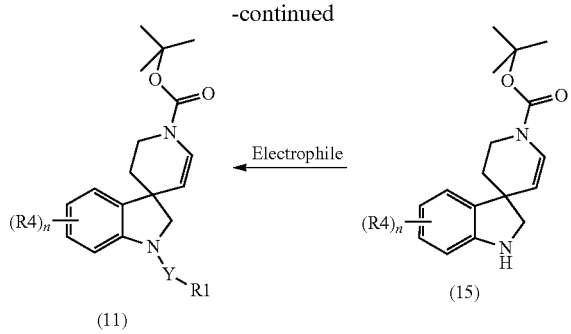

The compounds of formula (I) can be used to combat and control infestations of insect pests such as *Lepidoptera*, Diptera, Hemiptera, Thysanoptera, Orthoptera, Dictyoptera, Coleoptera, *Siphonaptera, Hymenoptera* and *Isoptera* and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossipii* (aphid), *Aphis fabae* (aphid), *Lvgtis* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anithononts grandis* (boll weevil), *Aonidiella* spp. (scale insects), *Trialeurodes* spp. (white flies), *Bemisia tabaci* (white fly), *Ostrinia nubilalis* (European corn borer), *Spodoptera* littoralis (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terininifera* (locust), *Diabrotica* spp. (rootworms), *Panonychus ulmi* (European red mite), *Panonychus citri* (citrus red mite), *Tetranychus urticae* (two-spotted spider mite), *Teiranychus cinnabarinus* (carmine spider mite), *Phyllocoptruta oleivora* (citrus rust mite), *Polyphagotarsonenmus latus* (broad mite), *Brevipalpus* spp. (flat mites), *Boophilus microplus* (cattle tick), *Dermacentor variabilis* (American dog tick), *Ctenocephalides felis* (cat flea), *Lirionmyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neoternies* spp.), the *Rhinotermitidae* (for example *Coptotermes formosanus, Reticulitermes flavipes, R. speratu, R. virginicus, R. Hesperus,* and *R. santonensis*) and the *Termitidae* (for example *Globitermes sulphureus*), *Solenopsis geminata* (fire ant), *Monomorium pharaonis* (pharaoh's ant), *Dattialinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nernaticide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (1). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, plhoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organoclhlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or
q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbetizamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example illustrates the preparation of compound III.49; 5-chloro-1-(2-chloropyridin-4-yl)carbonyl-1'-[trans-3-(4-chlorophenyl)allyl]-3'-methyl-spiro[indoline-3,4'-piperidine]

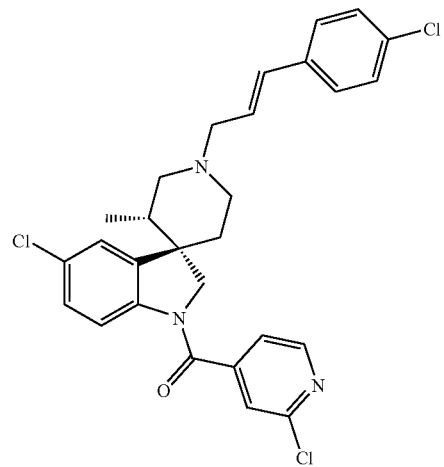

Step A: Potassium t-butoxide (1.56 g) was added portionwise to a stirred suspension of methoxymethyltriphenylphosphonium chloride (4.76 g) in tetrahydrofuran (30 ml) at 0° C. under argon. The resulting orange mixture was stirred at 0° C. for 30 min., then 1-(4-chlorocinnamyl)-3-methyl-piperidin- 4-one (1.83 g, prepared by alkylation of 3-methyl-piperidin-4-one [CAS No 5773-58-0] with 4-chloro-cinnamyl chloride) dissolved in a minimum volume of tetrahydrofuran was added dropwise and the resulting solution was stirred at room temperature for 1 hour, poured into water and extracted twice with ether. The combined organic layers were dried over sodium sulphate and concentrated in vacuo. The residue was purified by silica gel chromatography (cyclohexane:ethyl acetate 75:25) to afford 1-(4-chlorocinnamyl)-4-[1-methoxymethylidene]-3-methyl-piperidine as a mixture of diastereoisomers. MS (ES+) 292/294 (M+H$^+$).

Step B: A mixture of 1-(4-chlorocinnamyl)-4-[1-methoxymethylidene]-3-methyl-piperidine (1.25 g) and 4-chlorophenylhydrazine hydrochloride (0.85 g) in chloroform (43 ml) was treated with trifluoroacetic acid (4.3 ml) and heated at reflux under argon for 12 hours. The reaction mixture was cooled to room temperature, triethylsilane (3.1 ml) was added and the solution refluxed for 2 hours. The reaction mixture was cooled to room temperature, diluted with dichloromethane, neutralised with aqueous ammonium hydroxide, washed with brine, dried (sodium sulphate) and concentrated. The dark residue was purified by silica gel chromatography (cyclohexane:ethyl acetate 1:1+0.5% triethylamine) to afford 5-chloro-1'-[trans-3-(4-chlorophenyl)allyl]-3'-methyl-spiro[indoline-3,4'-piperidine] (1.63 g). $^1$H NMR (600 MHz, CDCl$_3$) 0.69 (d, J=9 Hz, 3H), 1.89 (m, 2H), 2.0 (m, 3H), 2.86 (dd, 1H), 2.95 (m, 1H), 3.17 (d, J=7.2 Hz, 2H), 3.31 (d, J=12 Hz, 1H), 3.58 (d, J=12 Hz, 1H), 3.65 (m, 1H), 6.30 (dt, J=7.2, 18.0 Hz, 1H), 6.49 (d, J=8.0 Hz, 1H), 6.50 (d, J=7.0 Hz, 1H), 2H), 6.94 (d, J=0.9 Hz, 1H), 6.97 (dd, J=7.0, 0.9 Hz, 1H), 7.25-7.33 (m, 4H); MS (ES+) 387/389 (M+H$^+$).

Step C: To a solution of 5-chloro-1'-[trans-3-(4-chlorophenyl)allyl]-3'-methyl-spiro[indoline-3,4'-piperidine] obtained in Step B (210 mg) and triethylamine (0.23 ml) in dichloromethane (10 ml) at 0° C. was added 2-chloro-isonicotinoyl chloride (176 mg) and the resulting solution was kept at 0° C. for 30 min., diluted with dichloromethane, washed with diluted aqueous sodium bicarbonate, dried (sodium sulphate) and concentrated. Silica gel chromatography of the residue (cyclohexane:ethyl acetate 1:1) afforded the title compound as a slight yellow solid (200 mg); M.p. 91-93° C.; MS (ES+) 526/528 (M+H$^+$)

EXAMPLE 2

This Example illustrates the preparation of 5-chloro-1-(2-chloropyridin-4-yl)carbonyl-spiro[indoline-3,4'-(1',2',3',4'-tetrahydropyridine)]-1' carboxylic acid tert-butyl ester

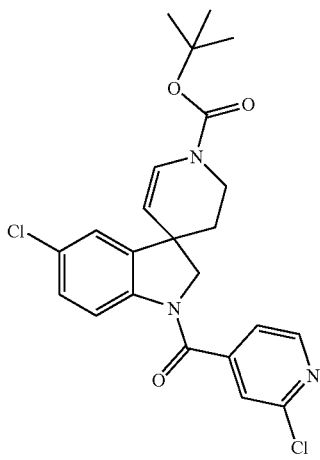

Step A: Triphenylphosphine (5.16 g) was dissolved in tetrahydrofuran (130 ml) and the solution was cooled to 0° C. under argon. Diisopropylazodicarboxylate (3.82 ml) was added dropwise over 10 min and the resulting mixture was stirred at 0° C. for 20 min (formation of a white precipitate). N-(4-Chloro-2-iodo-phenyl)-2,2,2-trifluoro-acetamide (5.5 g) was added as a solid, followed by 4-hydroxymethyl-3,6-dihydro-2H-pyridine-1-carboxylic acid tert-butyl ester (J. Org. Chem. 2001, 66, 5545-5551, 3.4 g) dissolved in a minimum volume of tetrahydrofuran. The reaction mixture was allowed to warm to room temperature and stirred for 12 hours. The solution was then concentrated in vacuo and the residue subjected to silica gel chromatography (cyclohexane:ethyl acetate 9:1) to afford 4-{[(4-chloro-2-iodo-phenyl)-(2,2,2-trifluoro-acetyl)-amino]-methyl}-3,6-dihydro-2H-pyridine-1-carboxylic acid tert-butyl ester (4.7 g). $^1$H NMR (600 MHz, CDCl$_3$) 1.5 (s, 9H), 2.20 (m, 2H), 3.49 (m, 1H), 3.50 (d, J=17 Hz, 1H), 3.55 (m, 1H), 3.8-3.9 (m, 1H), 5.02 (d, J=17 Hz, 1H), 5.40 (s, 1H), 7.0 (m, 1H), 7.38 (dd, 1H), 7.92 (d, 1H); MS (ES+) 445/447 (M+H$^+$—CO$_2$-isobutene), 486/488 (M+H$^+$-isobutene).

Step B: In a dried, argon purged flask, 4-{[(4-chloro-2-iodo-phenyl)-(2,2,2-trifluoro-acetyl)-amino]-methyl}-3,6-dihydro-2H-pyridine-1-carboxylic acid tert-butyl ester obtained in Step A (3.55 g) was dissolved in dimethylformamide (55 ml); triethylamine (2.3 ml), tetrabutylammonium bromide (2.5 g) and palladium(II) acetate (0.22 g) were successively added and the solution was heated at 80° C. for 3 hours. After cooling to room temperature, the reaction mixture was diluted with ethyl acetate, washed with brine, dried over sodium sulphate and concentrated in vacuo. The crude residue was dissolved in methanol (140 ml) and water (30 ml), placed under argon and potassium carbonate (6.8 g) was added. The reaction mixture was stirred for 1 hour at room temperature, the mixture was filtered and the filtrate concentrated in vacuo. The residue was diluted with ethyl acetate, washed with brine, dried (sodium sulphate) and concentrated in vacuo. Silica gel chromatography of the residue (cyclohexane:ethyl acetate 8:2) afforded 5-chloro-spiro[indoline-3,4'-(1',2',3',4'-tetrahydropyridine)]-1' carboxylic acid tert-butyl ester (1.3 g) as a a pale yellow powder. M.p. 50-51° C.; $^1$H NMR (600 MHz, CDCl$_2$CDCl$_2$, 80° C.) 1.54 (s, 9H), 1.83 (m, 1H), 1.99 (m, 1H), 3.36 (d, J=11.4 Hz, 1H), 3.50 (d, J=11.4 Hz, 1H), 3.51 (m, 1H), 3.75 (brs, 1H, NH), 3.78 (m, 1H), 4.81 (d, J=8.6 Hz, 1H), 6.57 (d, J=10.2 Hz, 1H), 6.98 (d, J=2.4 Hz, 1H), 7.02 (m, 1H), 7.03 (dd, J=10.2, 2.4 Hz, 1H); $^{13}$C NMR (125 MHz, CDCl$_2$CDCl$_2$, 80° C.) selected data 28.2, 33.2, 39.1, 60.6, 108.5, 110.2, 123.5, 126.4, 127.5; MS (ES+) 221/223 (M+H$^+$—CO$_2$-isobutene), 265/267 (M+H$^+$-isobutene); 321/323 (M+H$^+$).

Step C: 5-Chloro-spiro[indoline-3,4'-(1',2',3',4'-tetrahydropyridine)]-1' carboxylic acid tert-butyl ester (274 mg) was acylated in dichloromethane (10 ml) with 2-chloroisonicotinoyl chloride (250 mg) in the presence of triethylamine (0.48 ml) using the method described in Example 1 Step C to give the title compound (360 mg). MS (ES+) 360/362 (M+H$^+$—CO$_2$-isobutene), 404/406 (M+H$^+$-isobutene).

EXAMPLE 3

This Example illustrates the preparation of compound CIII.49, 5-chloro-1-(2-chloropyridin-4-yl)carbonyl-1'-[trans-3-(4-chlorophenyl)allyl]-3'-hydroxy-spiro[indoline-3,4'-piperidine]

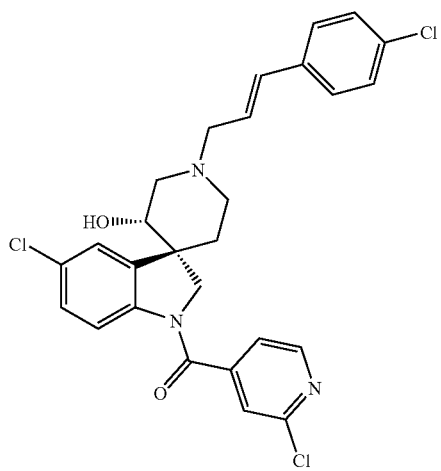

Borane-methylsulfide complex (1M in dichloromethane, 1.05 ml) was added dropwise under argon to a solution of 5-chloro-1-(2-chloropyridin-4-yl)carbonyl-spiro[indoline-3,4'-(1',2',3',4'-tetrahydropyridine)]-1' carboxylic acid tert-butyl ester (Example 2, 350 mg) in tetrahydrofuran (15 ml) at room temperature and the resulting solution was stirred at room temperature for 18 hours. 3N NaOH (0.9 ml) was added, followed by 30% aqueous hydrogen peroxide (0.9 ml) and the resulting mixture was stirred at room temperature for 1 hour, poured into water, extracted twice with ethyl acetate, dried (sodium sulphate) and concentrated in vacuo. The major product was isolated by silica gel chromatography (cyclohexane:ethyl acetate 7:3) to give 125 mg of a solid. The latter was dissolved in dichloromethane (10 ml) and treated with trifluoroacetic acid (1 ml) at room temperature for 2 hours. The solution was partitioned between water and dichloromethane, the organic layer was neutralised with saturated aqueous sodium bicarbonate, dried (sodium sulphate) and concentrated in vacuo. The residue was dissolved in acetonitrile (5 ml) and treated with diisopropylethylamine (0.065 ml) and 4-chlorocinnamyl bromide (58 mg) for 12 hours at room temperature under argon. Standard aqueous work-up afforded a residue which was purified by flash chromatography (silica gel, ethyl acetate:methanol 98:2) to give the title product (51 mg) as a colorless solid. M.p. 110° C.; MS (ES+) 528/530/532/533 (M+H+).

EXAMPLE 4

This Example illustrates the preparation of compound CCIII.49, 5-chloro-1-(2-chloropyridin-4-yl)carbonyl-1'-[trans-3-(4-chlorophenyl)allyl]-3'-fluoro-spiro[indoline-3,4'-piperidine]

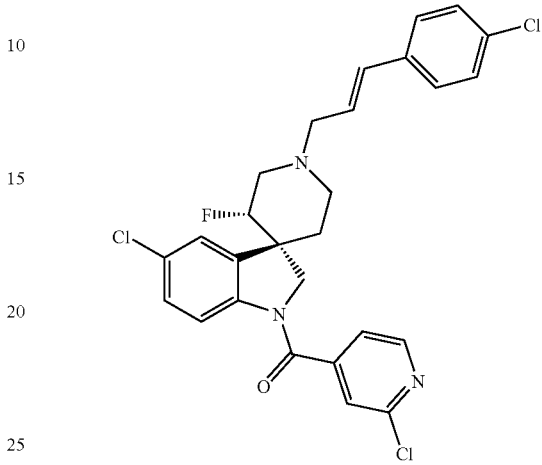

[1-(Chloromethyl)-4-fluoro-1,4-diazoniabicyclo[2.2.2]octane bis(tetrafluoroborate)] (Selectfluor™, 266 mg) was added to a solution of 5-chloro-1-(2-chloropyridin-4-yl)carbonyl-spiro[indoline-3,4'-(1',2',3',4'-tetrahydropyridine)]-1' carboxylic acid tert-butyl ester (Example 2, 345 mg) in dimethylformamide (20 ml) at room temperature and the resulting solution was stirred at 70° C. for 1 hour, cooled to room temperature, poured into water (50 ml) and extracted twice with ethyl acetate; the combined organic layers were washed with brine, dried (sodium sulphate), concentrated in vacuo and the residue purified by silica gel chromatography (cyclohexane:ethyl acetate 8.2) to afford 5-chloro-1-(2-chloropyridin-4-yl)carbonyl-3'-fluoro-2'-hydroxy-spiro[indoline-3,4'-piperidine]1' carboxylic acid tert-butyl ester (200 mg) as a colorless solid; MS (ES+) 496/498 (M+H+). This product was dissolved in dichloromethane (10 ml) and treated successively with triethylsilane (0.3 ml) and trifluoroacetic acid (0.57 ml); the solution was stirred under argon for 12 hrs, diluted with dichloromethane, neutralised with aqueous sodium bicarbonate, dried (sodium sulphate) and concentrated in vacuo. The residue was dissolved in acetonitrile (10 ml) and treated with diisopropylethylamine (0.1 ml) and 4-chlorocinnamyl chloride (71 mg) for 12 hours at reflux under argon. Standard aqueous work-up afforded a residue which was purified by flash chromatography (silica gel, cyclohexane:ethyl acetate 7:3) to give the title product (111 mg) as a colorless solid. M.p. 96-97° C.; MS (ES+) 530/532/534 (M+H+).

EXAMPLE 5

This Example illustrates the preparation of compound CCCIII.49, 5-chloro-1-(2-chloropyridin-4-yl)carbonyl-1'-[trans-3-(4-chlorophenyl)allyl]-3',3'-difluoro-spiro[indoline-3,4'-piperidine]

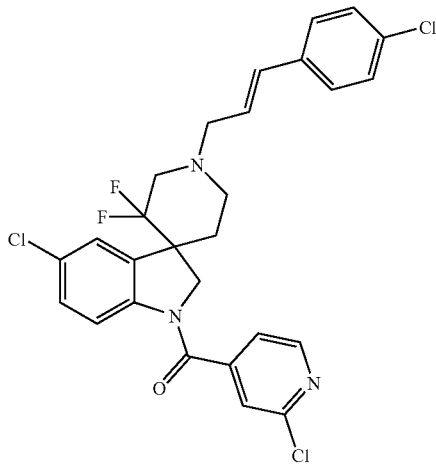

[1-(Chloromethyl)-4-fluoro-1,4-diazoniabicyclo[2.2.2]octane bis(tetrafluoroborate)] (Selectfluor™, 1.05 g) was added to a solution of 5-chloro-1-(2-chloropyridin-4-yl)carbonyl-spiro[indoline-3,4'-(1',2',3',4'-tetrahydropyridine)]-1' carboxylic acid tert-butyl ester (Example 2, 345 mg) in dimethylformamide (15 ml) at room temperature and the resulting solution was stirred at 80° C. for 2 hours, cooled to room temperature, poured into water and extracted twice with ethyl acetate; the combined organic layers were washed with brine, dried (sodium sulphate), concentrated in vacuo and the residue purified by silica gel chromatography (cyclohexane:ethyl acetate 65.35) to afford 5-chloro-1-(2-chloropyridin-4-yl)carbonyl-3',3'-difluoro-2'-hydroxy-spiro[indoline-3,4'-piperidine]1' carboxylic acid tert-butyl ester (217 mg) as a colorless solid; MS (ES+) 514/516 (M+H$^+$). This product was dissolved in dichloromethane (14 ml) and treated successively with triethylsilane (0.34 ml) and trifluoroacetic acid (0.64 ml); the solution was stirred under argon for 12 hrs, diluted with dichloromethane, neutralised with aqueous sodium bicarbonate, dried (sodium sulphate) and concentrated in vacuo. The residue was dissolved in acetonitrile (10 ml) and treated with diisopropylethylamine (0.1 ml) and 4-chlorocinnamyl chloride (71 mg) for 10 hours at reflux under argon. Standard aqueous work-up afforded a residue which was purified by flash chromatography (silica gel, cyclohexane:ethyl acetate 7:3) to give the title product I.4 (118 mg) as a colorless solid. M.p. 100-101° C.; $^1$H NMR (600 MHz, CDCl$_2$CDCl$_2$, 80° C.) 1.86 (m, 1H), 2.20 (m, 1H), 2.41 (m, 1H), 2.45 (m, 1H), 3.02 (d, J=12 Hz, 1H), 3.24 (m, 3H), 3.85 (d, J=12 Hz, 1H), 4.24 (m, 1H), 6.24 (dd, J=12 Hz, 7.2 Hz, 1H), 6.6 (d, J=12 Hz, 1H), 7.27-7.47 (m, 9H), 8.57 (d, J=6 Hz, 1H); $^{13}$C NMR (125 MHz, CDCl$_2$CDCl$_2$, 80° C.) selected data 34.5, 48.4, 55.5, 56.8, 59.3, 119.4, 120.3, 121.5, 125.9, 126.1, 127.5, 128.6, 128.9, 129.9, 132.2, 150.6; MS (ES+) 548 (M+H$^+$).

EXAMPLE 6

This Example illustrates the pesticidal/insecticidal properties of compounds of formula (I). Test against were performed as follows:

*Spodoptera littoralis* (Egyptian cotton leafworm)
Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*:
CIII-49.

*Heliothis virescens* (Tobacco Budworm):
Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*:
III-49, CIII-49, CCIII-49, CCCIII-49.

*Plutella xylostella* (Diamond Back Moth):
24-well microtiter plate (MTP) with artificial diet was treated with test solutions at an application rate of 18.2 ppm by pipetting. After drying, the MTP's were infested with larvae (L2)(10-15 per well). After an incubation period of 5 days, samples were checked for larval mortality, antifeedant and growth regulation. The following compounds gave at least 80% control of *Plutella xylostella*:
CTII-49, CCIII-49, CCCIII-49.

*Aedes aegipti* (Yellow Fever Mosquito):
10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*
III-49, CIII-49, CCIII-49.

The invention claimed is:
1. A compound of formula I:

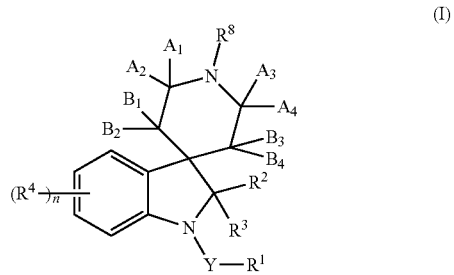

wherein:
Y is C=O;
R$^1$ is optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or NR$^{13}$R$^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$;

$R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$;

$R^{16}$, $R^{17}$ and $R^{18}$ are each independently H or lower alkyl;

$R^{19}$ and $R^{20}$ are each independently optionally substituted alkyl, optionally substituted aryl or optionally substituted heteroaryl;

$R^2$ and $R^3$ are each independently hydrogen, halogen, cyano, optionally substituted alkyl or optionally substituted alkoxy;

each $R^4$ is independently halogen, cyano, optionally substituted $C_{1-8}$ alkyl, optionally substituted $C_{3-7}$ cycloalkyl, optionally substituted alkoxy;

n is 0, 1, 2, 3 or 4;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

$A_1$, $A_2$, $A_3$, $A_4$, $B_1$, $B_2$, $B_3$ and $B_4$ are each independently hydrogen, halogen, cyano, optionally substituted $C_{1-8}$ alkyl, optionally substituted $C_{3-7}$ cycloalkyl or optionally substituted alkoxy;

or salts or N-oxides thereof provided that when $B_1$, $B_2$, $B_3$ and $B_4$ are all H, either both $A_1$ and $A_2$ are different from H or both $A_3$ and $A_4$ are different from H.

2. A compound according to claim 1 wherein $R^2$ and $R^3$ are each independently hydrogen, $C_{1-6}$ alkyl, $C_{1-6}$ haloalkyl, $C_{1-6}$ alkoxy or cyano.

3. A compound according to claim 1 wherein:

$R^1$ is $C_{1-6}$ alkyl; $C_{1-6}$ cyanoalkyl; $C_{1-6}$ haloalkyl; $C_{3-7}$ cycloalkyl($C_{1-4}$)alkyl; $C_{1-6}$ alkoxy($C_{1-6}$)alkyl; heteroaryl($C_{1-6}$)alkyl wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, or arylcarbonyl, or two adjacent positions on the heteroaryl group may be cyclised to form a 5, 6 or 7 membered carbocyclic or heterocyclic ring, itself optionally substituted with halogen; aryl($C_{1-6}$)alkyl wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, or arylcarbonyl, or two adjacent positions on the aryl group may be cyclised to form a 5, 6 or 7 membered carbocyclic or heterocyclic ring, itself optionally substituted with halogen; $C_{1-6}$ alkylcarbonylamino($C_{1-6}$)alkyl; aryl which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, or arylcarbonyl, or two adjacent positions on the aryl system may be cyclised to form a 5, 6 or 7 membered carbocyclic or heterocyclic ring, itself optionally substituted with halogen; heteroaryl which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, or arylcarbonyl, or two adjacent positions on the heteroaryl system may be cyclised to form a 5, 6 or 7 membered carbocyclic or heterocyclic ring, itself optionally substituted with halogen; $C_{1-6}$ alkoxy; $C_{1-6}$ haloalkoxy; phenoxy wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino); heteroaryloxy optionally substituted by halo, nitro, cyano, $C_{1-6}$ alkyl, $C_{1-6}$ haloalkyl, $C_{1-6}$ alkoxy or $C_{1-6}$ haloalkoxy); heterocyclyloxy optionally substituted by halo, $C_{1-6}$ alkyl, $C_{1-6}$ haloalkyl, $C_{1-6}$ alkoxy or $C_{1-6}$ haloalkoxy); cyano; $C_{2-6}$ alkenyl; $C_{2-6}$ alkynyl; $C_{3-6}$ cycloalkyl; $C_{5-7}$ cycloalkenyl; heterocyclyl optionally substituted by halo, nitro, cyano, $C_{1-6}$ alkyl, $C_{1-6}$ haloalkyl, $C_{1-6}$ alkoxy or $C_{1-6}$ haloalkoxy; $C_{1-6}$ alkylthio; $C_{1-6}$ haloalkylthio; or $NR^{13}R^{14}$; and $R^{13}$ and $R^{14}$ are each independently hydrogen; $C_{1-6}$ alkyl; $C_{1-6}$ haloalkyl; $C_{1-6}$ alkoxy($C_{1-6}$)alkyl; phenyl which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl; phenyl($C_{1-6}$)alkyl wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, or $C_{1-6}$ alkoxycarbonyl, or two adjacent positions on the phenyl ring may be cyclised to form a 5, 6 or 7 membered carbocyclic or heterocyclic ring, itself optionally substituted with halogen; heteroaryl($C_{1-6}$)alkyl wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, or arylcarbonyl, or two adjacent positions on the heteroaryl group may be cyclised to form a 5, 6 or 7 membered carbocyclic or heterocyclic ring, itself optionally substituted with halogen; or heteroaryl (which may be optionally substituted by (i) halo, (ii) nitro, (iii) cyano, (iv) $C_{1-6}$ alkyl, (v) $C_{1-6}$ haloalkyl, (vi) $C_{1-6}$ alkoxy, (vii) $C_{1-6}$ haloalkoxy, (viii) $C_{1-4}$ alkoxycarbonyl $C_{1-6}$ alkylcarbonylamino, (ix) phenyloxycarbonylamino wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, (x) amino, (xi) $C_{1-6}$ alkylamino or (xii) phenylamino wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

4. A compound according to claim 1 wherein:
each $R^4$ is independently halogen; cyano; $C_{1-8}$ alkyl; $C_{1-8}$ haloalkyl; $C_{1-6}$ cyanoalkyl; $C_{1-6}$ alkoxy($C_{1-6}$)alkyl; $C_{3-7}$ cycloalkyl($C_{1-6}$)alkyl; $C_{5-6}$ cycloalkenyl($C_{1-6}$)alkyl; $C_{3-6}$ alkenyloxy($C_{1-6}$)alkyl; $C_{3-6}$ alkynyloxy($C_{1-6}$)alkyl; aryloxy($C_{1-6}$)alkyl; $C_{1-6}$ carboxyalkyl; $C_{1-6}$ alkylcarbonyl($C_{1-6}$)alkyl; $C_{2-6}$ alkenylcarbonyl($C_{1-6}$)alkyl; $C_{2-6}$ alkynylcarbonyl($C_{1-6}$)-alkyl; $C_{1-6}$ alkoxycarbonyl($C_{1-6}$) alkyl; $C_{3-6}$ alkenyloxycarbonyl($C_{1-6}$)alkyl; $C_{3-6}$ alkynyloxycarbonyl($C_{1-6}$)alkyl; aryloxycarbonyl($C_{1-6}$)alkyl; $C_{1-6}$ alkylthio($C_{1-6}$)alkyl; $C_{1-6}$ alkylsulfinyl($C_{1-6}$)alkyl; $C_{1-6}$ alkylsulfonyl($C_{1-6}$)alkyl; aminocarbonyl($C_{1-6}$) alkyl; $C_{1-6}$ alkylaminocarbonyl($C_{1-6}$)alkyl; di($C_{1-6}$) alkylaminocarbonyl($C_{1-6}$)alkyl; phenyl($C_{1-4}$)alkyl wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; heteroaryl($C_{1-4}$)alkyl wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy; heterocyclyl($C_{1-4}$)alkyl wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy; $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl;

n is 0, 1, 2 or 3.

5. A compound according to claim 1 wherein:

$R^8$ is $C_{1-10}$ alkyl; $C_{1-10}$ haloalkyl; aryl($C_{1-6}$)alkyl wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; heteroaryl($C_{1-6}$)alkyl wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; arylcarbonyl-($C_{1-6}$) alkyl wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, and the alkyl group may be optionally substituted by aryl; $C_{2-8}$ alkenyl; $C_{2-8}$ haloalkenyl; aryl ($C_{2-6}$)-alkenyl wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, or $C_{1-6}$ alkoxycarbonyl, or two adjacent substituents can cyclise to form a 5, 6 or 7 membered carbocyclic or heterocyclic ring; heteroaryl($C_{2-6}$)-alkenyl wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, or $C_{1-6}$ alkoxycarbonyl, or two adjacent substituents can cyclise to form a 5, 6 or 7 membered carbocyclic or heterocyclic ring; $C_{2-6}$ alkynyl; phenyl ($C_{2-6}$)alkynyl wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; $C_{3-7}$ cycloalkyl; $C_{1-6}$ alkoxycarbonyl; $C_{1-6}$ alkylcarbonyl; $C_{1-6}$ haloalkylcarbonyl; aryl ($C_{2-6}$)alkenylcarbonyl wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; or —C($R^{51}$)($R^{52}$)—[$CR^{53}$=$CR^{54}$]z-$R^{55}$;

z is 1 or 2;

$R^{51}$ and $R^{52}$ are each independently H, halo or $C_{1-2}$ alkyl;

$R^{53}$ and $R^{54}$ are each independently H, halogen, $C_{1-4}$ alkyl or $C_{1-4}$ haloalkyl; and $R^{55}$ is optionally substituted aryl or optionally substituted heteroaryl.

6. A compound according to claim 1 wherein $A_1$, $A_2$, $A_3$, $A_4$, $B_1$, $B_2$, $B_3$ and $B_4$ are each independently hydrogen, halo, cyano or $C_{1-3}$ alkyl.

7. An insecticidal acaricidal and nematicidal composition comprising an insecticidally, acaricidally or nematicidally effective amount of a compound as defined in claim 1.

8. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound according to claim 1.

9. A compound according to claim 1 wherein $R^1$ is optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$.

10. A compound according to claim 9 wherein $R^2$, $R^3$, $R^4$, $A_1$, $A_2$, $A_3$, $A_4$, $B_1$, $B_2$, $B_3$ and $B_4$ are each independently hydrogen, optionally substituted $C_{1-8}$ alkyl, halo, optionally substituted alkoxy, or cyano.

11. A compound according to claim 1 wherein $R^2$, $R^3$, $R^4$, $A_1$, $A_2$, $A_3$, $A_4$, $B_1$, $B_2$, $B_3$ and $B_4$ are each independently hydrogen, optionally substituted $C_{1-8}$ alkyl, halo, optionally substituted alkoxy, or cyano.

12. A compound according to claim 9 wherein $R^1$ is pyridyl optionally substituted by halo, $C_{1-3}$ alkyl or $C_{1-3}$ haloalkyl.

13. An insecticidal acaricidal and nematicidal composition comprising an insecticidally, acaricidally or nematicidally effective amount of a compound as defined in claim 9.

14. An insecticidal acaricidal and nematicidal composition comprising an insecticidally, acaricidally or nematicidally effective amount of a compound as defined in claim 10.

15. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound according to claim 10.

* * * * *